(12) United States Patent
Voskoboynikov et al.

(10) Patent No.: US 7,214,746 B2
(45) Date of Patent: May 8, 2007

(54) PHOSPHORUS BRIDGED METALLOCENE COMPOUNDS FOR OLEFIN POLYMERIZATION

(75) Inventors: Alexander Z. Voskoboynikov, Moscow (RU); Denis N. Kazyulkin, Moscow (RU); Vyatcheslav V. Izmer, Moscow (RU); Alexey N. Ryabov, Moscow (RU); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 25 days.

(21) Appl. No.: 11/077,741

(22) Filed: Mar. 11, 2005

(65) Prior Publication Data

US 2005/0239981 A1    Oct. 27, 2005

Related U.S. Application Data

(60) Provisional application No. 60/564,907, filed on Apr. 23, 2004.

(51) Int. Cl.
*C08F 4/60* (2006.01)
*C08F 4/6392* (2006.01)
*C08F 210/02* (2006.01)
*C08F 210/06* (2006.01)

(52) U.S. Cl. ............... 526/161; 526/133; 526/134; 526/160; 526/165; 526/172; 526/943; 556/19; 556/53; 502/103; 502/152; 502/155

(58) Field of Classification Search ............ 526/133, 526/134, 160, 161, 165, 172, 943; 556/19, 556/53; 502/103, 152, 155
See application file for complete search history.

(56) References Cited

U.S. PATENT DOCUMENTS

| | | | |
|---|---|---|---|
| 6,156,844 A * | 12/2000 | Hashimoto et al. | 525/240 |
| 6,191,241 B1 | 2/2001 | Ostoja-Starzewski et al. | 526/161 |
| 6,353,064 B1 | 3/2002 | Ostoja-Starzewski et al. | 526/160 |
| 6,632,911 B1 * | 10/2003 | Takahashi et al. | 526/348.1 |

FOREIGN PATENT DOCUMENTS

| | | |
|---|---|---|
| WO | 99/40129 | 8/1999 |
| WO | 99/42497 | 8/1999 |

OTHER PUBLICATIONS

Gobley et al., "Some New exo,exo-Bis(isodicyclopentadienyl)titanium and -zirconium Dichloride Derivatives: Synthesis, Characterization, and Evaluation as Propene Polymerization Catalysts", Organometallics, 1998, 17, 4897-4903.

Leyser et al., "Phosphonium-Bridged Alkali and Alkaline-Earth Metallocene Complexes", Organometallics, 1998, 17, 2155-2161.

Schaverien et al., "Phosphorus-bridged metallocenes: New homogeneous catalysts for the polymerization of propene", Journal of Molecular Catalysis A: Chemical 128(1998), 245-256.

Alt et al., "PPh-bridged metallocene complexes of the type ($C_{13}H_8$-PPh-$C_{13}H_8$)$MCl_2$ (M=Zr,Hf)", Journal of Organometallic Chemistry, 568, (1998) 127-131.

Shin et al., "Phosphorus-Bridged *ansa*-Metallocene Complexes of Titanium, Zirconium, and Hafnium: The Syntheses and Structures of [$PhP(C_5Me_4)_2$]$MX_2$ and [$Ph(E)P(C_5Me_4)_2$]$MX_2$ (E=O, S, Se) Derivatives", Organometallics, 1999, 18, 6-9.

Häp et al., "Dichloro[bis($\eta^3$-2,4-cyclopentadien-1-yl)alkylphosphan]zirconium: PR($C_5H_4$)$_2$$ZrCl_2$; R=Me, Et, $^i$Pr, $^t$Bu", Z. Naturforsch. 54 b, 482-486 (1999).

Shin et al., "Cationic *Ansa*-Zirconocene and Hafnocene Derivatives of a Monoanionic Phosphonium-Bridged Bis(permethylcyclopentadienyl) Ligand: Synthesis and Structural Characterization of {[$Me_2P(C_5Me_4)_2$]$MCl_2$}$^+$ (M=Zr, Hf) and {[$Me_2P(C_5Me_4)_2$]$ZrMe_2$}$^+$", Organometallics, 2000, 19, 5155-5159.

* cited by examiner

*Primary Examiner*—Caixia Lu
(74) *Attorney, Agent, or Firm*—Catherine L. Bell

(57) ABSTRACT

This invention relates to metallocene compounds represented by formula:

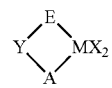

wherein
M is a group 3, 4, 5 or 6 transition metal atom, or a lanthanide metal atom, or actinide metal atom;
E is a substituted or unsubstituted indenyl ligand that is bonded to Y through the two position of the indenyl ring;
A is bonded to Y, and is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand, or A may, independently, be defined as E;
Y is a phosphorus containing group that is bonded to both E and A, and is bonded via the phosphorus atom to E; and
X are, independently, univalent anionic ligands, or both X are joined and bound to the metal atom to form a metallocycle ring, or both X join to form a chelating ligand, a diene ligand, or an alkylidene ligand.

75 Claims, 3 Drawing Sheets

PHOSPHORUS BRIDGED METALLOCENE COMPOUNDS FOR OLEFIN POLYMERIZATION

This application claims the benefit of U.S. application Ser. No. 60/564,907 filed Apr. 23, 2004.

FIELD

A series of novel phosphorus bridged transition metal compounds have been synthesized, and when activated, have been shown to be useful as olefin polymerization catalysts.

BACKGROUND

Various processes and catalysts exist for the homopolymerization or copolymerization of olefins. For many applications, it is desirable for a polyolefin to have a high weight average molecular weight while having a relatively narrow molecular weight distribution. A high weight average molecular weight, when accompanied by a narrow molecular weight distribution, provides a polyolefin with, among other things, high strength properties.

Traditional Ziegler-Natta catalysts systems—a transition metal compound co-catalyzed by an aluminum alkyl—are typically capable of producing polyolefins having a high molecular weight, but with a broad molecular weight distribution.

More recently a catalyst system has been developed wherein the transition metal compound has two or more cyclopentadienyl ring ligands—such transition metal compound being referred to herein as a "metallocene—which catalyzes the production of olefin monomers to polyolefins. Accordingly, titanocenes, zirconocenes and hafnocenes, have been utilized as the transition metal component in such "metallocene" containing catalyst system for the production of polyolefins and ethylene-alpha-olefin copolymers.

Organometallics 1998, 17, 2155 discloses phosphorus bridged bis-cyclopentadienyl ligands with four bonds to the phosphorus bridge. Group 4 metals are not used.

J. Mol. Cat. A. 1998, 128, 245 discloses phosphorus bridged ligands with three bonds to the phosphorus ligand. Compounds include PhP(fluoreyl)(cyclopentadienyl)ZrCl$_2$, PhP(fluorenyl)$_2$ZrCl$_2$, 1,1'-PhP(2-methyl-4-phenylindenyl)$_2$ZrCl$_2$ (bridged in the one position), 1,1'-iso-propylP(PhP(2-methyl-4-phenylindenyl)$_2$ZrCl$_2$ (bridged in the one position), 1,1'-PhP(indenyl)$_2$ZrCl$_2$ (bridged in the one position).

J. Organomet. Chem. 1998, 568, 127 discloses phosphorus bridged ligands with three bonds to the phosphorous ligand. Compounds include PhP(fluorenyl)$_2$ZrCl$_2$, and PhP(fluorenyl)$_2$HfCl$_2$. The paper also discloses some additional ligand preps, but not with bridges in the 2-position of the indenyl ligand. Polymerization data is included.

Organometallics 1999, 18, 6 discloses phosphorous bridged bis-cyclopentadienyl Group 4 metallocenes with three or four bonds to the phosphorous ligand (e.g. Cp*$_2$PMe, Cp*2PMe(E) with S=O, S, Se). There is a note in the paper stating that the compounds are active polymerization catalysts when activated by MAO.

Z. Naturforsch., B 1999, 54, 482 discloses phosphorous bridged bis-cyclopentadienyl complexes.

Organometallics 2000, 19, 5155—Discloses phosphorous bridged bis-cyclopentadienyl Group 4 metallocenes with 4 bonds to the phosphorous ligand (e.g. Cp*$_2$PMe$_2$). This makes the metallocene ionic as in [Me$_2$PCp*$_2$ZrCl$_2$]$^+$[I]$^-$. There is no mention of polymerization.

SUMMARY OF THE INVENTION

Therefore, in accordance with an aspect of the present invention, there are provided metallocene compounds represented by formula (1):

wherein
M is a group 3, 4, 5 or 6 transition metal atom, or a lanthanide metal atom, or actinide metal atom;
E is a substituted or unsubstituted indenyl ligand that is bonded to Y through the two position of the indenyl ring;
A is bonded to Y, and is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand, or A may, independently, be defined as E;
Y is a phosphorus containing group that is bonded to both E and A, and is bonded via the phosphorus atom to E; and
X is, independently, univalent anionic ligands, or both X are joined and bound to the metal atom to form a metallocycle ring, or both X join to form a chelating ligand, a diene ligand, or an alkylidene ligand.

This invention further relates to a catalyst system comprised of the above metallocenes combined with an activator and to a process to polymerize unsaturated monomers using such catalyst system.

DEFINITIONS

Figure 1:
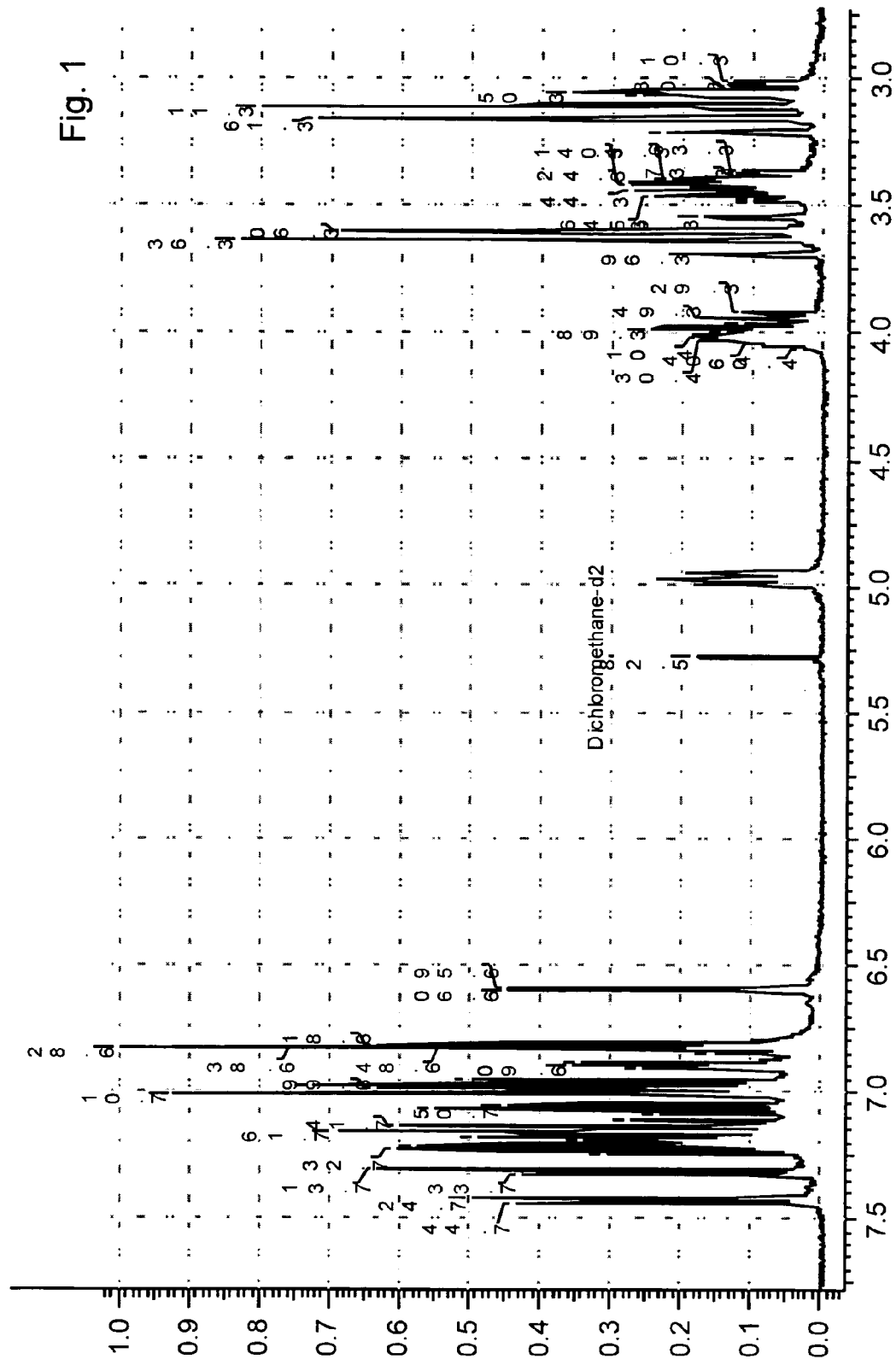
FIG. 1 is a $^1$H NMR spectrum of compound 12 in CD$_2$Cl$_2$.

As used herein, the numbering scheme for the Periodic Table Groups is the new notation as set out in CHEMICAL AND ENGINEERING NEWS, 63(5), 27 (1985).

As used herein, Me is methyl, t-Bu and $^t$Bu are tertiary butyl, s-Bu and $^s$Bu is sec-butyl, i-Bu and $^i$Bu are isobutyl, iPr and $^i$Pr are isopropyl, Cy is cyclohexyl, and Ph is phenyl.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be C$_1$–C$_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below. When referring to a hydrogen substitutent, the terms "hydrogen" and "hydrogen radical" are used interchangeably.

Substituted hydrocarbyl radicals are radicals in which at least one hydrogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. CF$_3$).

Substituted halocarbyl radicals are radicals in which at least one halocarbyl hydrogen or halogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include SiH$_3$, SiH$_2$R*, SiHR*$_2$, SiR*$_3$, SiH$_2$(OR*), SiH(OR*)$_2$, Si(OR*)$_3$, SiH$_2$(NR*$_2$), SiH(NR*$_2$)$_2$, Si(NR*$_2$)$_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include GeH$_3$, GeH$_2$R*, GeHR*$_2$, GeR*$^5$$_3$, GeH$_2$(OR*), GeH(OR*)$_2$, Ge(OR*)$_3$, GeH$_2$(NR*$_2$), GeH(NR*$_2$)$_2$, Ge(NR*$_2$)$_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1–17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. . Preferred examples of polar groups include NR*$_2$, OR*, SeR*, TeR*, PR*$_2$, AsR*$_2$, SbR*$_2$, SR*, BR*$_2$, SnR*$_3$, PbR*$_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In using the terms "substituted or unsubstituted cyclopentadienyl ligand", "substituted or unsubstituted heterocyclopentadienyl ligand", "substituted or unsubstituted indenyl ligand", "substituted or unsubstituted heteroindenyl ligand", "substituted or unsubstituted fluorenyl ligand", "substituted or unsubstituted heterofluorenyl ligand", "substituted or unsubstituted pentadienyl ligand", "substituted or unsubstituted allyl ligand", and "substituted or unsubstituted boratabenzene ligand", the substitution to the aforementioned ligand may be hydrocarbyl, substituted hydrocarbyl, halocarbyl, substituted halocarbyl, silylcarbyl, or germylcarbyl.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl and fluorenyl rings. For cyclopentadienyl drawn below as an anionic ligand, all five numbered positions are equivalent. For indenyl also drawn below as an anionic ligand, positions 1 and 3 are equivalent, 4 and 7 are equivalent, and 5 and 6 are equivalent. For fluorenyl drawn below as an anionic ligand, positions 1 and 8 are equivalent, 2 and 7 are equivalent, 3 and 6 are equivalent, and 4 and 5 are equivalent.

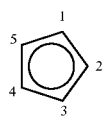

Cyclopentadienyl

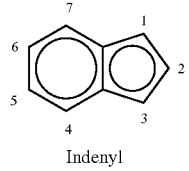

Indenyl

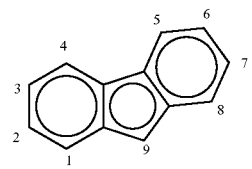

Fluorenyl

A similar numbering and nomenclature scheme is used for heteroindenyl and heterofluorenyl rings as illustrated below where Z and Q independently represent the heteroatoms O, S, Se, or Te, or heteroatom groups, NR', PR', AsR', or SbR' where R' is hydrogen, a hydrocarbyl, substituted hydrocarbyl, halocarbyl, substituted halocarbyl, silylcarbyl, or germylcarbyl substituent. The number scheme shown below is for heteroindenyl ligands or heterofluorenyl ligands that are bridged to another ligand via a bridging group.

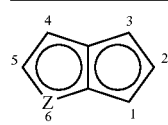 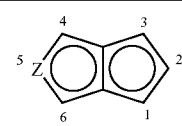

Examples include:
Cyclopenta[b]thienyl (Z = S)
Cyclopenta[b]furanyl (Z = O)
Cyclopenta[b]selenophenyl (Z = Se)
Cyclopenta[b]tellurophenyl (Z = Te)
6-Methyl-cyclopenta[b]pyrrolyl (Z = N—Me)
6-Methyl-cyclopenta[b]phospholyl (Z = P—Me)
6-Methyl-cyclopenta[b]arsolyl (Z = As—Me)
6-Methyl-cyclopenta[b]stibolyl (Z = Sb—Me)

Examples include:
Cyclopenta[c]thienyl(Z = S)
Cyclopenta[c]furanyl (Z = O)
Cyclopenta[c]selenophenyl (Z = Se)
Cyclopenta[c]tellurophenyl (Z = Te)
5-Methyl-cyclopenta[c]pyrrolyl (Z = N—Me)
5-Methyl-cyclopenta[c]phospholyl (Z = P—Me)
5-Methyl-cyclopenta[c]arsolyl (Z = As—Me)
5-Methyl-cyclopenta[c]stibolyl (Z = Sb—Me)

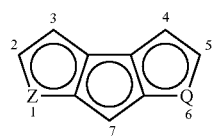 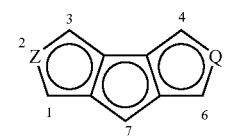 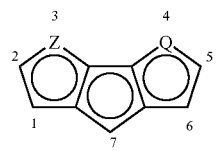

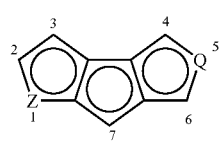 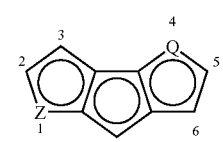 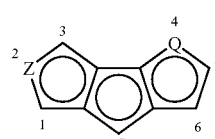

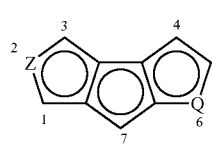 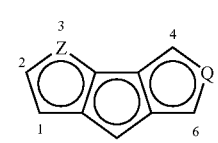 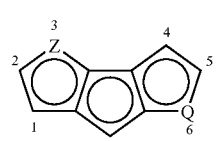

heterofluorenyl ligands

A similar numbering and nomenclature scheme is used for heterocyclopentadienyl rings as illustrated below where G and J independently represent the heteroatoms N, P, As, Sb or B. For these ligands when bridged to another ligand via a bridging group, the one position is usually chosen to be the ring carbon position where the ligand is bonded to the bridging group, hence a numbering scheme is not illustrated below.

Examples include:
Azacyclopentadiene (G = N)
Phosphacyclopentadiene (G = P)
Stibacyclopentadiene (G = Sb)
Arsacyclopentadiene (G = As)
Boracyclopentadiene (G = B)

Depending on the position of the bridging ligand, the numbering for the following ligands will change; 1,3 and 1,2 are only used in this case to illustrate the position of the heteroatoms relative to one another.

  

| Examples include: | Examples include: |
|---|---|
| 1,3-Diazacyclopentadiene (G = J = N) | 1,2-Diazacyclopentadiene (G = J = N) |
| 1,3-Diphosphacyclopentadiene (G = J = P) | 1,2-Diphosphacyclopentadiene (G = J = P) |
| 1,3-Distibacyclopentadiene (G = J = Sb) | 1,2-Distibacyclopentadiene (G = J = Sb) |
| 1,3-Diarsacyclopentadiene (G = J = As) | 1,2-Diarsacyclopentadiene (G = J = As) |
| 1,3-Diboracyclopentadiene (G = J = B) | 1,2-Diboracyclopentadiene (G = J = B) |
| 1,3-Azaphosphacyclopentadiene (G = N; J = P) | 1,2-Azaphosphacyclopentadiene (G = N; J = P) |
| 1,3-Azastibacyclopentadiene (G = N; J = Sb) | 1,2-Azastibacyclopentadiene (G = N; J = Sb) |
| 1,3-Azarsacyclopentadiene (G = N; J = As) | 1,2-Azarsacyclopentadiene (G = N; J = As) |
| 1,3-Azaboracyclopentadiene (G = N; J = B) | 1,2-Azaboracyclopentadiene (G = N; J = B) |
| 1,3-Arsaphosphacyclopentadiene (G = As; J = P) | 1,2-Arsaphosphacyclopentadiene (G = As; J = P) |
| 1,3-Arsastibacyclopentadiene (G = As; J = Sb) | 1,2-Arsastibacyclopentadiene (G = As; J = Sb) |
| 1,3-Arsaboracyclopentadiene (G = As; J = B) | 1,2-Arsaboracyclopentadiene (G = As; J = B) |
| 1,3-Boraphosphacyclopentadiene (G = B; J = P) | 1,2-Boraphosphacyclopentadiene (G = B; J = P) |
| 1,3-Borastibacyclopentadiene (G = B; J = Sb) | 1,2-Borastibacyclopentadiene (G = B; J = Sb) |
| 1,3-Phosphastibacyclopentadiene (G = P; J = Sb) | 1,2-Phosphastibacyclopentadiene (G = P; J = Sb) |

A "ring heteroatom" is a heteroatom that is within a cyclic ring structure. A "heteroatom substituent" is heteroatom containing group that is directly bonded to a ring structure through the heteroatom. A "bridging heteroatom substituent" is a heteroatom or heteroatom group that is directly bonded to two different ring structures through the heteroatom. The terms "ring heteroatom", "heteroatom substituent", and "bridging heteroatom substituent" are illustrated below where Z and R' are as defined above. It should be noted that a

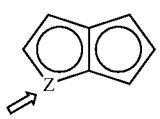

"ring heteroatom"

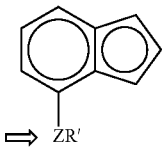

"heteroatom substituent"

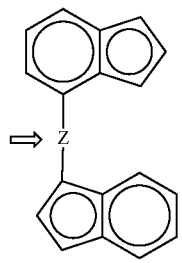

"bridging heteroatom substituent"

"heteroatom substituent" can be a "bridging heteroatom substituent" when R' is additionally defined as the ligand "A".

A "ring carbon atom" is a carbon atom that is part of a cyclic ring structure. By this definition, an indenyl ligand has nine ring carbon atoms.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2–75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst precursor and transition metal compound or complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE INVENTION

The metallocene compounds according to the invention can be used as a catalyst component for the production of homopolymers, such as homopolyethylene or homopolypropylene, and for copolymers of ethylene with other olefins including alpha-olefins or copolymers of propylene with other olefins including alpha-olefins.

In a preferred embodiment this invention relates to transition metal compounds represented by formula (2):

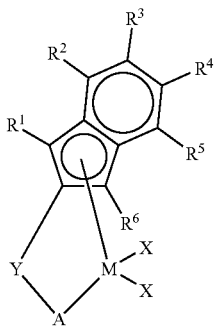

where:
M is a group 3, 4, 5 or 6 transition metal atom, or a lanthanide metal atom, or actinide metal atom, preferably a Group 4 transition metal atom selected from titanium, zirconium or hafnium;

each $R^1$, $R^2$, $R^3$, $R^4$, $R^5$, and $R^6$ is, independently, a hydrogen, a hydrocarbyl, substituted hydrocarbyl, halocarbyl, substituted halocarbyl, silylcarbyl, substituted silylcarbyl, germylcarbyl, or substituted germylcarbyl substituent, and optionally, adjacent $R^1$, $R^2$, $R^3$, $R^4$, $R^5$, and $R^6$ groups may join together to form a substituted or unsubstituted, saturated, partially unsaturated, or aromatic cyclic or polycyclic substituent;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene ligand; and Y is PR, RP—PR, or RN—PR, where each R is, independently, a hydrocarbyl, substituted hydrocarbyl, halocarbyl, or substituted halocarbyl substituent, and optionally, adjacent R groups may join together to form a substituted or unsubstituted, saturated or partially unsaturated cyclic or polycyclic substituent;

X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

More preferably this invention relates to compounds represented by formula (3):

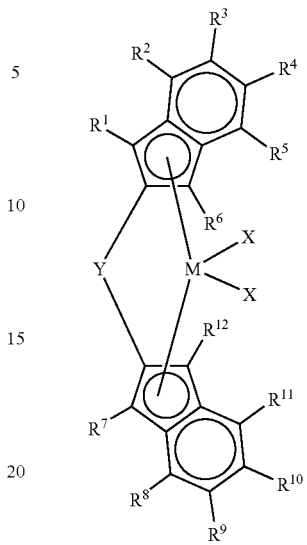

where:
M is a group 3, 4, 5 or 6 transition metal atom, or a lanthanide metal atom, or actinide metal atom, preferably a Group 4 transition metal atom selected from titanium, zirconium or hafnium;

each $R^1$, $R^2$, $R^3$, $R^4$, $R^5$, $R^6$, $R^7$, $R^8$, $R^9$, $R^{10}$, $R^{11}$, and $R^{12}$ is, independently, hydrogen, a hydrocarbyl, substituted hydrocarbyl, halocarbyl, substituted halocarbyl, silylcarbyl, substituted silylcarbyl, germylcarbyl, or substituted germylcarbyl substituent, and optionally, adjacent $R^1$, $R^2$, $R^3$, $R^4$, $R^5$, $R^6$, $R^7$, $R^8$, $R^9$, $R^{10}$, $R^{11}$, and $R^{12}$ substituents may join together to form a substituted or unsubstituted, saturated, partially unsaturated, or aromatic cyclic or polycyclic substituent; and Y is PR, RP—PR, or RN—PR, where each R is, independently, a hydrocarbyl, substituted hydrocarbyl, halocarbyl, or substituted halocarbyl substituent, and optionally, adjacent R groups may join together to form a substituted or unsubstituted, saturated or partially unsaturated cyclic or polycyclic substituent;

X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or each X may, independently, be a halogen, alkoxide, aryloxide, amide, phosphide or other univalent anionic ligand or both X can also be joined to form a anionic chelating ligand.

Examples of specific preferred embodiments are tabulated below in Table 1, where some representative components are listed. Not listed, is M which is defined above; M is, preferably, titanium, zirconium, or hafnium. When alkyl, alkenyl and alkynyl radicals are disclosed in this application the term includes all isomers and all substitution types, as previously described, unless otherwise stated. Listings for the ligand "A" include all bondable ring positions and all possible isomers. For example, a listing under "A" of indenyl would include 1-indenyl, 2-indenyl, 4-indenyl and 5-indenyl where the number indicates the bridging position; a listing of methylindenyl would include 2-(1-methylindenyl), 3-(1-methylindenyl), 4-(1-methylindenyl), 5-(1-methylindenyl), 6-(1-methylindenyl), 7-(1-methylindenyl), 1-(2-methylindenyl), 4-(2-methylindenyl), 5-(2-methylindenyl), 1-(4-methylindenyl), 2-(4-methylindenyl), 3-(4-methylindenyl), 5-(4-methylindenyl), 6-(4-methylindenyl), 7-(4-methylindenyl), 1-(5-methylindenyl), 2-(5-methylindenyl), 3-(5-methylindenyl), 4-(5-methylindenyl), 6-(5-methylindenyl), and 7-(5-methylindenyl) where the number outside the parenthesis indicates the bridging position. When more than one substituent is listed, for example, propylphenylindenyl, propyl and phenyl are each substituents on the indenyl ring, as compared to (propylphenyl)indenyl where propyl is a substituent on the phenyl ring which in turn is a substituent on the indenyl ring. The column labeled "R" shows some examples of substituents that can serve as $R^1$, $R^2$, $R^3$, $R^4$, $R^5$, $R^6$, $R^7$, $R^8$, $R^9$, $R^{10}$, $R^{11}$, and $R^{12}$. The selection of one substituent is independent of the selection any other substituent. In other words, the invention allows $R^1=R^2=R^3=R^4=R^5=R^6=R^7=R^8=R^9=R^{10}=R^{11}=R^{12}$ but does not demand it. Likewise, each X may be chosen independently of one another. To illustrate members of the transition metal component, select a transition metal, and select any combination of the species listed in Table 1 for a given formula illustrated above. For example, using formula 2, zirconium as the transition metal, and the substituents/ligands in the first row of Table 1, the compound 2,2'-methylphosphindiyl(cyclopenta[b]thienyl)(indenyl)zirconium dihydride is illustrated. Any combination of components may be selected using the above formulae 2 or 3, and any Group 3, 4, 5 or 6 transition metal atom (preferably Ti, Zr or Hf). While Table 1 does not specify the bridging position of the ligand Y, formula 2 limits it to a bridge in the two position of a substituted or unsubstituted indenyl ligand, and to any possible bridging position of the ligand A—for example, the compound 2,1'-methylphosphindiyl(indenyl)(cyclopentadienyl)zirconium dichloride, where the methylphosphindiyl bridging ligand is bonded to the 2 position of the indenyl ligand and to the 1 position of the cyclopentadienyl ligand. Formula 3 further limits the bonding of the bridging ligand to the two position of each substituted or unsubstituted indenyl ligand—for example, the compound 2,2'-cyclohexylphosphindiyl-bis(indenyl)zirconium dichloride, where the 2 and 2' indicate the cyclohexylphosphindiyl bridge is bonded to the 2-position of each of the indenyl ligands. When two different ligands are being bridged by a phosphindiyl ligand, the first number represents the position the bridge is bonded to the first ligand and the second number (typically a number followed by an') represents the position the bridge is bonded to the second ligand.

Additional examples illustrated by Table 1 would include:
2,2'-phenylphosphindiyl-bis(indenyl)zirconium dichloride,
2,1'-methylphosphindiyl(indenyl)(cyclopentadienyl)zirconium dichloride,
2,1'-cyclopropylphosphindiyl(1-methylindenyl)(tetramethylcyclopentadienyl)zirconium dichloride,
2,1'-cyclobutylphosphindiyl-bis(indenyl)zirconium methyl chloride
2,2'-(1,2-dimethyldiphosphandiyl)-bis(indenyl)hafnium dimethyl,
2,2'-(1,2-diphenyldiphosphandiyl)-bis(indenyl)titanium difluoride,
2,2'-(1-methyl-2-phenyldiphosphandiyl)-bis(indenyl)zirconium methylidene, and the like.

TABLE 1

| Y | A | $R^1$, $R^2$, $R^3$, $R^4$, $R^5$, $R^6$, $R^7$, $R^8$, $R^9$, $R^{10}$, $R^{11}$, or $R^{12}$ | X |
| --- | --- | --- | --- |
| methylphosphindiyl | cyclopenta[b]thienyl | hydrogen | hydride |
| ethylphosphindiyl | cyclopenta[b]furanyl | methyl | fluoride |
| propylphosphindiyl | cyclopenta[b]selenophenyl | ethyl | chloride |
| butylphosphindiyl | cyclopenta[b]tellurophenyl | propyl | bromide |
| pentylphosphindiyl | cyclopenta[b]pyrrolyl | butyl | iodide |
| hexylphosphindiyl | cyclopenta[b]phospholyl | pentyl | methyl |
| heptylphosphindiyl | cyclopenta[b]arsolyl | hexyl | ethyl |
| octylphosphindiyl | cyclopenta[b]stibolyl | heptyl | propyl |
| nonylphosphindiyl | methylcyclopenta[b]thienyl | octyl | butyl |
| decylphosphindiyl | methylcyclopenta[b]furanyl | nonyl | pentyl |
| undecylphosphindiyl | methylcyclopenta[b]selenophenyl | decyl | hexyl |
| dodecylphosphindiyl | methylcyclopenta[b]tellurophenyl | undecyl | heptyl |
| tridecylphosphindiyl | methylcyclopenta[b]pyrrolyl | dodecyl | octyl |
| tetradecylphosphindiyl | methylcyclopenta[b]phospholyl | tridecyl | nonyl |
| pentadecylphosphindiyl | methylcyclopenta[b]arsolyl | tetradecyl | decyl |
| hexadecylphosphindiyl | methylcyclopenta[b]stibolyl | pentadecyl | undecyl |
| heptadecylphosphindiyl | dimethylcyclopenta[b]thienyl | hexadecyl | dodecyl |
| octadecylphosphindiyl | dimethylcyclopenta[b]furanyl | heptadecyl | tridecyl |
| nonadecylphosphindiyl | dimethylcyclopenta[b]pyrrolyl | octadecyl | tetradecyl |
| eicosylphosphindiyl | dimethylcyclopenta[b]phospholyl | nonadecyl | pentadecyl |
| heneicosylphosphindiyl | trimethylcyclopenta[b]thienyl | eicosyl | hexadecyl |
| docosylphosphindiyl | trimethylcyclopenta[b]furanyl | heneicosyl | heptadecyl |
| tricosylphosphindiyl | trimethylcyclopenta[b]pyrrolyl | docosyl | octadecyl |
| tetracosylphosphindiyl | trimethylcyclopenta[b]phospholyl | tricosyl | nonadecyl |
| pentacosylphosphindiyl | tetramethylcyclopenta[b]pyrrolyl | tetracosyl | eicosyl |
| hexacosylphosphindiyl | tetramethylcyclopenta[b]phospholyl | pentacosyl | heneicosyl |
| heptacosylphosphindiyl | ethylcyclopenta[b]thienyl | hexacosyl | docosyl |
| octacosylphosphindiyl | ethylcyclopenta[b]furanyl | heptacosyl | tricosyl |
| nonacosylphosphindiyl | ethylcyclopenta[b]pyrrolyl | octacosyl | tetracosyl |
| triacontylphosphindiyl | ethylcyclopenta[b]phospholyl | nonacosyl | pentacosyl |
| vinylphosphindiyl | diethylcyclopenta[b]thienyl | triacontyl | hexacosyl |
| propenylphosphindiyl | diethylcyclopenta[b]furanyl | vinyl | heptacosyl |
| butenylphosphindiyl | diethylcyclopenta[b]pyrrolyl | propenyl | octacosyl |
| pentenylphosphindiyl | diethylcyclopenta[b]phospholyl | butenyl | nonacosyl |

TABLE 1-continued

| Y | A | $R^1, R^2, R^3, R^4, R^5, R^6, R^7, R^8, R^9, R^{10}, R^{11},$ or $R^{12}$ | X |
|---|---|---|---|
| hexenylphosphindiyl | triethylcyclopenta[b]thienyl | pentenyl | triacontyl |
| heptenylphosphindiyl | triethylcyclopenta[b]furanyl | hexenyl | vinyl |
| octenylphosphindiyl | triethylcyclopenta[b]pyrrolyl | heptenyl | propenyl |
| nonenylphosphindiyl | triethylcyclopenta[b]phospholyl | octenyl | butenyl |
| decenylphosphindiyl | propylcyclopenta[b]thienyl | nonenyl | pentenyl |
| undecenylphosphindiyl | propylcyclopenta[b]furanyl | decenyl | hexenyl |
| dodecenylphosphindiyl | propylcyclopenta[b]pyrrolyl | undecenyl | heptenyl |
| tridecenylphosphindiyl | propylcyclopenta[b]phospholyl | dodecenyl | octenyl |
| tetradecenylphosphindiyl | dipropylcyclopenta[b]thienyl | tridecenyl | nonenyl |
| pentadecenylphosphindiyl | dipropylcyclopenta[b]furanyl | tetradecenyl | decenyl |
| hexadecenylphosphindiyl | dipropylcyclopenta[b]pyrrolyl | pentadecenyl | undecenyl |
| heptadecenylphosphindiyl | dipropylcyclopenta[b]phospholyl | hexadecenyl | dodecenyl |
| octadecenylphosphindiyl | tripropylcyclopenta[b]thienyl | heptadecenyl | tridecenyl |
| nonadecenylphosphindiyl | tripropylcyclopenta[b]furanyl | octadecenyl | tetradecenyl |
| eicosenylphosphindiyl | tripropylcyclopenta[b]pyrrolyl | nonadecenyl | pentadecenyl |
| heneicosenylphosphindiyl | tripropylcyclopenta[b]phospholyl | eicosenyl | hexadecenyl |
| docosenylphosphindiyl | butylcyclopenta[b]thienyl | heneicosenyl | heptadecenyl |
| tricosenylphosphindiyl | butylcyclopenta[b]furanyl | docosenyl | octadecenyl |
| tetracosenylphosphindiyl | butylcyclopenta[b]pyrrolyl | tricosenyl | nonadecenyl |
| pentacosenylphosphindiyl | butylcyclopenta[b]phospholyl | tetracosenyl | eicosenyl |
| hexacosenylphosphindiyl | dibutylcyclopenta[b]thienyl | pentacosenyl | heneicosenyl |
| heptacosenylphosphindiyl | dibutylcyclopenta[b]furanyl | hexacosenyl | docosenyl |
| octacosenylphosphindiyl | dibutylcyclopenta[b]pyrrolyl | heptacosenyl | tricosenyl |
| nonacosenylphosphindiyl | dibutylcyclopenta[b]phospholyl | octacosenyl | tetracosenyl |
| triacontenylphosphindiyl | tributylcyclopenta[b]thienyl | nonacosenyl | pentacosenyl |
| propynylphosphindiyl | tributylcyclopenta[b]furanyl | triacontenyl | hexacosenyl |
| butynylphosphindiyl | tributylcyclopenta[b]pyrrolyl | propynyl | heptacosenyl |
| pentynylphosphindiyl | tributylcyclopenta[b]phospholyl | butynyl | octacosenyl |
| hexynylphosphindiyl | ethylmethylcyclopenta[b]thienyl | pentynyl | nonacosenyl |
| heptynylphosphindiyl | ethylmethylcyclopenta[b]furanyl | hexynyl | triacontenyl |
| octynylphosphindiyl | ethylmethylcyclopenta[b]pyrrolyl | heptynyl | propynyl |
| nonynylphosphindiyl | ethylmethylcyclopenta[b]phospholyl | octynyl | butynyl |
| decynylphosphindiyl | methylpropylcyclopenta[b]thienyl | nonynyl | pentynyl |
| undecynylphosphindiyl | methylpropylcyclopenta[b]furanyl | decynyl | hexynyl |
| dodecynylphosphindiyl | methylpropylcyclopenta[b]pyrrolyl | undecynyl | heptynyl |
| tridecynylphosphindiyl | methylpropylcyclopenta[b]phospholyl | dodecynyl | octynyl |
| tetradecynylphosphindiyl | butylmethylcyclopenta[b]thienyl | tridecynyl | nonynyl |
| pentadecynylphosphindiyl | butylmethylcyclopenta[b]furanyl | tetradecynyl | decynyl |
| hexadecynylphosphindiyl | butylmethylcyclopenta[b]pyrrolyl | pentadecynyl | undecynyl |
| heptadecynylphosphindiyl | butylmethylcyclopenta[b]phospholyl | hexadecynyl | dodecynyl |
| octadecynylphosphindiyl | cyclopenta[c]thienyl | heptadecynyl | tridecynyl |
| nonadecynylphosphindiyl | cyclopenta[c]furanyl | octadecynyl | tetradecynyl |
| eicosynylphosphindiyl | cyclopenta[c]selenophenyl | nonadecynyl | pentadecynyl |
| heneicosynylphosphindiyl | cyclopenta[c]tellurophenyl | eicosynyl | hexadecynyl |
| docosynylphosphindiyl | cyclopenta[c]pyrrolyl | heneicosynyl | heptadecynyl |
| tridecynylphosphindiyl | cyclopenta[c]phospholyl | docosynyl | octadecynyl |
| tetracosynylphosphindiyl | cyclopenta[c]arsolyl | tricosynyl | nonadecynyl |
| pentadecynylphosphindiyl | cyclopenta[c]stibolyl | tetracosynyl | eicosynyl |
| hexadecynylphosphindiyl | methylcyclopenta[c]thienyl | pentacosynyl | heneicosynyl |
| heptadecynylphosphindiyl | methylcyclopenta[c]furanyl | hexacosynyl | docosynyl |
| octadecynylphosphindiyl | methylcyclopenta[c]selenophenyl | heptacosynyl | tricosynyl |
| nonadecynylphosphindiyl | methylcyclopenta[c]tellurophenyl | octacosynyl | tetracosynyl |
| eicosynylphosphindiyl | methylcyclopenta[c]pyrrolyl | nonacosynyl | pentacosynyl |
| heneicosynylphosphindiyl | methylcyclopenta[c]phospholyl | triacontynyl | hexacosynyl |
| docosynylphosphindiyl | methylcyclopenta[c]arsolyl | cyclopropyl | heptacosynyl |
| tricosynylphosphindiyl | methylcyclopenta[c]stibolyl | cyclobutyl | octacosynyl |
| tetracosynylphosphindiyl | dimethylcyclopenta[c]thienyl | cyclopentyl | nonacosynyl |
| pentacosynylphosphindiyl | dimethylcyclopenta[c]furanyl | cyclohexyl | triacontynyl |
| hexacosynylphosphindiyl | dimethylcyclopenta[c]pyrrolyl | cycloheptyl | cyclopropyl |
| heptacosynylphosphindiyl | dimethylcyclopenta[c]phospholyl | cyclooctyl | cyclobutyl |
| octacosynylphosphindiyl | trimethylcyclopenta[c]thienyl | cyclononyl | cyclopentyl |
| nonacosynylphosphindiyl | trimethylcyclopenta[c]furanyl | cyclodecyl | cyclohexyl |
| triacontynylphosphindiyl | trimethylcyclopenta[c]pyrrolyl | cycloundecyl | cycloheptyl |
| cyclopropylphosphindiyl | trimethylcyclopenta[c]phospholyl | cyclododecyl | cyclooctyl |
| cyclobutylphosphindiyl | tetramethylcyclopenta[c]pyrrolyl | cyclotetradecyl | cyclononyl |
| cyclopentylphosphindiyl | tetramethylcyclopenta[c]phospholyl | cyclopentenyl | cyclodecyl |
| cyclohexylphosphindiyl | ethylcyclopenta[c]thienyl | cyclohexenyl | cycloundecyl |
| cycloheptylphosphindiyl | ethylcyclopenta[c]furanyl | cycloheptenyl | cyclododecyl |
| cyclooctylphosphindiyl | ethylcyclopenta[c]pyrrolyl | cyclooctenyl | cyclotetradecyl |
| cyclononylphosphindiyl | ethylcyclopenta[c]phospholyl | cyclodecenyl | cyclopentenyl |
| cyclodecylphosphindiyl | diethylcyclopenta[c]thienyl | cyclododecenyl | cyclohexenyl |
| cycloundecylphosphindiyl | diethylcyclopenta[c]furanyl | methylcyclohexyl | cycloheptenyl |
| cyclododecylphosphindiyl | diethylcyclopenta[c]pyrrolyl | ethylcyclohexyl | cyclooctenyl |
| cyclotetradecylphosphindiyl | diethylcyclopenta[c]phospholyl | propylcyclohexyl | cyclodecenyl |
| cyclohexadecylphosphindiyl | triethylcyclopenta[c]thienyl | dimethylcyclohexyl | cyclododecenyl |
| cyclooctadecylphosphindiyl | triethylcyclopenta[c]furanyl | diethylcyclohexyl | methylcyclohexyl |

TABLE 1-continued

| Y | A | R$^1$, R$^2$, R$^3$, R$^4$, R$^5$, R$^6$, R$^7$, R$^8$, R$^9$, R$^{10}$, R$^{11}$, or R$^{12}$ | X |
|---|---|---|---|
| (methylcyclohexyl)phosphindiyl | triethylcyclopenta[c]pyrrolyl | dipropylcyclohexyl | ethylcyclohexyl |
| (ethylcyclohexyl)phosphindiyl | triethylcyclopenta[c]phospholyl | phenyl | propylcyclohexyl |
| (propylcyclohexyl)phosphindiyl | propylcyclopenta[c]thienyl | tolyl | dimethylcyclohexyl |
| (dimethylcyclohexyl)phosphindiyl | propylcyclopenta[c]furanyl | mesityl | diethylcyclohexyl |
| (diethylcyclohexyl)phosphindiyl | propylcyclopenta[c]pyrrolyl | ethylphenyl | dipropylcyclohexyl |
| (dipropylcyclohexyl)phosphindiyl | propylcyclopenta[c]phospholyl | propylphenyl | phenyl |
| phenylphosphindiyl | dipropylcyclopenta[c]thienyl | butylphenyl | tolyl |
| tolylphosphindiyl | dipropylcyclopenta[c]furanyl | pentylphenyl | mesityl |
| mesitylphosphindiyl | dipropylcyclopenta[c]pyrrolyl | hexylphenyl | ethylphenyl |
| (ethylphenyl)phosphindiyl | dipropylcyclopenta[c]phospholyl | dimethylphenyl | propylphenyl |
| (propylphenyl)phosphindiyl | tripropylcyclopenta[c]thienyl | trimethylphenyl | butylphenyl |
| (butylphenyl)phosphindiyl | tripropylcyclopenta[c]furanyl | diethylphenyl | pentylphenyl |
| (pentylphenyl)phosphindiyl | tripropylcyclopenta[c]pyrrolyl | diethylmethylphenyl | hexylphenyl |
| (hexylphenyl)phosphindiyl | tripropylcyclopenta[c]phospholyl | dipropylphenyl | dimethylphenyl |
| (dimethylphenyl)phosphindiyl | butylcyclopenta[c]thienyl | dipropylmethylphenyl | trimethylphenyl |
| (trimethylphenyl)phosphindiyl | butylcyclopenta[c]furanyl | benzyl | diethylphenyl |
| (diethylphenyl)phosphindiyl | butylcyclopenta[c]pyrrolyl | phenethyl | diethylmethylphenyl |
| (diethylmethylphenyl)phosphindiyl | butylcyclopenta[c]phospholyl | napthyl | dipropylphenyl |
| (dipropylphenyl)phosphindiyl | dibutylcyclopenta[c]thienyl | norbornyl | dipropylmethylphenyl |
| (dipropylmethylphenyl)phosphindiyl | dibutylcyclopenta[c]furanyl | adamantyl | benzyl |
| biphenylphosphindiyl | dibutylcyclopenta[c]pyrrolyl | trifluoromethyl | phenethyl |
| phenethylphosphindiyl | dibutylcyclopenta[c]phospholyl | methyltrifluoromethyl | napthyl |
| napthylphosphindiyl | tributylcyclopenta[c]thienyl | trimethylsilyl | trifluoromethyl |
| norbornylphosphindiyl | tributylcyclopenta[c]furanyl | trimethylgermyl | methoxy |
| adamantylphosphindiyl | tributylcyclopenta[c]pyrrolyl | trimethylsilylmethyl | ethoxy |
| fluoromethylphosphindiyl | tributylcyclopenta[c]phospholyl | trimethylgermylmethyl | propoxy |
| fluoroethylphosphindiyl | ethylmethylcyclopenta[c]thienyl | methoxymethyl | butoxy |
| fluoropropylphosphindiyl | ethylmethylcyclopenta[c]furanyl | ethoxymethyl | dimethylamido |
| fluorobutylphosphindiyl | ethylmethylcyclopenta[c]pyrrolyl | propoxymethyl | diethylamido |
| fluoropentylphosphindiyl | ethylmethylcyclopenta[c]phospholyl | butoxymethyl | methylethylamido |
| fluorohexylphosphindiyl | methylpropylcyclopenta[c]thienyl | phenoxymethyl | phenoxy |
| fluoroheptylphosphindiyl | methylpropylcyclopenta[c]furanyl | methylsulfanyl | benzoxy |
| fluorooctylphosphindiyl | methylpropylcyclopenta[c]pyrrolyl | ethylsulfanyl | allyl |
| fluorononylphosphindiyl | methylpropylcyclopenta[c]phospholyl | propylsulfanyl | 1,1-dimethyl allyl |
| fluorodecylphosphindiyl | butylmethylcyclopenta[c]thienyl | butylsulfanyl | acetylacetonate |
| fluoroundecylphosphindiyl | butylmethylcyclopenta[c]furanyl | phenylsulfanyl | 1,1,1,5,5,5-hexa-fluoroacetylacetonate |
| fluorododecylphosphindiyl | butylmethylcyclopenta[c]pyrrolyl | dimethylaminomethyl | 1,1,1-trifluoro-acetylacetonate |
| thienylphosphindiyl | butylmethylcyclopenta[c]phospholyl | dimethylaminoethyl | 2-carboxymethyl allyl |
| furanylphosphindiyl | indenyl | diphenylaminomethyl | 1,1,1-trifluoro-5,5-di-methylacetylacetonate |
| pyrrolylphosphindiyl | methylindenyl | diphenylaminoethyl | methoxymethyl |
| phospholylphosphindiyl | dimethylindenyl | phenylaminomethyl | ethoxymethyl |
| (methylthienyl)phosphindiyl | trimethylindenyl | phenylaminoethyl | propoxymethyl |
| (methylfuranyl)phosphindiyl | tetramethylindenyl | methylaminomethyl | butoxymethyl |
| (methylpyrrolyl)phosphindiyl | pentamethylindenyl | dimethylphosphinomethyl | phenoxymethyl |
| (methylphospholyl)phosphindiyl | hexamethylindenyl | dimethylphosphinoethyl | methylsulfanyl |
| (propylthienyl)phosphindiyl | ethylindenyl | diphenylphosphinomethyl | ethylsulfanyl |
| (propylfuranyl)phosphindiyl | diethylindenyl | phenylphosphinoethyl | propylsulfanyl |
| (propylpyrrolyl)phosphindiyl | triethylindenyl | methylphosphinoethyl | butylsulfanyl |
| (propylphospholyl)phosphindiyl | propylindenyl | methoxy | phenylsulfanyl |
| (butylthienyl)phosphindiyl | dipropylindenyl | ethoxy | dimethylaminomethyl |
| (butylfuranyl)phosphindiyl | tripropylindenyl | propoxy | dimethylaminoethyl |
| (butylpyrrolyl)phosphindiyl | butylindenyl | butoxy | diphenylaminomethyl |
| (butylphospholyl)phosphindiyl | dibutylindenyl | dimethylamido | phenylaminoethyl |
| (pentylthienyl)phosphindiyl | tributylindenyl | diethylamido | phenylaminomethyl |
| (pentylfuranyl)phosphindiyl | pentylindenyl | methylethylamido | phenylaminoethyl |
| (pentylpyrrolyl)phosphindiyl | dipentylindenyl | phenoxy | methylaminomethyl |
| (penylphospholyl)phosphindiyl | tripentylindenyl | benzoxy | dimethylphosphinomethyl |
| (hexylthienyl)phosphindiyl | hexylindenyl | methylphenoxy | dimethylphosphinoethyl |
| (hexylfuranyl)phosphindiyl | dihexylindenyl | ethylphenoxy | diphenylphosphinomethyl |
| (hexylpyrrolyl)phosphindiyl | trihexylindenyl | propylphenoxy | phenylphosphinoethyl |
| (hexylphospholyl)phosphindiyl | heptylindenyl | dimethylphenoxy | methylphosphinomethyl |
| (heptylthienyl)phosphindiyl | octylindenyl | diethylphenoxy | trimethylsilylmethyl |
| (heptylfuranyl)phosphindiyl | nonylindenyl | dipropylphenoxy | trimethylgermylmethyl |
| (heptylpyrrolyl)phosphindiyl | decylindenyl | methylbenzoxy | trimethylstannylmethyl |
| (heptylphospholyl)phosphindiyl | phenylindenyl | ethylbenzoxy | fluoromethyl |
| (octylthienyl)phosphindiyl | methylphenylindenyl | propylbenzoxy | fluoroethyl |
| (octylfuranyl)phosphindiyl | ethylphenylindenyl | dimethylbenzoxy | fluoropropyl |
| (octylpyrrolyl)phosphindiyl | propylphenylindenyl | diethylbenzoxy | fluorobutyl |
| (octylphospholyl)phosphindiyl | butylphenylindenyl | dipropylbenzoxy | fluoropentyl |
| (nonylthienyl)phosphindiyl | pentylphenylindenyl | perfluoroethyl | fluorohexyl |
| (nonylfuranyl)phosphindiyl | hexylphenylindenyl | perfluoropropyl | fluoroheptyl |
| (nonylpyrrolyl)phosphindiyl | heptylphenylindenyl | perfluorobutyl | fluorooctyl |
| (nonylphospholyl)phosphindiyl | octylphenylindenyl | perfluoropentyl | fluorononyl |

TABLE 1-continued

| Y | A | $R^1, R^2, R^3, R^4, R^5, R^6, R^7, R^8, R^9, R^{10}, R^{11},$ or $R^{12}$ | X |
|---|---|---|---|
| (decylthienyl)phosphindiyl | nonylphenylindenyl | perfluorohexyl | fluorodecyl |
| (decylfuranyl)phosphindiyl | decylphenylindenyl | perfluoroheptyl | fluoroundecyl |
| (decylpyrrolyl)phosphindiyl | dimethylphenylindenyl | perfluorooctyl | fluorododecyl |
| (decylphospholyl)phosphindiyl | trimethylphenylindenyl | perfluorononyl | fluorotridecyl |
| (undecylthienyl)phosphindiyl | dipropylphenylindenyl | perfluorodecyl | fluorotetradecyl |
| (undecylfuranyl)phosphindiyl | methylpropylphenylindenyl | perfluoroundecyl | fluoropentadecyl |
| (undecylpyrrolyl)phosphindiyl | tolylindenyl | perfluorododecyl | fluorohexadecyl |
| (undecylphospholyl)phosphindiyl | methyltolylindenyl | perfluorotridecyl | fluoroheptadecyl |
| (dodecylthienyl)phosphindiyl | ethyltolylindenyl | perfluorotetradecyl | fluorooctadecyl |
| (dodecylfuranyl)phosphindiyl | propyltolylindenyl | perfluoropentadecyl | fluorononadecyl |
| (dodecylpyrrolyl)phosphindiyl | butyltolylindenyl | perfluorohexadecyl | fluoroeicosyl |
| (dodecylphospholyl)phosphindiyl | pentyltolylindenyl | perfluoroheptadecyl | fluorobenzyl |
| (dimethylthienyl)phosphindiyl | hexyltolylindenyl | perfluorooctadecyl | difluorobenzyl |
| (dimethylfuranyl)phosphindiyl | heptyltolylindenyl | perfluorononadecyl | trifluorobenzyl |
| (dimethylpyrrolyl)phosphindiyl | octyltolylindenyl | perfluoroeicosyl | tetrafluorobenzyl |
| (dimethylphospholyl)phosphindiyl | nonyltolylindenyl | fluoromethyl | pentafluorobenzyl |
| (diethylthienyl)phosphindiyl | decyltolylindenyl | fluoroethyl | trifluoromethylbenzyl |
| (diethylfuranyl)phosphindiyl | dimethyltolylindenyl | fluoropropyl | |
| (diethylpyrrolyl)phosphindiyl | trimethyltolylindenyl | fluorobutyl | |
| (diethylphospholyl)phosphindiyl | dipropyltolylindenyl | fluoropentyl | Both X |
| (dipropylthienyl)phosphindiyl | methylpropyltolylindenyl | fluorohexyl | methylidene |
| (dipropylfuranyl)phosphindiyl | naphthylindenyl | fluoroheptyl | ethylidene |
| (dipropylpyrrolyl)phosphindiyl | methylnaphthylindenyl | fluorooctyl | propylidene |
| (dipropylphospholyl)phosphindiyl | ethylnaphthylindenyl | fluorononyl | tetramethylene |
| (dibutylthienyl)phosphindiyl | propylnaphthylindenyl | fluorodecyl | pentamethylene |
| (dibutylfuranyl)phosphindiyl | butylnaphthylindenyl | fluoroundecyl | hexamethylene |
| (dibutylpyrrolyl)phosphindiyl | pentylnaphthylindenyl | fluorododecyl | butadiene |
| (dibutylphospholyl)phosphindiyl | hexylnaphthylindenyl | fluorotridecyl | methylbutadiene |
| fluorophenylphosphindiyl | heptylnaphthylindenyl | fluorotetradecyl | dimethylbutadiene |
| difluorophenylphosphindiyl | octylnaphthylindenyl | fluoropentadecyl | pentadiene |
| trifluorophenylphosphindiyl | nonylnaphthylindenyl | fluorohexadecyl | methylpentadiene |
| tetrafluorophenylphosphindiyl | decylnaphthylindenyl | fluoroheptadecyl | dimethylpentadiene |
| pentafluorophenylphosphindiyl | dimethylnaphthylindenyl | fluorooctadecyl | hexadiene |
| benzylphosphindiyl | trimethylnaphthylindenyl | fluorononadecyl | methylhexadiene |
| trifluoromethylphosphindiyl | dipropylnaphthylindenyl | fluoroeicosyl | dimethylhexadiene |
| trifluoromethylmethylphosphindiyl | methylpropylnaphthylindenyl | thienyl | propandiyl |
| perfluoroethylphosphindiyl | (propylphenyl)indenyl | furanyl | butandiyl |
| perfluoropropylphosphindiyl | methyl(propylphenyl)indenyl | pyrrolyl | pentandiyl |
| perfluorobutylphosphindiyl | ethyl(propylphenyl)indenyl | pholpholyl | hexandiyl |
| perfluoropentylphosphindiyl | propyl(propylphenyl)indenyl | methylthienyl | heptandiyl |
| perfluorohexylphosphindiyl | butyl(propylphenyl)indenyl | methylfuranyl | octandiyl |
| perfluoroheptylphosphindiyl | dimethyl(propylphenyl)indenyl | methylpyrrolyl | nonandiyl |
| perfluorooctylphosphindiyl | trimethyl(propylphenyl)indenyl | methylphospholyl | decandiyl |
| perfluorononylphosphindiyl | methylpropyl(propylphenyl)indenyl | ethylthienyl | dodecandiyl |
| perfluorodecylphosphindiyl | (dipropylphenyl)indenyl | ethylfuranyl | tetradecandiyl |
| perfluoroundecylphosphindiyl | methyl(dipropylphenyl)indenyl | ethylpyrrolyl | hexadecandiyl |
| perfluorododecylphosphindiyl | ethyl(dipropylphenyl)indenyl | ethylphospholyl | octadecandiyl |
| trimethylsilylmethylphosphindiyl | propyl(dipropylphenyl)indenyl | propylthienyl | azapropandiyl |
| trimethylgermylmethylphosphindiyl | butyl(dipropylphenyl)indenyl | propylfuranyl | azabutandiyl |
| methoxymethylphosphindiyl | dimethyl(dipropylphenyl)indenyl | propylpyrrolyl | azapentandiyl |
| ethoxymethylphosphindiyl | trimethyl(dipropylphenyl)indenyl | propylphospholyl | azahexandiyl |
| propoxymethylphosphindiyl | methylpropyl(dipropylphenyl)indenyl | butylthienyl | azaheptandiyl |
| butoxymethylphosphindiyl | (dimethylphenyl)indenyl | butylfuranyl | azaoctandiyl |
| phenoxymethylphosphindiyl | methyl(dimethylphenyl)indenyl | butylpyrrolyl | azanonandiyl |
| dimethylaminomethylphosphindiyl | ethyl(dimethylphenyl)indenyl | butylphospholyl | azadecandiyl |
| diphenylaminomethylphosphindiyl | propyl(dimethylphenyl)indenyl | pentylthienyl | azadodecandiyl |
| diphenylphosphinomethylphosphindiyl | butyl(dimethylphenyl)indenyl | pentylfuranyl | phosphapropandiyl |
| fluorobenzylphosphindiyl | trimethyl(dimethylphenyl)indenyl | pentylpyrrolyl | phosphabutandiyl |
| difluorobenzylphosphindiyl | trimethyl(dimethylphenyl)indenyl | penylphospholyl | phosphapentandiyl |
| trifluorobenzylphosphindiyl | methylpropyl(dimethylphenyl)indenyl | hexylthienyl | thiapropandiyl |
| tetrafluorobenzylphosphindiyl | (trimethylphenyl)indenyl | hexylfuranyl | thiabutandiyl |
| pentafluorobenzylphosphindiyl | methyl(trimethylphenyl)indenyl | hexylpyrrolyl | thiapentandiyl |
| trifluoromethylbenzylphosphindiyl | ethyl(trimethylphenyl)indenyl | hexylphospholyl | catecholate |
| 1,2-dimethyldiphosphandiyl | propyl(trimethylphenyl)indenyl | heptylthienyl | butylcatecholate |
| 1,2-diethyldiphosphandiyl | butyl(trimethylphenyl)indenyl | heptylfuranyl | diazabutandiyl |
| 1,2-dipropyldiphosphandiyl | dimethyl(trimethylphenyl)indenyl | heptylpyrrolyl | diazapentandiyl |
| 1,2-dibutyldiphosphandiyl | trimethyl(trimethylphenyl)indenyl | heptylphospholyl | diazahexandiyl |
| 1,2-dipentyldiphosphandiyl | methylpropyl(trimethylphenyl)indenyl | octylthienyl | dioxabutandiyl |
| 1,2-dihexyldiphosphandiyl | trimethylsilylindenyl | octylfuranyl | dioxapentandiyl |
| 1,2-diheptyldiphosphandiyl | trifluormethylindenyl | octylpyrrolyl | dioxahexandiyl |
| 1,2-dioctyldiphosphandiyl | trifluoromethylphenylindenyl | octylphospholyl | |
| 1,2-dinonyldiphosphandiyl | (benzothiophenyl)indenyl | nonylthienyl | |
| 1,2-didecyldiphosphandiyl | (benzofuranyl)indenyl | nonylfuranyl | |
| 1,2-diundecyldiphosphandiyl | (fluorophenyl)indenyl | nonylpyrrolyl | |
| 1,2-didodecyldiphosphandiyl | (difluorophenyl)indenyl | nonylphospholyl | |
| 1,2-ditridecyldiphosphandiyl | (trifluorophenyl)indenyl | decylthienyl | |

TABLE 1-continued

| Y | A | R¹, R², R³, R⁴, R⁵, R⁶, R⁷, R⁸, R⁹, R¹⁰, R¹¹, or R¹² | X |
|---|---|---|---|
| 1,2-ditetradecyldiphosphandiyl | (tetrafluorophenyl)indenyl | decylfuranyl | |
| 1,2-dipentadecyldiphosphandiyl | (pentafluorophenyl)indenyl | decylpyrrolyl | |
| 1,2-dihexadecyldiphosphandiyl | (trifluoromethylphenyl)indenyl | decylphospholyl | |
| 1,2-diheptadecyldiphosphandiyl | (thienyl)indenyl | undecylthienyl | |
| 1,2-dioctadecyldiphosphandiyl | (furanyl)indenyl | undecylfuranyl | |
| 1,2-dinonadecyldiphosphandiyl | (pyrrolyl)indenyl | undecylpyrrolyl | |
| 1,2-dieicosyldiphosphandiyl | (phospholyl)indenyl | undecylphospholyl | |
| 1,2-diheneicosyldiphosphandiyl | (methylthienyl)indenyl | dodecylthienyl | |
| 1,2-didocosyldiphosphandiyl | (methylfuranyl)indenyl | dodecylfuranyl | |
| 1,2-ditricosyldiphosphandiyl | (methylpyrrolyl)indenyl | dodecylpyrrolyl | |
| 1,2-ditetracosyldiphosphandiyl | (methylphospholyl)indenyl | dodecylphospholyl | |
| 1,2-dipentacosyldiphosphandiyl | (dimethylthienyl)indenyl | dimethylthienyl | |
| 1,2-dihexacosyldiphosphandiyl | (dimethylfuranyl)indenyl | dimethylfuranyl | |
| 1,2-diheptacosyldiphosphandiyl | (dimethylpyrrolyl)indenyl | dimethylpyrrolyl | |
| 1,2-dioctacosyldiphosphandiyl | (dimethylphospholyl)indenyl | dimethylphospholyl | |
| 1,2-dinonacosyldiphosphandiyl | (ethylthienyl)indenyl | diethylthienyl | |
| 1,2-ditriacontyldiphosphandiyl | (ethylfuranyl)indenyl | diethylfuranyl | |
| 1,2-divinyldiphosphandiyl | (ethylpyrrolyl)indenyl | diethylpyrrolyl | |
| 1,2-dipropenyldiphosphandiyl | (ethylphospholyl)indenyl | diethylphospholyl | |
| 1,2-dibutenyldiphosphandiyl | (propylthienyl)indenyl | dipropylthienyl | |
| 1,2-dipentenyldiphosphandiyl | (propylfuranyl)indenyl | dipropylfuranyl | |
| 1,2-dihexenyldiphosphandiyl | (propylpyrrolyl)indenyl | dipropylpyrrolyl | |
| 1,2-diheptenyldiphosphandiyl | (propylphospholyl)indenyl | dipropylphospholyl | |
| 1,2-dioctenyldiphosphandiyl | (butylthienyl)indenyl | dibutylthienyl | |
| 1,2-dinonenyldiphosphandiyl | (butylfuranyl)indenyl | dibutylfuranyl | |
| 1,2-didecenyldiphosphandiyl | (butylpyrrolyl)indenyl | dibutylpyrrolyl | |
| 1,2-diundecenyldiphosphandiyl | (butylphospholyl)indenyl | dibutylphospholyl | |
| 1,2-didodecenyldiphosphandiyl | methyl(benzothipheneyl)indenyl | dipentylthienyl | |
| 1,2-dipropynyldiphosphandiyl | methyl(benzofuranyl)indenyl | dipentylfuranyl | |
| 1,2-dibutynyldiphosphandiyl | methyl(fluorophenyl)indenyl | dipentylpyrrolyl | |
| 1,2-dipentynyldiphosphandiyl | methyl(difluorophenyl)indenyl | dipenylphospholyl | |
| 1,2-dihexynyldiphosphandiyl | methyl(trifluorophenyl)indenyl | dihexylthienyl | |
| 1,2-diheptynyldiphosphandiyl | methyl(tetrafluorophenyl)indenyl | dihexylfuranyl | |
| 1,2-dioctynyldiphosphandiyl | methyl(pentafluorophenyl)indenyl | dihexylpyrrolyl | |
| 1,2-dinonynyldiphosphandiyl | methyl(trifluoromethylphenyl)indenyl | dihexylphospholyl | |
| 1,2-didecynyldiphosphandiyl | methyl(thienyl)indenyl | trimethylthienyl | |
| 1,2-diundecynyldiphosphandiyl | methyl(furanyl)indenyl | trimethylfuranyl | |
| 1,2-didodecynyldiphosphandiyl | methyl(pyrrolyl)indenyl | trimethylpyrrolyl | |
| 1,2-dicyclopropyldiphosphandiyl | methyl(phospholyl)indenyl | trimethylphospholyl | |
| 1,2-dicyclobutyldiphosphandiyl | methyl(methylthienyl)indenyl | benzothipheneyl | |
| 1,2-dicyclopentyldiphosphandiyl | methyl(methylfuranyl)indenyl | benzofuranyl | |
| 1,2-dicyclohexyldiphosphandiyl | methyl(methylpyrrolyl)indenyl | phenylthienyl | |
| 1,2-dicycloheptyldiphosphandiyl | methyl(methylphospholyl)indenyl | phenylfuranyl | |
| 1,2-dicyclooctyldiphosphandiyl | methyl(dimethylthienyl)indenyl | phenylpyrrolyl | |
| 1,2-dicyclononyldiphosphandiyl | methyl(dimethylfuranyl)indenyl | phenylphospholyl | |
| 1,2-dicyclodecyldiphosphandiyl | methyl(dimethylpyrrolyl)indenyl | tolylthienyl | |
| 1,2-diphenyldiphosphandiyl | methyl(dimethylphospholyl)indenyl | tolylfuranyl | |
| 1,2-ditolyldiphosphandiyl | methyl(ethylthienyl)indenyl | tolylpyrrolyl | |
| 1,2-dimesityldiphosphandiyl | methyl(ethylfuranyl)indenyl | tolylphospholyl | |
| 1,2-di(ethylphenyl)diphosphandiyl | methyl(ethylpyrrolyl)indenyl | mesitylthienyl | |
| 1,2-di(propylphenyl)diphosphandiyl | methyl(ethylphospholyl)indenyl | mesitylfuranyl | |
| 1,2-di(butylphenyl)diphosphandiyl | methyl(propylthienyl)indenyl | mesitylpyrrolyl | |
| 1,2-di(pentylphenyl)diphosphandiyl | methyl(propylfuranyl)indenyl | mesitylphospholyl | |
| 1,2-di(hexylphenyl)diphosphandiyl | methyl(propylpyrrolyl)indenyl | fluorophenyl | |
| 1,2-di(dimethylphenyl)diphosphandiyl | methyl(propylphospholyl)indenyl | difluorophenyl | |
| 1,2-di(trimethylphenyl)diphosphandiyl | methyl(butylthienyl)indenyl | trifluorophenyl | |
| 1,2-dibiphenyldiphosphandiyl | methyl(butylfuranyl)indenyl | tetrafluorophenyl | |
| 1,2-diphenethyldiphosphandiyl | methyl(butylpyrrolyl)indenyl | pentafluorophenyl | |
| 1,2-dinapthyldiphosphandiyl | methyl(butylphospholyl)indenyl | trifluoromethylphenyl | |
| 1,2-dinorbornyldiphosphandiyl | propyl(benzothipheneyl)indenyl | fluorobenzyl | |
| 1,2-diadamantyldiphosphandiyl | propyl(benzofuranyl)indenyl | difluorobenzyl | |
| 1,2-di(fluoromethyl)diphosphandiyl | propyl(fluorophenyl)indenyl | trifluorobenzyl | |
| 1,2-di(fluoroethyl)diphosphandiyl | propyl(difluorophenyl)indenyl | tetrafluorobenzyl | |
| 1,2-di(fluoropropyl)diphosphandiyl | propyl(trifluorophenyl)indenyl | pentafluorobenzyl | |
| 1,2-di(fluorobutyl)diphosphandiyl | propyl(tetrafluorophenyl)indenyl | trifluoromethylbenzyl | |
| 1,2-di(fluoropentyl)diphosphandiyl | propyl(pentafluorophenyl)indenyl | | |
| 1,2-di(fluorohexyl)diphosphandiyl | propyl(trifluoromethylphenyl)indenyl | | |
| 1,2-dithienyldiphosphandiyl | propyl(thienyl)indenyl | | |
| 1,2-difuranyldiphosphandiyl | propyl(furanyl)indenyl | | |
| 1,2-dipyrrolyldiphosphandiyl | propyl(pyrrolyl)indenyl | | |
| 1,2-diphospholyldiphosphandiyl | propyl(phospholyl)indenyl | | |
| 1,2-di(methylthienyl)diphosphandiyl | propyl(methylthienyl)indenyl | | |
| 1,2-di(methylfuranyl)diphosphandiyl | propyl(methylfuranyl)indenyl | | |
| 1,2-di(methylpyrrolyl)diphosphandiyl | propyl(methylpyrrolyl)indenyl | | |
| 1,2-di(methylphospholyl)diphosphandiyl | propyl(methylphospholyl)indenyl | | |
| 1,2-di(fluorophenyl)diphosphandiyl | propyl(dimethylthienyl)indenyl | | |

TABLE 1-continued

| Y | A | $R^1, R^2, R^3, R^4, R^5, R^6, R^7,$ $R^8, R^9, R^{10}, R^{11}, \text{ or } R^{12}$ | X |
|---|---|---|---|
| 1,2-di(difluorophenyl)diphosphandiyl | propyl(dimethylfuranyl)indenyl | | |
| 1,2-di(trifluorophenyl)diphosphandiyl | propyl(dimethylpyrrolyl)indenyl | | |
| 1,2-di(tetrafluorophenyl)diphosphandiyl | propyl(dimethylphospholyl)indenyl | | |
| 1,2-di(pentafluorophenyl)diphosphandiyl | propyl(ethylthienyl)indenyl | | |
| 1,2-dibenzyldiphosphandiyl | propyl(ethylfuranyl)indenyl | | |
| 1,2-di(trifluoromethyl)diphosphandiyl | propyl(ethylpyrrolyl)indenyl | | |
| | propyl(ethylphospholyl)indenyl | | |
| 1-methyl-2-phenyldiphosphandiyl | propyl(propylthienyl)indenyl | | |
| 1-ethyl-2-phenyldiphosphandiyl | propyl(propylfuranyl)indenyl | | |
| 1-propyl-2-phenyldiphosphandiyl | propyl(propylpyrrolyl)indenyl | | |
| 1-butyl-2-phenyldiphosphandiyl | propyl(propylphospholyl)indenyl | | |
| 1-pentyl-2-phenyldiphosphandiyl | propyl(butylthienyl)indenyl | | |
| 1-hexyl-2-phenyldiphosphandiyl | propyl(butylfuranyl)indenyl | | |
| 1-heptyl-2-phenyldiphosphandiyl | propyl(butylpyrrolyl)indenyl | | |
| 1-octyl-2-phenyldiphosphandiyl | propyl(butylphospholyl)indenyl | | |
| 1-nonyl-2-phenyldiphosphandiyl | tetrahydroindenyl | | |
| 1-decyl-2-phenyldiphosphandiyl | methyltetrahydroindenyl | | |
| 1-methyl-2-tolyldiphosphandiyl | dimethyltetrahydroindenyl | | |
| 1-ethyl-2-tolyldiphosphandiyl | trimethyltetrahydroindenyl | | |
| 1-propyl-2-tolyldiphosphandiyl | tetramethyltetrahydroindenyl | | |
| 1-butyl-2-tolyldiphosphandiyl | pentamethyltetrahydroindenyl | | |
| 1-pentyl-2-tolyldiphosphandiyl | hexamethyltetrahydroindenyl | | |
| 1-hexyl-2-tolyldiphosphandiyl | ethyltetrahydroindenyl | | |
| 1-heptyl-2-tolyldiphosphandiyl | propyltetrahydroindenyl | | |
| 1-octyl-2-tolyldiphosphandiyl | butyltetrahydroindenyl | | |
| 1-nonyl-2-tolyldiphosphandiyl | pentyltetrahydroindenyl | | |
| 1-decyl-2-tolyldiphosphandiyl | hexyltetrahydroindenyl | | |
| 1-methyl-2-ethyldiphosphandiyl | heptyltetrahydroindenyl | | |
| 1-methyl-2-propyldiphosphandiyl | octyltetrahydroindenyl | | |
| 1-methyl-2-butyldiphosphandiyl | nonyltetrahydroindenyl | | |
| 1-methyl-2-pentyldiphosphandiyl | decyltetrahydroindenyl | | |
| 1-methyl-hexyldiphosphandiyl | phenyltetrahydroindenyl | | |
| 1-methyl-2-heptyldiphosphandiyl | methylphenyltetrahydroindenyl | | |
| 1-methyl-2-octyldiphosphandiyl | ethylphenyltetrahydroindenyl | | |
| 1-methyl-2-nonyldiphosphandiyl | propylphenyltetrahydroindenyl | | |
| 1-methyl-2-decyldiphosphandiyl | butylphenyltetrahydroindenyl | | |
| 1-ethyl-2-propyldiphosphandiyl | pentylphenyltetrahydroindenyl | | |
| 1-ethyl-2-butyldiphosphandiyl | hexylphenyltetrahydroindenyl | | |
| 1-ethyl-2-pentyldiphosphandiyl | heptylphenyltetrahydroindenyl | | |
| 1-ethyl-2-hexyldiphosphandiyl | octylphenyltetrahydroindenyl | | |
| 1-ethyl-2-heptyldiphosphandiyl | nonylphenyltetrahydroindenyl | | |
| 1-ethyl-2-octyldiphosphandiyl | decylphenyltetrahydroindenyl | | |
| 1-ethyl-2-nonyldiphosphandiyl | dimethylphenyltetrahydroindenyl | | |
| 1-ethyl-2-decyldiphosphandiyl | trimethylphenyltetrahydroindenyl | | |
| 1-propyl-2-butyldiphosphandiyl | dipropylphenyltetrahydroindenyl | | |
| 1-propyl-2-penyldiphosphandiyl | methylpropylphenyltetrahydroindenyl | | |
| 1-propyl-2-hexyldiphosphandiyl | tolyltetrahydroindenyl | | |
| 1-propyl-2-heptyldiphosphandiyl | methyltolyltetrahydroindenyl | | |
| 1-propyl-2-octyldiphosphandiyl | ethyltolyltetrahydroindenyl | | |
| 1-propyl-2-nonyldiphosphandiyl | propyltolyltetrahydroindenyl | | |
| 1-propyl-2-decyldiphosphandiyl | butyltolyltetrahydroindenyl | | |
| 1-butyl-2-pentyldiphosphandiyl | dimethyltolyltetrahydroindenyl | | |
| 1-butyl-2-hexyldiphosphandiyl | trimethyltolyltetrahydroindenyl | | |
| 1-butyl-2-heptyldiphosphandiyl | dipropyltolyltetrahydroindenyl | | |
| 1-butyl-2-octyldiphosphandiyl | methylpropyltolyltetrahydroindenyl | | |
| 1-butyl-2-nonyldiphosphandiyl | naphthyltetrahydroindenyl | | |
| 1-butyl-2-dectkdiphosphandiyl | methylnaphthyltetrahydroindenyl | | |
| 1-pentyl-2-hexyldiphosphandiyl | ethylnaphthyltetrahydroindenyl | | |
| 1-pentyl-2-heptyldiphosphandiyl | propylnaphthyltetrahydroindenyl | | |
| 1-pentyl-2-octyldiphosphandiyl | butylnaphthyltetrahydroindenyl | | |
| 1-pentyl-2-nonyldiphosphandiyl | dimethylnaphthyltetrahydroindenyl | | |
| 1-pentyl-2-decyldiphosphandiyl | trimethylnaphthyltetrahydroindenyl | | |
| 1-hexyl-2-heptyldiphosphandiyl | dipropylnaphthyltetrahydroindenyl | | |
| 1-hexyl-2-octyldiphosphandiyl | methylpropylnaphthyltetrahydroindenyl | | |
| 1-hexyl-2-nonyldiphosphandiyl | (propylphenyl)tetrahydroindenyl | | |
| 1-hexyl-2-decyldiphosphandiyl | methyl(propylphenyl)tetrahydroindenyl | | |
| 1-heptyl-2-octyldiphosphandiyl | ethyl(propylphenyl)tetrahydroindenyl | | |
| 1-heptyl-2-octyldiphosphandiyl | propyl(propylphenyl)tetrahydroindenyl | | |
| 1-heptyl-2-nonyldiphosphandiyl | butyl(propylphenyl)tetrahydroindenyl | | |
| 1-heptyl-2-decyldiphosphandiyl | dimethyl(propylphenyl)tetrahydroindenyl | | |
| 1-octyl-2-nonyldiphosphandiyl | trimethyl(propylphenyl)tetrahydroindenyl | | |
| 1-octyl-2-decyldiphosphandiyl | methylpropyl(propylphenyl)tetrahydroindenyl | | |
| 1-nonyl-2-decyldiphosphandiyl | (dipropylphenyl)tetrahydroindenyl | | |
| | methyl(dipropylphenyl)tetrahydroindenyl | | |
| | ethyl(dipropylphenyl)tetrahydroindenyl | | |
| | propyl(dipropylphenyl)tetrahydroindenyl | | |

TABLE 1-continued

| Y | A | $R^1, R^2, R^3, R^4, R^5, R^6, R^7,$ $R^8, R^9, R^{10}, R^{11},$ or $R^{12}$ | X |
|---|---|---|---|
| | butyl(dipropylphenyl)tetrahydroindenyl | | |
| | dimethyl(dipropylphenyl)tetrahydroindenyl | | |
| | trimethyl(dipropylphenyl)tetrahydroindenyl | | |
| | methylpropyl(dipropylphenyl)tetrahydroindenyl | | |
| | (dimethylphenyl)tetrahydroindenyl | | |
| | methyl(dimethylphenyl)tetrahydroindenyl | | |
| | ethyl(dimethylphenyl)tetrahydroindenyl | | |
| | propyl(dimethylphenyl)tetrahydroindenyl | | |
| | butyl(dimethylphenyl)tetrahydroindenyl | | |
| | trimethyl(dimethylphenyl)tetrahydroindenyl | | |
| | trimethyl(dimethylphenyl)tetrahydroindenyl | | |
| | methylpropyl(dimethylphenyl)tetrahydroindenyl | | |
| | (trimethylphenyl)tetrahydroindenyl | | |
| | methyl(trimethylphenyl)tetrahydroindenyl | | |
| | ethyl(trimethylphenyl)tetrahydroindenyl | | |
| | propyl(trimethylphenyl)tetrahydroindenyl | | |
| | butyl(trimethylphenyl)tetrahydroindenyl | | |
| | dimethyl(trimethylphenyl)tetrahydroindenyl | | |
| | trimethyl(trimethylphenyl)tetrahydroindenyl | | |
| | methylpropyl(trimethylphenyl)tetrahydroindenyl | | |
| | cyclopentadienyl | | |
| | methylcyclopentadienyl | | |
| | dimethylcyclopentadienyl | | |
| | trimethylcyclopentadienyl | | |
| | tetramethylcyclopentadienyl | | |
| | ethylcyclopentadienyl | | |
| | diethylcyclopentadienyl | | |
| | triethylcyclopentadienyl | | |
| | tetraethylcyclopentadienyl | | |
| | propylcyclopentadienyl | | |
| | dipropylcyclopentadienyl | | |
| | tripropylcyclopentadienyl | | |
| | tetrapropylcyclopentadienyl | | |
| | butylcyclopentadienyl | | |
| | dibutylcyclopentadienyl | | |
| | tributylcyclopentadienyl | | |
| | tetrabutylcyclopentadienly | | |
| | pentylcyclopentadienyl | | |
| | dipentylcyclopentadienyl | | |
| | tripentylcyclopentadienyl | | |
| | tetrapentylcyclopentadienyl | | |
| | hexylcyclopentadienyl | | |
| | dihexylcyclopentadienyl | | |
| | trihexylcyclopentadienyl | | |
| | tetrahexylcyclopentadienyl | | |
| | heptylcyclopentadienyl | | |
| | diheptylcyclopentadienyl | | |
| | octylcyclopentadienyl | | |
| | dioctylcyclopentadienyl | | |
| | nonylcyclopentadienyl | | |
| | dinonylcyclopentadienyl | | |
| | decylcyclopentadienyl | | |
| | didecylcyclopentadienyl | | |
| | undecylcyclopentadienyl | | |
| | dodecylcyclopentadienyl | | |
| | tridecylcyclopentadienyl | | |
| | tetradecylcyclopentadienyl | | |
| | pentadecylcyclopentadienyl | | |
| | hexadecylcyclopentadienyl | | |
| | heptadecylcyclopentadienyl | | |
| | octadecylcyclopentadienyl | | |
| | nonadecylcyclopentadienyl | | |
| | eicosylcyclopentadienyl | | |
| | heneicosylcyclopentadienyl | | |
| | docosylcyclopentadienyl | | |
| | tricosylcyclopentadienyl | | |
| | tetracosylcyclopentadienyl | | |
| | pentacosylcyclopentadienyl | | |
| | hexacosylcyclopentadienyl | | |
| | heptacosylcyclopentadienyl | | |
| | octacosylcyclopentadienyl | | |
| | nonacosylcyclopentadienyl | | |
| | triacontylcyclopentadienyl | | |
| | vinylcyclopentadienyl | | |
| | allylcyclopentadienyl | | |
| | propenylcyclopentadienyl | | |

TABLE 1-continued

| Y | A | R¹, R², R³, R⁴, R⁵, R⁶, R⁷, R⁸, R⁹, R¹⁰, R¹¹, or R¹² | X |
|---|---|---|---|
| | butenylcyclopentadienyl | | |
| | propynylcyclopentadienyl | | |
| | butynylcyclopentadienyl | | |
| | cyclopropylcyclopentadienyl | | |
| | cyclobutylcyclopentadienyl | | |
| | cyclopentylcyclopentadienyl | | |
| | cyclohexylcyclopentadienyl | | |
| | phenylcyclopentadienyl | | |
| | (dimethylphenyl)cyclopentadienyl | | |
| | tolylcyclopentadienyl | | |
| | benzylcyclopentadienyl | | |
| | phenethylcyclopentadienyl | | |
| | trimethylsilylcyclopentadienyl | | |
| | trimethylgermylcyclopentadienyl | | |
| | triethylsilylcyclopentadienyl | | |
| | dimethylethylsilylcyclopentadienyl | | |
| | biphenylcyclopentadienyl | | |
| | pyrenylcyclopentadienyl | | |
| | trifluoromethylcyclopentadienyl | | |
| | trifluoromethylmethylcyclopentadienyl | | |
| | norbornylcyclopentadienyl | | |
| | methylethylcyclopentadienyl | | |
| | methylpropylcyclopentadienyl | | |
| | methylbutylylcyclopentadienyl | | |
| | methylphenylcyclopentadienyl | | |
| | methylcyclohexylcylopentadienyl | | |
| | methyltolylcyclopentadienyl | | |
| | trimethylsilylmethylcylopentadienyl | | |
| | methylbenzylcylopentadienyl | | |
| | methylphenethylcylopentadienyl | | |
| | methylvinylcylopentadienyl | | |
| | methylallylcylopentadienyl | | |
| | (benzothiopheneyl)cyclopentadienyl | | |
| | (benzofuranyl)cyclopentadienyl | | |
| | (fluorophenyl)cyclopentadienyl | | |
| | (difluorophenyl)cyclopentadienyl | | |
| | (trifluorophenyl)cyclopentadienyl | | |
| | (tetrafluorophenyl)cyclopentadienyl | | |
| | (pentafluorophenyl)cyclopentadienyl | | |
| | (trifluoromethylphenyl)cyclopentadienyl | | |
| | (thienyl)cyclopentadienyl | | |
| | (furanyl)cyclopentadienyl | | |
| | (pyrrolyl)cyclopentadienyl | | |
| | (phospholyl)cyclopentadienyl | | |
| | (methylthienyl)cyclopentadienyl | | |
| | (methylfuranyl)cyclopentadienyl | | |
| | (methylpyrrolyl)cyclopentadienyl | | |
| | (methylphospholyl)cyclopentadienyl | | |
| | (dimethylthienyl)cyclopentadienyl | | |
| | (dimethylfuranyl)cyclopentadienyl | | |
| | (dimethylpyrrolyl)cyclopentadienyl | | |
| | (dimethylphospholyl)cyclopentadienyl | | |
| | methyl(benzothiopheneyl)cyclopentadienyl | | |
| | methyl(benzofuranyl)cyclopentadienyl | | |
| | methyl(fluorophenyl)cyclopentadienyl | | |
| | methyl(difluorophenyl)cyclopentadienyl | | |
| | methyl(trifluorophenyl)cyclopentadienyl | | |
| | methyl(tetrafluorophenyl)cyclopentadienyl | | |
| | methyl(pentafluorophenyl)cyclopentadienyl | | |
| | methyl(trifluoromethylphenyl)cyclopenta-dienyl | | |
| | methyl(thienyl)cyclopentadienyl | | |
| | methyl(furanyl)cyclopentadienyl | | |
| | methyl(pyrrolyl)cyclopentadienyl | | |
| | methyl(phospholyl)cyclopentadienyl | | |
| | methyl(methylthienyl)cyclopentadienyl | | |
| | methyl(methylfuranyl)cyclopentadienyl | | |
| | methyl(methylpyrrolyl)cyclopentadienyl | | |
| | methyl(methylphospholyl)cyclopentadienyl | | |
| | methyl(dimethylthienyl)cyclopentadienyl | | |
| | methyl(dimethylfuranyl)cyclopentadienyl | | |
| | methyl(dimethylpyrrolyl)cyclopentadienyl | | |
| | methyl(dimethylphospholyl)cyclopentadienyl | | |
| | fluorenyl | | |
| | methylfluorenyl | | |
| | dimethylfluorenyl | | |
| | trimethylfluorenyl | | |

TABLE 1-continued

| Y | A | R¹, R², R³, R⁴, R⁵, R⁶, R⁷, R⁸, R⁹, R¹⁰, R¹¹, or R¹² | X |
|---|---|---|---|
| | tetramethylfluorenyl | | |
| | ethylfluorenyl | | |
| | diethylfluorenyl | | |
| | triethylfluorenyl | | |
| | tetraethylfluorenyl | | |
| | propylfluorenyl | | |
| | dipropylfluorenyl | | |
| | tripropylfluorenyl | | |
| | tetrapropylfluorenyl | | |
| | butylfluorenyl | | |
| | dibutylfluorenyl | | |
| | tributylfluorenyl | | |
| | tetrabutylfluorenyl | | |
| | pentylfluorenyl | | |
| | dipentylfluorenyl | | |
| | tripentylfluorenyl | | |
| | tetrapentylfluorenyl | | |
| | hexylfluorenyl | | |
| | dihexylfluorenyl | | |
| | trihexylfluorenyl | | |
| | tetrahexylfluorenyl | | |
| | heptylfluorenyl | | |
| | diheptylfluorenyl | | |
| | octylfluorenyl | | |
| | dioctylfluorenyl | | |
| | nonylfluorenyl | | |
| | dinonylfluorenyl | | |
| | decylfluorenyl | | |
| | didecylfluorenyl | | |
| | dodecylfluorenyl | | |
| | didodecylfluorenyl | | |
| | trifluoromethylfluorenyl | | |
| | bis(trifluoromethyl)fluorenyl | | |
| | trimethylsilylfluorenyl | | |
| | bis(trimethylsilyl)fluorenyl | | |
| | cyclohexylfluorenyl | | |
| | bis(cyclohexyl)fluorenyl | | |
| | phenylfluorenyl | | |
| | diphenylfluorenyl | | |
| | tolylfluorenyl | | |
| | bis(tolyl)fluorenyl | | |
| | octahydrofluorenyl | | |
| | methyloctahydrofluorenyl | | |
| | dimethyloctahydrofluorenyl | | |
| | trimethyloctahydrofluorenyl | | |
| | tetramethyloctahydrofluorenyl | | |
| | ethyloctahydrofluorenyl | | |
| | diethyloctahydrofluorenyl | | |
| | propyloctahydrofluorenyl | | |
| | dipropyloctahydrofluorenyl | | |
| | butyloctahydrofluorenyl | | |
| | dibutyloctahydrofluorenyl | | |
| | pentyloctahydrofluorenyl | | |
| | dipentyloctahydrofluorenyl | | |
| | hexyloctahydrofluorenyl | | |
| | dihexyloctahydrofluorenyl | | |
| | heptyloctahydrofluorenyl | | |
| | diheptyloctahydrofluorenyl | | |
| | octyloctahydrofluorenyl | | |
| | dioctyloctahydrofluorenyl | | |
| | methyloctahydrodibenzyl[b,h]fluorenyl | | |
| | dimethyloctahydrodibenzyl[b,h]fluorenyl | | |
| | trimethyloctahydrodibenzyl[b,h]fluorenyl | | |
| | tetramethyloctahydrodibenzyl[b,h]fluorenyl | | |
| | pentamethyloctahydrodibenzyl[b,h]fluorenyl | | |
| | hexamethyloctahydrodibenzyl[b,h]fluorenyl | | |
| | heptamethyloctahydrodibenzyl[b,h]fluorenyl | | |
| | octamethyloctahydrodibenzyl[b,h]fluorenyl | | |
| | (benzothipheneyl)fluorenyl | | |
| | (benzofuranyl)fluorenyl | | |
| | (fluorophenyl)fluorenyl | | |
| | (difluorophenyl)fluorenyl | | |
| | (trifluorophenyl)fluorenyl | | |
| | (tetrafluorophenyl)fluorenyl | | |
| | (pentafluorophenyl)fluorenyl | | |
| | (trifluoromethylphenyl)fluorenyl | | |

TABLE 1-continued

| Y | A | $R^1, R^2, R^3, R^4, R^5, R^6, R^7,$ $R^8, R^9, R^{10}, R^{11},$ or $R^{12}$ | X |
|---|---|---|---|
| | (thienyl)fluorenyl | | |
| | (furanyl)fluorenyl | | |
| | (pyrrolyl)fluorenyl | | |
| | (phospholyl)fluorenyl | | |
| | (methylthienyl)fluorenyl | | |
| | (methylfuranyl)fluorenyl | | |
| | (methylpyrrolyl)fluorenyl | | |
| | (methylphospholyl)fluorenyl | | |
| | (dimethylthienyl)fluorenyl | | |
| | (dimethylfuranyl)fluorenyl | | |
| | (dimethylpyrrolyl)fluorenyl | | |
| | (dimethylphospholyl)fluorenyl | | |
| | bis(benzothiopheneyl)fluorenyl | | |
| | bis(benzofuranyl)fluorenyl | | |
| | bis(fluorophenyl)fluorenyl | | |
| | bis(difluorophenyl)fluorenyl | | |
| | bis(trifluorophenyl)fluorenyl | | |
| | bis(tetrafluorophenyl)fluorenyl | | |
| | bis(pentafluorophenyl)fluorenyl | | |
| | bis(trifluoromethylphenyl)fluorenyl | | |
| | bis(thienyl)fluorenyl | | |
| | bis(furanyl)fluorenyl | | |
| | bis(pyrrolyl)fluorenyl | | |
| | bis(phospholyl)fluorenyl | | |
| | bis(methylthienyl)fluorenyl | | |
| | bis(methylfuranyl)fluorenyl | | |
| | bis(methylpyrrolyl)fluorenyl | | |
| | bis(methylphospholyl)fluorenyl | | |
| | bis(dimethylthienyl)fluorenyl | | |
| | bis(dimethylfuranyl)fluorenyl | | |
| | bis(dimethylpyrrolyl)fluorenyl | | |
| | bis(dimethylphospholyl)fluorenyl | | |
| | azacyclopentadienyl | | |
| | phosphacyclopentadienyl | | |
| | stibacyclopentadienyl | | |
| | arsacyclopentadienyl | | |
| | boracyclopentadienyl | | |
| | methylazacyclopentadienyl | | |
| | methylphosphacyclopentadienyl | | |
| | methylstibacyclopentadienyl | | |
| | methylarsacyclopentadienyl | | |
| | methylboracyclopentadienyl | | |
| | 1,2-diazacyclopentadienyl | | |
| | 1,2-diphosphacyclopentadienyl | | |
| | 1,2-distibacyclopentadienyl | | |
| | 1,2-diarsacyclopentadienyl | | |
| | 1,2-diboracyclopentadienyl | | |
| | 1,2-azaphosphacyclopentadienyl | | |
| | 1,2-azastibacyclopentadienyl | | |
| | 1,2-azarsacyclopentadienyl | | |
| | 1,2-azaboracyclopentadienyl | | |
| | 1,2-arsaphosphacyclopentadienyl | | |
| | 1,2-arsastibacyclopentadienyl | | |
| | 1,2-arsaboracyclopentadienyl | | |
| | 1,2-boraphosphacyclopentadienyl | | |
| | 1,2-borastibacyclopentadienyl | | |
| | 1,2-phosphastibacyclopentadienyl | | |
| | 1,3-diazacyclopentadienyl | | |
| | 1,3-diphosphacyclopentadienyl | | |
| | 1,3-distibacyclopentadienyl | | |
| | 1,3-diarsacyclopentadienyl | | |
| | 1,3-diboracyclopentadienyl | | |
| | 1,3-azaphosphacyclopentadienyl | | |
| | 1,3-azastibacyclopentadienyl | | |
| | 1,3-azarsacyclopentadienyl | | |
| | 1,3-azaboracyclopentadienyl | | |
| | 1,3-arsaphosphacyclopentadienyl | | |
| | 1,3-arsastibacyclopentadienyl | | |
| | 1,3-arsaboracyclopentadienyl | | |
| | 1,3-boraphosphacyclopentadienyl | | |
| | 1,3-borastibacyclopentadienyl | | |
| | 1,3-phosphastibacyclopentadienyl | | |
| | pentadienyl | | |
| | methylpentadienyl | | |
| | dimethylpentadienyl | | |
| | trimethylpentadienyl | | |

TABLE 1-continued

| Y | A | $R^1, R^2, R^3, R^4, R^5, R^6, R^7,$<br>$R^8, R^9, R^{10}, R^{11},$ or $R^{12}$ | X |
|---|---|---|---|
| | tetramethylpentadienyl<br>pentamethylpentadienyl<br>hexamethylpentadienyl<br>allyl<br>methylallyl<br>dimethylallyl<br>trimethylallyl<br>tetramethylallyl<br>boratabenzene<br>methylboratabenzene<br>phenylboratabenzene<br>N,N-dimethylaminoboratabenzene<br>N,N-diethylaminoboratabenzene<br>N,N-dipropylaminoboratabenzene | | |

In a preferred embodiment of formula 2, A is the same as the indenyl ligand bonded to M.

Particularly preferred embodiments of formula 2 include compounds where:
1) each $R^1, R^2, R^3, R^4, R^5$, and $R^6$ is, independently, selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably each $R^1, R^2, R^3, R^4, R^5$, and $R^6$ is, independently, selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl; and/or
2) Y is selected from the group of diradicals consisting of PR, RP—PR, RN—PR; and/or
3) each R is, independently, selected from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably methyl, ethyl, n-propyl, iso-propyl, n-butyl, s-butyl, i-butyl, t-butyl, n-hexyl, cyclohexyl, phenyl, tolyl, mesityl, and naphthyl; and/or
4) X is, independently, selected from the group consisting of chloride, bromide, fluoride, iodide, hydride, and C1 to C30 hydrocarbyls, preferably methyl, ethyl, propyl, butyl, pentyl, hexyl, phenyl, benzyl, and all isomers thereof, or two X together are selected from C4–C10 dienes, preferably butadiene, methylbutadiene, pentadiene, methylpentadiene, dimethylpentadiene, hexadiene, methylhexadiene, dimethylhexadiene, or from C1–C10 alkylidenes, preferably methylidene, ethylidene, propylidene, or from C3–C10 alkyldiyls, preferably propandiyl, butandiyl, pentandiyl, and hexandiyl; and/or
5) M is Ti, Zr, or Hf; and/or
6) A is selected from the group consisting of substituted or unsubstituted indenyl, substituted or unsubstituted fluorenyl and substituted or unsubstituted cyclopentadienyl, more preferably, indenyl, methylindenyl, dimethylindenyl, methylphenylindenyl, methyltolylindenyl, methyl (dipropylphenyl)indenyl, methyl(dimethylphenyl)indenyl methylnaphthylindenyl, tetrahydroindenyl, fluorenyl, octahydrofluorenyl, dibutylfluorenyl, cyclopentadienyl, methylcyclopentadienyl, ethylcyclopentadienyl, propylcyclopentadienyl, butylcyclopentadienyl, methylpropylcyclopentadienyl, methylbutylcyclopentadienyl, dimethylcyclopentadienyl, trimethylcyclopentadienyl, and tetramethylcyclopentadienyl.

Particularly preferred embodiments of formulae 3 include compounds where:
1) each $R^1, R^2, R^3, R^4, R^5, R^6, R^7, R^8, R^9, R^{10}, R^{11}$, and $R^{12}$ is, independently, selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably each $R^1, R^2, R^3, R^4, R^5, R^6, R^7, R^8, R^9, R^{10}, R^{11}$, and $R^{12}$ is independently, selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl; and/or
2) Y is selected from the group of diradicals consisting of PR, RP—PR, RN—PR; and/or
3) each R is, independently, selected from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably methyl, ethyl, n-propyl, iso-propyl, n-butyl, s-butyl, i-butyl, t-butyl, n-hexyl, cyclohexyl, phenyl, tolyl, mesityl, and naphthyl; and/or
4) X is, independently, selected from the group consisting of chloride, bromide, fluoride, iodide, hydride, and C1 to C30 hydrocarbyls, preferably methyl, ethyl, propyl, butyl, pentyl, hexyl, phenyl, benzyl, and all isomers thereof, or two X together are selected from C4–C 10 dienes, preferably butadiene, methylbutadiene, pentadiene, methylpentadiene, dimethylpentadiene, hexadiene, methylhexadiene, dimethylhexadiene, or from C1–C10 alkylidenes, preferably methylidene, ethylidene, propylidene, or from C3–C10 alkyldiyls, preferably propandiyl, butandiyl, pentandiyl, and hexandiyl, and/or
5) M is Ti, Zr, or Hf.

A set of exemplary catalyst precursors is set out below. These are by way of example only and are not intended to list every catalyst precursor that is within the scope of the invention. Particularly preferred transition metal compounds include:
2,2'-phenylphosphindiyl-bis(indenyl)zirconium dichloride,
2,2'-methylphosphindiyl-bis(indenyl)zirconium dichloride,
2,2'-ethylphosphindiyl-bis(indenyl)zirconium dichloride,
2,2'-propylphosphindiyl-bis(indenyl)zirconium dichloride,
2,2'-butylphosphindiyl-bis(indenyl)zirconium dichloride, 2,2'-(1,2-dimethyldiphosphandiyl)-bis(indenyl)zirconium dichloride,
2,1'-phenylphosphindiyl(indenyl)(cyclopentadienyl)zirconium dichloride,
2,1'-methylphosphindiyl(indenyl)(cyclopentadienyl)zirconium dichloride,
2,1'-ethylphosphindiyl(indenyl)(cyclopentadienyl)zirconium dichloride,
2,1'-propylphosphindiyl(indenyl)(cyclopentadienyl)zirconium dichloride,
2,1'-butylphosphindiyl(indenyl)(cyclopentadienyl)zirconium dichloride,
2,1'-1,2-dimethyldiphosphandiyl)(indenyl)(cyclopentadienyl)zirconium dichloride,
2,2'-phenylphosphindiyl(indenyl)(tetrahydroindenyl)zirconium dichloride,
2,2'-methylphosphindiyl(indenyl)(tetrahydroindenyl)zirconium dichloride,
2,2'-ethylphosphindiyl(indenyl)(tetrahydroindenyl)zirconium dichloride,
2,2'-propylphosphindiyl(indenyl)(tetrahydroindenyl)zirconium dichloride,
2,2'-butylphosphindiyl(indenyl)(tetrahydroindenyl)zirconium dichloride,
2,2'-(1,2-dimethyldiphosphandiyl)(indenyl)(tetrahydroindenyl)zirconium dichloride,
2,2'-phenylphosphindiyl-bis(4-phenylindenyl)zirconium dichloride,
2,2'-methylphosphindiyl-bis(4-phenylindenyl)zirconium dichloride,
2,2'-ethylphosphindiyl-bis(4-phenylindenyl)zirconium dichloride,
2,2'-propylphosphindiyl-bis(4-phenylindenyl)zirconium dichloride,
2,2'-butylphosphindiyl-bis(4-phenylindenyl)zirconium dichloride,
2,2'-(1,2-dimethyldiphosphandiyl)-bis(4-phenylindenyl)zirconium dichloride,
2,2'-phenylphosphindiyl-bis(4,7-dimethylindenyl)zirconium dichloride,
2,2'-methylphosphindiyl-bis(4,7-dimethylindenyl)zirconium dichloride,
2,2'-ethylphosphindiyl-bis(4,7-dimethylindenyl)zirconium dichloride,
2,2'-propylphosphindiyl-bis(4,7-dimethylindenyl)zirconium dichloride,
2,2'-butylphosphindiyl-bis(4,7-dimethylindenyl)zirconium dichloride,
2,2'-(1,2-dimethyldiphosphandiyl)-bis(4,7-dimethylindenyl)zirconium dichloride,
2,1'-phenylphosphindiyl(indenyl)(3-methylcyclopentadienyl)zirconium dichloride,
2,1'-methylphosphindiyl(indenyl)(3-methylcyclopentadienyl)zirconium dichloride,
2,1'-ethylphosphindiyl(indenyl)(3-methylcyclopentadienyl)zirconium dichloride,
2,1'-propylphosphindiyl(indenyl)(3-methylcyclopentadienyl)zirconium dichloride,
2,1'-butylphosphindiyl(indenyl)(3-methylcyclopentadienyl)zirconium dichloride,
2,1'-(1,2-dimethyldiphosphandiyl)(indenyl)(3-methylcyclopentadienyl)zirconium dichloride,
2,1'-phenylphosphindiyl(indenyl)(2,4-dimethylcyclopentadienyl)zirconium dichloride,
2,1'-methylphosphindiyl(indenyl)(2,4-dimethylcyclopentadienyl)zirconium dichloride,
2,1'-ethylphosphindiyl(indenyl)(2,4-dimethylcyclopentadienyl)zirconium dichloride,
2,1'-propylphosphindiyl(indenyl)(2,4-dimethylcyclopentadienyl)zirconium dichloride,
2,1'-butylphosphindiyl(indenyl)(2,4-dimethylcyclopentadienyl)zirconium dichloride,
2,1'-(1,2-dimethyldiphosphandiyl)(indenyl)(2,4-dimethylcyclopentadienyl)zirconium dichloride,
2,1'-phenylphosphindiyl(indenyl)(2-methyl-4-butylcyclopentadienyl)zirconium dichloride,
2,1'-methylphosphindiyl(indenyl)(2-methyl-4-butylcyclopentadienyl)zirconium dichloride,
2,1'-ethylphosphindiyl(indenyl)(2-methyl-4-butylcyclopentadienyl)zirconium dichloride,
2,1'-propylphosphindiyl(indenyl)(2-methyl-4-butylcyclopentadienyl)zirconium dichloride,
2,1'-butylphosphindiyl(indenyl)(2-methyl-4-butylcyclopentadienyl)zirconium dichloride,
2,1'-(1,2-dimethyldiphosphandiyl)(indenyl)(2-methyl-4-butylcyclopentadienyl)zirconium dichloride,
2,9'-phenylphosphindiyl(indenyl)(fluorenyl)zirconium dichloride,
2,9'-methylphosphindiyl(indenyl)(fluorenyl)zirconium dichloride,
2,9'-ethylphosphindiyl(indenyl)(fluorenyl)zirconium dichloride,
2,9'-propylphosphindiyl(indenyl)(fluorenyl)zirconium dichloride,
2,9'-butylphosphindiyl(indenyl)(fluorenyl)zirconium dichloride,
2,9'-(1,2-dimethyldiphosphandiyl)(indenyl)(fluorenyl)zirconium dichloride,
2,2'-phenylphosphindiyl-bis(indenyl)zirconium dimethyl,
2,2'-methylphosphindiyl-bis(indenyl)zirconium dimethyl,
2,2'-ethylphosphindiyl-bis(indenyl)zirconium dimethyl,
2,2'-propylphosphindiyl-bis(indenyl)zirconium dimethyl,
2,2'-butylphosphindiyl-bis(indenyl)zirconium dimethyl,
2,2'-(1,2-dimethyldiphosphandiyl)-bis(indenyl)zirconium dimethyl,
2,1'-phenylphosphindiyl(indenyl)(cyclopentadienyl)zirconium dimethyl,
2,1'-methylphosphindiyl(indenyl)(cyclopentadienyl)zirconium dimethyl,
2,1'-ethylphosphindiyl(indenyl)(cyclopentadienyl)zirconium dimethyl,
2,1'-propylphosphindiyl(indenyl)(cyclopentadienyl)zirconium dimethyl,
2,1'-butylphosphindiyl(indenyl)(cyclopentadienyl)zirconium dimethyl,
2,1'-1,2-dimethyldiphosphandiyl)(indenyl)(cyclopentadienyl)zirconium dimethyl,
2,2'-phenylphosphindiyl(indenyl)(tetrahydroindenyl)zirconium dimethyl,
2,2'-methylphosphindiyl(indenyl)(tetrahydroindenyl)zirconium dimethyl,
2,2'-ethylphosphindiyl(indenyl)(tetrahydroindenyl)zirconium dimethyl,
2,2'-propylphosphindiyl(indenyl)(tetrahydroindenyl)zirconium dimethyl,
2,2'-butylphosphindiyl(indenyl)(tetrahydroindenyl)zirconium dimethyl,
2,2'-(1,2-dimethyldiphosphandiyl)(indenyl)(tetrahydroindenyl)zirconium dimethyl,
2,2'-phenylphosphindiyl-bis(4-phenylindenyl)zirconium dimethyl,
2,2'-methylphosphindiyl-bis(4-phenylindenyl)zirconium dimethyl, 2,2'-ethylphosphindiyl-bis(4-phenylindenyl)zirconium dimethyl,
2,2'-propylphosphindiyl-bis(4-phenylindenyl)zirconium dimethyl,
2,2'-butylphosphindiyl-bis(4-phenylindenyl)zirconium dimethyl,
2,2'-(1,2-dimethyldiphosphandiyl)-bis(4-phenylindenyl)zirconium dimethyl,
2,2'-phenylphosphindiyl-bis(4,7-dimethylindenyl)zirconium dimethyl,
2,2'-methylphosphindiyl-bis(4,7-dimethylindenyl)zirconium dimethyl,
2,2'-ethylphosphindiyl-bis(4,7-dimethylindenyl)zirconium dimethyl,
2,2'-propylphosphindiyl-bis(4,7-dimethylindenyl)zirconium dimethyl,
2,2'-butylphosphindiyl-bis(4,7-dimethylindenyl)zirconium dimethyl,
2,2'-(1,2-dimethyldiphosphandiyl)-bis(4,7-dimethylindenyl)zirconium dimethyl,
2,1'-phenylphosphindiyl(indenyl)(3-methylcyclopentadienyl)zirconium dimethyl,
2,1'-methylphosphindiyl(indenyl)(3-methylcyclopentadienyl)zirconium dimethyl,
2,1'-ethylphosphindiyl(indenyl)(3-methylcyclopentadienyl)zirconium dimethyl,
2,1'-propylphosphindiyl(indenyl)(3-methylcyclopentadienyl)zirconium dimethyl,
2,1'-butylphosphindiyl(indenyl)(3-methylcyclopentadienyl)zirconium dimethyl,
2,1'-(1,2-dimethyldiphosphandiyl)(indenyl)(3-methylcyclopentadienyl)zirconium dimethyl,
2,1'-phenylphosphindiyl(indenyl)(2,4-dimethylcyclopentadienyl)zirconium dimethyl,
2,1'-methylphosphindiyl(indenyl)(2,4-dimethylcyclopentadienyl)zirconium dimethyl,
2,1'-ethylphosphindiyl(indenyl)(2,4-dimethylcyclopentadienyl)zirconium dimethyl,
2,1'-propylphosphindiyl(indenyl)(2,4-dimethylcyclopentadienyl)zirconium dimethyl,
2,1'-butylphosphindiyl(indenyl)(2,4-dimethylcyclopentadienyl)zirconium dimethyl,
2,1'-(1,2-dimethyldiphosphandiyl)(indenyl)(2,4-dimethylcyclopentadienyl)zirconium dimethyl,
2,1'-phenylphosphindiyl(indenyl)(2-methyl-4-butylcyclopentadienyl)zirconium dimethyl,
2,1'-methylphosphindiyl(indenyl)(2-methyl-4-butylcyclopentadienyl)zirconium dimethyl,
2,1'-ethylphosphindiyl(indenyl)(2-methyl-4-butylcyclopentadienyl)zirconium dimethyl,
2,1'-propylphosphindiyl(indenyl)(2-methyl-4-butylcyclopentadienyl)zirconium dimethyl,
2,1'-butylphosphindiyl(indenyl)(2-methyl-4-butylcyclopentadienyl)zirconium dimethyl,
2,1'-(1,2-dimethyldiphosphandiyl)(indenyl)(2-methyl-4-butylcyclopentadienyl)zirconium dimethyl,
2,9'-phenylphosphindiyl(indenyl)(fluorenyl)zirconium dimethyl,
2,9'-methylphosphindiyl(indenyl)(fluorenyl)zirconium dimethyl,
2,9'-ethylphosphindiyl(indenyl)(fluorenyl)zirconium dimethyl,
2,9'-propylphosphindiyl(indenyl)(fluorenyl)zirconium dimethyl,
2,9'-butylphosphindiyl(indenyl)(fluorenyl)zirconium dimethyl,
2,9'-(1,2-dimethyldiphosphandiyl)(indenyl)(fluorenyl)zirconium dimethyl,
2,2'-phenylphosphindiyl-bis(indenyl)zirconium dibenzyl,
2,2'-methylphosphindiyl-bis(indenyl)zirconium dibenzyl,
2,2'-ethylphosphindiyl-bis(indenyl)zirconium dibenzyl,
2,2'-propylphosphindiyl-bis(indenyl)zirconium dibenzyl,
2,2'-butylphosphindiyl-bis(indenyl)zirconium dibenzyl,
2,2'-(1,2-dimethyldiphosphandiyl)-bis(indenyl)zirconium dibenzyl,
2,1'-phenylphosphindiyl(indenyl)(cyclopentadienyl)zirconium dibenzyl,
2,1'-methylphosphindiyl(indenyl)(cyclopentadienyl)zirconium dibenzyl,
2,1'-ethylphosphindiyl(indenyl)(cyclopentadienyl)zirconium dibenzyl,
2,1'-propylphosphindiyl(indenyl)(cyclopentadienyl)zirconium dibenzyl,
2,1'-butylphosphindiyl(indenyl)(cyclopentadienyl)zirconium dibenzyl,
2,1'-1,2-dimethyldiphosphandiyl)(indenyl)(cyclopentadienyl)zirconium dibenzyl,
2,2'-phenylphosphindiyl(indenyl)(tetrahydroindenyl)zirconium dibenzyl,
2,2'-methylphosphindiyl(indenyl)(tetrahydroindenyl)zirconium dibenzyl,
2,2'-ethylphosphindiyl(indenyl)(tetrahydroindenyl)zirconium dibenzyl,
2,2'-propylphosphindiyl(indenyl)(tetrahydroindenyl)zirconium dibenzyl,
2,2'-butylphosphindiyl(indenyl)(tetrahydroindenyl)zirconium dibenzyl,
2,2'-(1,2-dimethyldiphosphandiyl)(indenyl)(tetrahydroindenyl)zirconium dibenzyl,
2,2'-phenylphosphindiyl-bis(4-phenylindenyl)zirconium dibenzyl,
2,2'-methylphosphindiyl-bis(4-phenylindenyl)zirconium dibenzyl,
2,2'-ethylphosphindiyl-bis(4-phenylindenyl)zirconium dibenzyl,
2,2'-propylphosphindiyl-bis(4-phenylindenyl)zirconium dibenzyl,
2,2'-butylphosphindiyl-bis(4-phenylindenyl)zirconium dibenzyl,
2,2'-(1,2-dimethyldiphosphandiyl)-bis(4-phenylindenyl)zirconium dibenzyl,
2,2'-phenylphosphindiyl-bis(4,7-dimethylindenyl)zirconium dibenzyl,
2,2'-methylphosphindiyl-bis(4,7-dimethylindenyl)zirconium dibenzyl,
2,2'-ethylphosphindiyl-bis(4,7-dimethylindenyl)zirconium dibenzyl,
2,2'-propylphosphindiyl-bis(4,7-dimethylindenyl)zirconium dibenzyl,
2,2'-butylphosphindiyl-bis(4,7-dimethylindenyl)zirconium dibenzyl,
2,2'-(1,2-dimethyldiphosphandiyl)-bis(4,7-dimethylindenyl)zirconium dibenzyl,
2,1'-phenylphosphindiyl(indenyl)(3-methylcyclopentadienyl)zirconium dibenzyl,
2,1'-methylphosphindiyl(indenyl)(3-methylcyclopentadienyl)zirconium dibenzyl,
2,1'-ethylphosphindiyl(indenyl)(3-methylcyclopentadienyl)zirconium dibenzyl,
2,1'-propylphosphindiyl(indenyl)(3-methylcyclopentadienyl)zirconium dibenzyl,
2,1'-butylphosphindiyl(indenyl)(3-methylcyclopentadienyl)zirconium dibenzyl, 2,1'-(1,2-dimethyldiphosphandiyl)(indenyl)(3-methylcyclopentadienyl)zirconium dibenzyl,
2,1'-phenylphosphindiyl(indenyl)(2,4-dimethylcyclopentadienyl)zirconium dibenzyl,
2,1'-methylphosphindiyl(indenyl)(2,4-dimethylcyclopentadienyl)zirconium dibenzyl,
2,1'-ethylphosphindiyl(indenyl)(2,4-dimethylcyclopentadienyl)zirconium dibenzyl,
2,1'-propylphosphindiyl(indenyl)(2,4-dimethylcyclopentadienyl)zirconium dibenzyl,
2,1'-butylphosphindiyl(indenyl)(2,4-dimethylcyclopentadienyl)zirconium dibenzyl,
2,1'-(1,2-dimethyldiphosphandiyl)(indenyl)(2,4-dimethylcyclopentadienyl)zirconium dibenzyl,
2,1'-phenylphosphindiyl(indenyl)(2-methyl-4-butylcyclopentadienyl)zirconium dibenzyl,
2,1'-methylphosphindiyl(indenyl)(2-methyl-4-butylcyclopentadienyl)zirconium dibenzyl,
2,1'-ethylphosphindiyl(indenyl)(2-methyl-4-butylcyclopentadienyl)zirconium dibenzyl,
2,1'-propylphosphindiyl(indenyl)(2-methyl-4-butylcyclopentadienyl)zirconium dibenzyl,
2,1'-butylphosphindiyl(indenyl)(2-methyl-4-butylcyclopentadienyl)zirconium dibenzyl,
2,1'-(1,2-dimethyldiphosphandiyl)(indenyl)(2-methyl-4-butylcyclopentadienyl)zirconium dibenzyl,
2,9'-phenylphosphindiyl(indenyl)(fluorenyl)zirconium dibenzyl,
2,9'-methylphosphindiyl(indenyl)(fluorenyl)zirconium dibenzyl,
2,9'-ethylphosphindiyl(indenyl)(fluorenyl)zirconium dibenzyl,
2,9'-propylphosphindiyl(indenyl)(fluorenyl)zirconium dibenzyl,
2,9'-butylphosphindiyl(indenyl)(fluorenyl)zirconium dibenzyl,
2,9'-(1,2-dimethyldiphosphandiyl)(indenyl)(fluorenyl)zirconium dibenzyl,
2,2'-phenylphosphindiyl-bis(indenyl)zirconium difluoride,
2,2'-methylphosphindiyl-bis(indenyl)zirconium difluoride,
2,2'-ethylphosphindiyl-bis(indenyl)zirconium difluoride,
2,2'-propylphosphindiyl-bis(indenyl)zirconium difluoride,
2,2'-butylphosphindiyl-bis(indenyl)zirconium difluoride,
2,2'-(1,2-dimethyldiphosphandiyl)-bis(indenyl)zirconium difluoride,
2,1'-phenylphosphindiyl(indenyl)(cyclopentadienyl)zirconium difluoride,
2,1'-methylphosphindiyl(indenyl)(cyclopentadienyl)zirconium difluoride,
2,1'-ethylphosphindiyl(indenyl)(cyclopentadienyl)zirconium difluoride,
2,1'-propylphosphindiyl(indenyl)(cyclopentadienyl)zirconium difluoride,
2,1'-butylphosphindiyl(indenyl)(cyclopentadienyl)zirconium difluoride,
2,1'-1,2-dimethyldiphosphandiyl)(indenyl)(cyclopentadienyl)zirconium difluoride,
2,2'-phenylphosphindiyl(indenyl)(tetrahydroindenyl)zirconium difluoride,
2,2'-methylphosphindiyl(indenyl)(tetrahydroindenyl)zirconium difluoride,
2,2'-ethylphosphindiyl(indenyl)(tetrahydroindenyl)zirconium difluoride,
2,2'-propylphosphindiyl(indenyl)(tetrahydroindenyl)zirconium difluoride,
2,2'-butylphosphindiyl(indenyl)(tetrahydroindenyl)zirconium difluoride,
2,2'-(1,2-dimethyldiphosphandiyl)(indenyl)(tetrahydroindenyl)zirconium difluoride,
2,2'-phenylphosphindiyl-bis(4-phenylindenyl)zirconium difluoride,
2,2'-methylphosphindiyl-bis(4-phenylindenyl)zirconium difluoride,
2,2'-ethylphosphindiyl-bis(4-phenylindenyl)zirconium difluoride,
2,2'-propylphosphindiyl-bis(4-phenylindenyl)zirconium difluoride,
2,2'-butylphosphindiyl-bis(4-phenylindenyl)zirconium difluoride,
2,2'-(1,2-dimethyldiphosphandiyl)-bis(4-phenylindenyl)zirconium difluoride,
2,2'-phenylphosphindiyl-bis(4,7-dimethylindenyl)zirconium difluoride,
2,2'-methylphosphindiyl-bis(4,7-dimethylindenyl)zirconium difluoride,
2,2'-ethylphosphindiyl-bis(4,7-dimethylindenyl)zirconium difluoride,
2,2'-propylphosphindiyl-bis(4,7-dimethylindenyl)zirconium difluoride,
2,2'-butylphosphindiyl-bis(4,7-dimethylindenyl)zirconium difluoride,
2,2'-(1,2-dimethyldiphosphandiyl)-bis(4,7-dimethylindenyl)zirconium difluoride,
2,1'-phenylphosphindiyl(indenyl)(3-methylcyclopentadienyl)zirconium difluoride,
2,1'-methylphosphindiyl(indenyl)(3-methylcyclopentadienyl)zirconium difluoride,
2,1'-ethylphosphindiyl(indenyl)(3-methylcyclopentadienyl)zirconium difluoride,
2,1'-propylphosphindiyl(indenyl)(3-methylcyclopentadienyl)zirconium difluoride,
2,1'-butylphosphindiyl(indenyl)(3-methylcyclopentadienyl)zirconium difluoride,
2,1'-(1,2-dimethyldiphosphandiyl)(indenyl)(3-methylcyclopentadienyl)zirconium difluoride,
2,1'-phenylphosphindiyl(indenyl)(2,4-dimethylcyclopentadienyl)zirconium difluoride,
2,1'-methylphosphindiyl(indenyl)(2,4-dimethylcyclopentadienyl)zirconium difluoride,
2,1'-ethylphosphindiyl(indenyl)(2,4-dimethylcyclopentadienyl)zirconium difluoride,
2,1'-propylphosphindiyl(indenyl)(2,4-dimethylcyclopentadienyl)zirconium difluoride,
2,1'-butylphosphindiyl(indenyl)(2,4-dimethylcyclopentadienyl)zirconium difluoride,
2,1'-(1,2-dimethyldiphosphandiyl)(indenyl)(2,4-dimethylcyclopentadienyl)zirconium difluoride,
2,1'-phenylphosphindiyl(indenyl)(2-methyl-4-butylcyclopentadienyl)zirconium difluoride,
2,1'-methylphosphindiyl(indenyl)(2-methyl-4-butylcyclopentadienyl)zirconium difluoride,
2,1'-ethylphosphindiyl(indenyl)(2-methyl-4-butylcyclopentadienyl)zirconium difluoride,
2,1'-propylphosphindiyl(indenyl)(2-methyl-4-butylcyclopentadienyl)zirconium difluoride,
2,1'-butylphosphindiyl(indenyl)(2-methyl-4-butylcyclopentadienyl)zirconium difluoride,
2,1'-(1,2-dimethyldiphosphandiyl)(indenyl)(2-methyl-4-butylcyclopentadienyl)zirconium difluoride,
2,9'-phenylphosphindiyl(indenyl)(fluorenyl)zirconium difluoride,
2,9'-methylphosphindiyl(indenyl)(fluorenyl)zirconium difluoride, 2,9'-ethylphosphindiyl(indenyl)(fluorenyl)zirconium difluoride,
2,9'-propylphosphindiyl(indenyl)(fluorenyl)zirconium difluoride,
2,9'-butylphosphindiyl(indenyl)(fluorenyl)zirconium difluoride,
2,9'-(1,2-dimethyldiphosphandiyl)(indenyl)(fluorenyl)zirconium difluoride,
2,1'-phenylphosphindiyl-bis(indenyl)zirconium dichloride,
2,1'-methylphosphindiyl-bis(indenyl)zirconium dichloride,
2,1'-ethylphosphindiyl-bis(indenyl)zirconium dichloride,
2,1'-propylphosphindiyl-bis(indenyl)zirconium dichloride,
2,1'-butylphosphindiyl-bis(indenyl)zirconium dichloride,
2,1'-(1,2-dimethyldiphosphandiyl)-bis(indenyl)zirconium dichloride,
2,2'-phenylphosphindiyl-bis(indenyl)hafnium dichloride,
2,2'-methylphosphindiyl-bis(indenyl)hafnium dichloride,
2,2'-ethylphosphindiyl-bis(indenyl)hafnium dichloride,
2,2'-propylphosphindiyl-bis(indenyl)hafnium dichloride,
2,2'-butylphosphindiyl-bis(indenyl)hafnium dichloride,
2,2'-(1,2-dimethyldiphosphandiyl)-bis(indenyl)hafnium dichloride,
2,1'-phenylphosphindiyl(indenyl)(cyclopentadienyl)hafnium dichloride,
2,1'-methylphosphindiyl(indenyl)(cyclopentadienyl)hafnium dichloride,
2,1'-ethylphosphindiyl(indenyl)(cyclopentadienyl)hafnium dichloride,
2,1'-propylphosphindiyl(indenyl)(cyclopentadienyl)hafnium dichloride,
2,1'-butylphosphindiyl(indenyl)(cyclopentadienyl)hafnium dichloride,
2,1'-1,2-dimethyldiphosphandiyl)(indenyl)(cyclopentadienyl)hafnium dichloride,
2,2'-phenylphosphindiyl(indenyl)(tetrahydroindenyl)hafnium dichloride,
2,2'-methylphosphindiyl(indenyl)(tetrahydroindenyl)hafnium dichloride,
2,2'-ethylphosphindiyl(indenyl)(tetrahydroindenyl)hafnium dichloride,
2,2'-propylphosphindiyl(indenyl)(tetrahydroindenyl)hafnium dichloride,
2,2'-butylphosphindiyl(indenyl)(tetrahydroindenyl)hafnium dichloride,
2,2'-(1,2-dimethyldiphosphandiyl)(indenyl)(tetrahydroindenyl)hafnium dichloride,
2,2'-phenylphosphindiyl-bis(4-phenylindenyl)hafnium dichloride,
2,2'-methylphosphindiyl-bis(4-phenylindenyl)hafnium dichloride,
2,2'-ethylphosphindiyl-bis(4-phenylindenyl)hafnium dichloride,
2,2'-propylphosphindiyl-bis(4-phenylindenyl)hafnium dichloride,
2,2'-butylphosphindiyl-bis(4-phenylindenyl)hafnium dichloride,
2,2'-(1,2-dimethyldiphosphandiyl)-bis(4-phenylindenyl)hafnium dichloride,
2,2'-phenylphosphindiyl-bis(4,7-dimethylindenyl)hafnium dichloride,
2,2'-methylphosphindiyl-bis(4,7-dimethylindenyl)hafnium dichloride,
2,2'-ethylphosphindiyl-bis(4,7-dimethylindenyl)hafnium dichloride,
2,2'-propylphosphindiyl-bis(4,7-dimethylindenyl)hafnium dichloride,
2,2'-butylphosphindiyl-bis(4,7-dimethylindenyl)hafnium dichloride,
2,2'-(1,2-dimethyldiphosphandiyl)-bis(4,7-dimethylindenyl)hafnium dichloride,
2,1'-phenylphosphindiyl(indenyl)(3-methylcyclopentadienyl)hafnium dichloride,
2,1'-methylphosphindiyl(indenyl)(3-methylcyclopentadienyl)hafnium dichloride,
2,1'-ethylphosphindiyl(indenyl)(3-methylcyclopentadienyl)hafnium dichloride,
2,1'-propylphosphindiyl(indenyl)(3-methylcyclopentadienyl)hafnium dichloride,
2,1'-butylphosphindiyl(indenyl)(3-methylcyclopentadienyl)hafnium dichloride,
2,1'-(1,2-dimethyldiphosphandiyl)(indenyl)(3-methylcyclopentadienyl)hafnium dichloride,
2,1'-phenylphosphindiyl(indenyl)(2,4-dimethylcyclopentadienyl)hafnium dichloride,
2,1'-methylphosphindiyl(indenyl)(2,4-dimethylcyclopentadienyl)hafnium dichloride,
2,1'-ethylphosphindiyl(indenyl)(2,4-dimethylcyclopentadienyl)hafnium dichloride,
2,1'-propylphosphindiyl(indenyl)(2,4-dimethylcyclopentadienyl)hafnium dichloride,
2,1'-butylphosphindiyl(indenyl)(2,4-dimethylcyclopentadienyl)hafnium dichloride,
2,1'-(1,2-dimethyldiphosphandiyl)(indenyl)(2,4-dimethylcyclopentadienyl)hafnium dichloride,
2,1'-phenylphosphindiyl(indenyl)(2-methyl-4-butylcyclopentadienyl)hafnium dichloride,
2,1'-methylphosphindiyl(indenyl)(2-methyl-4-butylcyclopentadienyl)hafnium dichloride,
2,1'-ethylphosphindiyl(indenyl)(2-methyl-4-butylcyclopentadienyl)hafnium dichloride,
2,1'-propylphosphindiyl(indenyl)(2-methyl-4-butylcyclopentadienyl)hafnium dichloride,
2,1'-butylphosphindiyl(indenyl)(2-methyl-4-butylcyclopentadienyl)hafnium dichloride,
2,1'-(1,2-dimethyldiphosphandiyl)(indenyl)(2-methyl-4-butylcyclopentadienyl)hafnium dichloride,
2,9'-phenylphosphindiyl(indenyl)(fluorenyl)hafnium dichloride,
2,9'-methylphosphindiyl(indenyl)(fluorenyl)hafnium dichloride,
2,9'-ethylphosphindiyl(indenyl)(fluorenyl)hafnium dichloride,
2,9'-propylphosphindiyl(indenyl)(fluorenyl)hafnium dichloride,
2,9'-butylphosphindiyl(indenyl)(fluorenyl)hafnium dichloride,
2,9'-(1,2-dimethyldiphosphandiyl)(indenyl)(fluorenyl)hafnium dichloride,
2,2'-phenylphosphindiyl-bis(indenyl)hafnium dimethyl,
2,2'-methylphosphindiyl-bis(indenyl)hafnium dimethyl,
2,2'-ethylphosphindiyl-bis(indenyl)hafnium dimethyl,
2,2'-propylphosphindiyl-bis(indenyl)hafnium dimethyl,
2,2'-butylphosphindiyl-bis(indenyl)hafnium dimethyl,
2,2'-(1,2-dimethyldiphosphandiyl)-bis(indenyl)hafnium dimethyl,
2,1'-phenylphosphindiyl(indenyl)(cyclopentadienyl)hafnium dimethyl,
2,1'-methylphosphindiyl(indenyl)(cyclopentadienyl)hafnium dimethyl,
2,1'-ethylphosphindiyl(indenyl)(cyclopentadienyl)hafnium dimethyl,
2,1'-propylphosphindiyl(indenyl)(cyclopentadienyl)hafnium dimethyl, 2,1'-butylphosphindiyl(indenyl)(cyclopentadienyl)hafnium dimethyl,
2,1'-1,2-dimethyldiphosphandiyl)(indenyl)(cyclopentadienyl)hafnium dimethyl,
2,2'-phenylphosphindiyl(indenyl)(tetrahydroindenyl) hafnium dimethyl,
2,2'-methylphosphindiyl(indenyl)(tetrahydroindenyl) hafnium dimethyl,
2,2'-ethylphosphindiyl(indenyl)(tetrahydroindenyl)hafnium dimethyl,
2,2'-propylphosphindiyl(indenyl)(tetrahydroindenyl) hafnium dimethyl,
2,2'-butylphosphindiyl(indenyl)(tetrahydroindenyl)hafnium dimethyl,
2,2'-(1,2-dimethyldiphosphandiyl)(indenyl)(tetrahydroindenyl)hafnium dimethyl,
2,2'-phenylphosphindiyl-bis(4-phenylindenyl)hafnium dimethyl,
2,2'-methylphosphindiyl-bis(4-phenylindenyl)hafnium dimethyl,
2,2'-ethylphosphindiyl-bis(4-phenylindenyl)hafnium dimethyl,
2,2'-propylphosphindiyl-bis(4-phenylindenyl)hafnium dimethyl,
2,2'-butylphosphindiyl-bis(4-phenylindenyl)hafnium dimethyl,
2,2'-(1,2-dimethyldiphosphandiyl)-bis(4-phenylindenyl) hafnium dimethyl,
2,2'-phenylphosphindiyl-bis(4,7-dimethylindenyl)hafnium dimethyl,
2,2'-methylphosphindiyl-bis(4,7-dimethylindenyl)hafnium dimethyl,
2,2'-ethylphosphindiyl-bis(4,7-dimethylindenyl)hafnium dimethyl,
2,2'-propylphosphindiyl-bis(4,7-dimethylindenyl)hafnium dimethyl,
2,2'-butylphosphindiyl-bis(4,7-dimethylindenyl)hafnium dimethyl,
2,2'-(1,2-dimethyldiphosphandiyl)-bis(4,7-dimethylindenyl)hafnium dimethyl,
2,1'-phenylphosphindiyl(indenyl)(3-methylcyclopentadienyl)hafnium dimethyl,
2,1'-methylphosphindiyl(indenyl)(3-methylcyclopentadienyl)hafnium dimethyl,
2,1'-ethylphosphindiyl(indenyl)(3-methylcyclopentadienyl) hafnium dimethyl,
2,1'-propylphosphindiyl(indenyl)(3-methylcyclopentadienyl)hafnium dimethyl,
2,1'-butylphosphindiyl(indenyl)(3-methylcyclopentadienyl) hafnium dimethyl,
2,1'-(1,2-dimethyldiphosphandiyl)(indenyl)(3-methylcyclopentadieny)hafnium dimethyl,
2,1'-phenylphosphindiyl(indenyl)(2,4-dimethylcyclopentadienyl)hafnium dimethyl,
2,1'-methylphosphindiyl(indenyl)(2,4-dimethylcyclopentadienyl)hafnium dimethyl,
2,1'-ethylphosphindiyl(indenyl)(2,4-dimethylcyclopentadienyl)hafnium dimethyl,
2,1'-propylphosphindiyl(indenyl)(2,4-dimethylcyclopentadienyl)hafnium dimethyl,
2,1'-butylphosphindiyl(indenyl)(2,4-dimethylcyclopentadienyl)hafnium dimethyl,
2,1'-(1,2-dimethyldiphosphandiyl)(indenyl)(2,4-dimethylcyclopentadienyl)hafnium dimethyl,
2,1'-phenylphosphindiyl(indenyl)(2-methyl-4-butylcyclopentadienyl)hafnium dimethyl,
2,1'-methylphosphindiyl(indenyl)(2-methyl-4-butylcyclopentadienyl)hafnium dimethyl,
2,1'-ethylphosphindiyl(indenyl)(2-methyl-4-butylcyclopentadienyl)hafnium dimethyl,
2,1'-propylphosphindiyl(indenyl)(2-methyl-4-butylcyclopentadienyl)hafnium dimethyl,
2,1'-butylphosphindiyl(indenyl)(2-methyl-4-butylcyclopentadienyl)hafnium dimethyl,
2,1'-(1,2-dimethyldiphosphandiyl)(indenyl)(2-methyl-4-butylcyclopentadienyl)hafnium dimethyl,
2,9'-phenylphosphindiyl(indenyl)(fluorenyl)hafnium dimethyl,
2,9'-methylphosphindiyl(indenyl)(fluorenyl)hafnium dimethyl,
2,9'-ethylphosphindiyl(indenyl)(fluorenyl)hafnium dimethyl,
2,9'-propylphosphindiyl(indenyl)(fluorenyl)hafnium dimethyl,
2,9'-butylphosphindiyl(indenyl)(fluorenyl)hafnium dimethyl,
2,9'-(1,2-dimethyldiphosphandiyl)(indenyl)(fluorenyl) hafnium dimethyl,
2,2'-phenylphosphindiyl-bis(indenyl)hafnium dibenzyl,
2,2'-methylphosphindiyl-bis(indenyl)hafnium dibenzyl,
2,2'-ethylphosphindiyl-bis(indenyl)hafnium dibenzyl,
2,2'-propylphosphindiyl-bis(indenyl)hafnium dibenzyl,
2,2'-butylphosphindiyl-bis(indenyl)hafnium dibenzyl,
2,2'-(1,2-dimethyldiphosphandiyl)-bis(indenyl)hafnium dibenzyl,
2,1'-phenylphosphindiyl(indenyl)(cyclopentadienyl) hafnium dibenzyl,
2,1'-methylphosphindiyl(indenyl)(cyclopentadienyl) hafnium dibenzyl,
2,1'-ethylphosphindiyl(indenyl)(cyclopentadienyl)hafnium dibenzyl,
2,1'-propylphosphindiyl(indenyl)(cyclopentadienyl) hafnium dibenzyl,
2,1'-butylphosphindiyl(indenyl)(cyclopentadienyl)hafnium dibenzyl,
2,1'-1,2-dimethyldiphosphandiyl)(indenyl)(cyclopentadienyl)hafnium dibenzyl,
2,2'-phenylphosphindiyl(indenyl)(tetrahydroindenyl) hafnium dibenzyl,
2,2'-methylphosphindiyl(indenyl)(tetrahydroindenyl) hafnium dibenzyl,
2,2'-ethylphosphindiyl(indenyl)(tetrahydroindenyl)hafnium dibenzyl,
2,2'-propylphosphindiyl(indenyl)(tetrahydroindenyl) hafnium dibenzyl,
2,2'-butylphosphindiyl(indenyl)(tetrahydroindenyl)hafnium dibenzyl,
2,2'-(1,2-dimethyldiphosphandiyl)(indenyl)(tetrahydroindenyl)hafnium dibenzyl,
2,2'-phenylphosphindiyl-bis(4-phenylindenyl)hafnium dibenzyl,
2,2'-methylphosphindiyl-bis(4-phenylindenyl)hafnium dibenzyl,
2,2'-ethylphosphindiyl-bis(4-phenylindenyl)hafnium dibenzyl,
2,2'-propylphosphindiyl-bis(4-phenylindenyl)hafnium dibenzyl,
2,2'-butylphosphindiyl-bis(4-phenylindenyl)hafnium dibenzyl,
2,2'-(1,2-dimethyldiphosphandiyl)-bis(4-phenylindenyl) hafnium dibenzyl,
2,2'-phenylphosphindiyl-bis(4,7-dimethylindenyl)hafnium dibenzyl, 2,2'-methylphosphindiyl-bis(4,7-dimethylindenyl)hafnium dibenzyl,
2,2'-ethylphosphindiyl-bis(4,7-dimethylindenyl)hafnium dibenzyl,
2,2'-propylphosphindiyl-bis(4,7-dimethylindenyl)hafnium dibenzyl,
2,2'-butylphosphindiyl-bis(4,7-dimethylindenyl)hafnium dibenzyl,
2,2'-(1,2-dimethyldiphosphandiyl)-bis(4,7-dimethylindenyl)hafnium dibenzyl,
2,1'-phenylphosphindiyl(indenyl)(3-methylcyclopentadienyl)hafnium dibenzyl,
2,1'-methylphosphindiyl(indenyl)(3-methylcyclopentadienyl)hafnium dibenzyl,
2,1'-ethylphosphindiyl(indenyl)(3-methylcyclopentadienyl)hafnium dibenzyl,
2,1'-propylphosphindiyl(indenyl)(3-methylcyclopentadienyl)hafnium dibenzyl,
2,1'-butylphosphindiyl(indenyl)(3-methylcyclopentadienyl)hafnium dibenzyl,
2,1'-(1,2-dimethyldiphosphandiyl)(indenyl)(3-methylcyclopentadienyl)hafnium dibenzyl,
2,1'-phenylphosphindiyl(indenyl)(2,4-dimethylcyclopentadienyl)hafnium dibenzyl,
2,1'-methylphosphindiyl(indenyl)(2,4-dimethylcyclopentadienyl)hafnium dibenzyl,
2,1'-ethylphosphindiyl(indenyl)(2,4-dimethylcyclopentadienyl)hafnium dibenzyl,
2,1'-propylphosphindiyl(indenyl)(2,4-dimethylcyclopentadienyl)hafnium dibenzyl,
2,1'-butylphosphindiyl(indenyl)(2,4-dimethylcyclopentadienyl)hafnium dibenzyl,
2,1'-(1,2-dimethyldiphosphandiyl)(indenyl)(2,4-dimethylcyclopentadienyl)hafnium dibenzyl,
2,1'-phenylphosphindiyl(indenyl)(2-methyl-4-butylcyclopentadienyl)hafnium dibenzyl,
2,1'-methylphosphindiyl(indenyl)(2-methyl-4-butylcyclopentadienyl)hafnium dibenzyl,
2,1'-ethylphosphindiyl(indenyl)(2-methyl-4-butylcyclopentadienyl)hafnium dibenzyl,
2,1'-propylphosphindiyl(indenyl)(2-methyl-4-butylcyclopentadienyl)hafnium dibenzyl,
2,1'-butylphosphindiyl(indenyl)(2-methyl-4-butylcyclopentadienyl)hafnium dibenzyl,
2,1'-(1,2-dimethyldiphosphandiyl)(indenyl)(2-methyl-4-butylcyclopentadienyl)hafnium dibenzyl,
2,9'-phenylphosphindiyl(indenyl)(fluorenyl)hafnium dibenzyl,
2,9'-methylphosphindiyl(indenyl)(fluorenyl)hafnium dibenzyl,
2,9'-ethylphosphindiyl(indenyl)(fluorenyl)hafnium dibenzyl,
2,9'-propylphosphindiyl(indenyl)(fluorenyl)hafnium dibenzyl,
2,9'-butylphosphindiyl(indenyl)(fluorenyl)hafnium dibenzyl,
2,9'-(1,2-dimethyldiphosphandiyl)(indenyl)(fluorenyl)hafnium dibenzyl,
2,2'-phenylphosphindiyl-bis(indenyl)hafnium difluoride,
2,2'-methylphosphindiyl-bis(indenyl)hafnium difluoride,
2,2'-ethylphosphindiyl-bis(indenyl)hafnium difluoride,
2,2'-propylphosphindiyl-bis(indenyl)hafnium difluoride,
2,2'-butylphosphindiyl-bis(indenyl)hafnium difluoride,
2,2'-(1,2-dimethyldiphosphandiyl)-bis(indenyl)hafnium difluoride,
2,1'-phenylphosphindiyl(indenyl)(cyclopentadienyl)hafnium difluoride,
2,1'-methylphosphindiyl(indenyl)(cyclopentadienyl)hafnium difluoride,
2,1'-ethylphosphindiyl(indenyl)(cyclopentadienyl)hafnium difluoride,
2,1'-propylphosphindiyl(indenyl)(cyclopentadienyl)hafnium difluoride,
2,1'-butylphosphindiyl(indenyl)(cyclopentadienyl)hafnium difluoride,
2,1'-(1,2-dimethyldiphosphandiyl)(indenyl)(cyclopentadienyl)hafnium difluoride,
2,2'-phenylphosphindiyl(indenyl)(tetrahydroindenyl)hafnium difluoride,
2,2'-methylphosphindiyl(indenyl)(tetrahydroindenyl)hafnium difluoride,
2,2'-ethylphosphindiyl(indenyl)(tetrahydroindenyl)hafnium difluoride,
2,2'-propylphosphindiyl(indenyl)(tetrahydroindenyl)hafnium difluoride,
2,2'-butylphosphindiyl(indenyl)(tetrahydroindenyl)hafnium difluoride,
2,2'-(1,2-dimethyldiphosphandiyl)(indenyl)(tetrahydroindenyl)hafnium difluoride,
2,2'-phenylphosphindiyl-bis(4-phenylindenyl)hafnium difluoride,
2,2'-methylphosphindiyl-bis(4-phenylindenyl)hafnium difluoride,
2,2'-ethylphosphindiyl-bis(4-phenylindenyl)hafnium difluoride,
2,2'-propylphosphindiyl-bis(4-phenylindenyl)hafnium difluoride,
2,2'-butylphosphindiyl-bis(4-phenylindenyl)hafnium difluoride,
2,2'-(1,2-dimethyldiphosphandiyl)-bis(4-phenylindenyl)hafnium difluoride,
2,2'-phenylphosphindiyl-bis(4,7-dimethylindenyl)hafnium difluoride,
2,2'-methylphosphindiyl-bis(4,7-dimethylindenyl)hafnium difluoride,
2,2'-ethylphosphindiyl-bis(4,7-dimethylindenyl)hafnium difluoride,
2,2'-propylphosphindiyl-bis(4,7-dimethylindenyl)hafnium difluoride,
2,2'-butylphosphindiyl-bis(4,7-dimethylindenyl)hafnium difluoride,
2,2'-(1,2-dimethyldiphosphandiyl)-bis(4,7-dimethylindenyl)hafnium difluoride,
2,1'-phenylphosphindiyl(indenyl)(3-methylcyclopentadienyl)hafnium difluoride,
2,1'-methylphosphindiyl(indenyl)(3-methylcyclopentadienyl)hafnium difluoride,
2,1'-ethylphosphindiyl(indenyl)(3-methylcyclopentadienyl)hafnium difluoride,
2,1'-propylphosphindiyl(indenyl)(3-methylcyclopentadienyl)hafnium difluoride,
2,1'-butylphosphindiyl(indenyl)(3-methylcyclopentadienyl)hafnium difluoride,
2,1'-(1,2-dimethyldiphosphandiyl)(indenyl)(3-methylcyclopentadienyl)hafnium difluoride,
2,1'-phenylphosphindiyl(indenyl)(2,4-dimethylcyclopentadienyl)hafnium difluoride,
2,1'-methylphosphindiyl(indenyl)(2,4-dimethylcyclopentadienyl)hafnium difluoride,
2,1'-ethylphosphindiyl(indenyl)(2,4-dimethylcyclopentadienyl)hafnium difluoride,
2,1'-propylphosphindiyl(indenyl)(2,4-dimethylcyclopentadienyl)hafnium difluoride, 2,1'-butylphosphindiyl(indenyl)(2,4-dimethylcyclopentadienyl)hafnium difluoride,
2,1'-(1,2-dimethyldiphosphandiyl)(indenyl)(2,4-dimethylcyclopentadienyl)hafnium difluoride,
2,1'-phenylphosphindiyl(indenyl)(2-methyl-4-butylcyclopentadienyl)hafnium difluoride,
2,1'-methylphosphindiyl(indenyl)(2-methyl-4-butylcyclopentadienyl)hafnium difluoride,
2,1'-ethylphosphindiyl(indenyl)(2-methyl-4-butylcyclopentadienyl)hafnium difluoride,
2,1'-propylphosphindiyl(indenyl)(2-methyl-4-butylcyclopentadienyl)hafnium difluoride,
2,1'-butylphosphindiyl(indenyl)(2-methyl-4-butylcyclopentadienyl)hafnium difluoride,
2,1'-(1,2-dimethyldiphosphandiyl)(indenyl)(2-methyl-4-butylcyclopentadienyl)hafnium difluoride,
2,9'-phenylphosphindiyl(indenyl)(fluorenyl)hafnium difluoride,
2,9'-methylphosphindiyl(indenyl)(fluorenyl)hafnium difluoride,
2,9'-ethylphosphindiyl(indenyl)(fluorenyl)hafnium difluoride,
2,9'-propylphosphindiyl(indenyl)(fluorenyl)hafnium difluoride,
2,9'-butylphosphindiyl(indenyl)(fluorenyl)hafnium difluoride,
2,9'-(1,2-dimethyldiphosphandiyl)(indenyl)(fluorenyl) hafnium difluoride,
2,2'-phenylphosphindiyl-bis(indenyl)titanium dichloride,
2,2'-methylphosphindiyl-bis(indenyl)titanium dichloride,
2,2'-ethylphosphindiyl-bis(indenyl)titanium dichloride,
2,2'-propylphosphindiyl-bis(indenyl)titanium dichloride,
2,2'-butylphosphindiyl-bis(indenyl)titanium dichloride,
2,2'-(1,2-dimethyldiphosphandiyl)-bis(indenyl)titanium dichloride,
2,1'-phenylphosphindiyl(indenyl)(cyclopentadienyl)titanium dichloride,
2,1'-methylphosphindiyl(indenyl)(cyclopentadienyl)titanium dichloride,
2,1'-ethylphosphindiyl(indenyl)(cyclopentadienyl)titanium dichloride,
2,1'-propylphosphindiyl(indenyl)(cyclopentadienyl)titanium dichloride,
2,1'-butylphosphindiyl(indenyl)(cyclopentadienyl)titanium dichloride,
2,1'-1,2-dimethyldiphosphandiyl)(indenyl)(cyclopentadienyl)titanium dichloride,
2,2'-phenylphosphindiyl(indenyl)(tetrahydroindenyl)titanium dichloride,
2,2'-methylphosphindiyl(indenyl)(tetrahydroindenyl)titanium dichloride,
2,2'-ethylphosphindiyl(indenyl)(tetrahydroindenyl)titanium dichloride,
2,2'-propylphosphindiyl(indenyl)(tetrahydroindenyl)titanium dichloride,
2,2'-butylphosphindiyl(indenyl)(tetrahydroindenyl)titanium dichloride,
2,2'-(1,2-dimethyldiphosphandiyl)(indenyl)(tetrahydroindenyl)titanium dichloride,
2,2'-phenylphosphindiyl-bis(4-phenylindenyl)titanium dichloride,
2,2'-methylphosphindiyl-bis(4-phenylindenyl)titanium dichloride,
2,2'-ethylphosphindiyl-bis(4-phenylindenyl)titanium dichloride,
2,2'-propylphosphindiyl-bis(4-phenylindenyl)titanium dichloride,
2,2'-butylphosphindiyl-bis(4-phenylindenyl)titanium dichloride,
2,2'-(1,2-dimethyldiphosphandiyl)-bis(4-phenylindenyl)titanium dichloride,
2,2'-phenylphosphindiyl-bis(4,7-dimethylindenyl)titanium dichloride,
2,2'-methylphosphindiyl-bis(4,7-dimethylindenyl)titanium dichloride,
2,2'-ethylphosphindiyl-bis(4,7-dimethylindenyl)titanium dichloride,
2,2'-propylphosphindiyl-bis(4,7-dimethylindenyl)titanium dichloride,
2,2'-butylphosphindiyl-bis(4,7-dimethylindenyl)titanium dichloride,
2,2'-(1,2-dimethyldiphosphandiyl)-bis(4,7-dimethylindenyl)titanium dichloride,
2,1'-phenylphosphindiyl(indenyl)(3-methylcyclopentadienyl)titanium dichloride,
2,1'-methylphosphindiyl(indenyl)(3-methylcyclopentadienyl)titanium dichloride,
2,1'-ethylphosphindiyl(indenyl)(3-methylcyclopentadienyl) titanium dichloride,
2,1'-propylphosphindiyl(indenyl)(3-methylcyclopentadienyl)titanium dichloride,
2,1'-butylphosphindiyl(indenyl)(3-methylcyclopentadienyl) titanium dichloride,
2,1'-(1,2-dimethyldiphosphandiyl)(indenyl)(3-methylcyclopentadienyl)titanium dichloride,
2,1'-phenylphosphindiyl(indenyl)(2,4-dimethylcyclopentadienyl)titanium dichloride,
2,1'-methylphosphindiyl(indenyl)(2,4-dimethylcyclopentadienyl)titanium dichloride,
2,1'-ethylphosphindiyl(indenyl)(2,4-dimethylcyclopentadienyl)titanium dichloride,
2,1'-propylphosphindiyl(indenyl)(2,4-dimethylcyclopentadienyl)titanium dichloride,
2,1'-butylphosphindiyl(indenyl)(2,4-dimethylcyclopentadienyl)titanium dichloride,
2,1'-(1,2-dimethyldiphosphandiyl)(indenyl)(2,4-dimethylcyclopentadienyl)titanium dichloride,
2,1'-phenylphosphindiyl(indenyl)(2-methyl-4-butylcyclopentadienyl)titanium dichloride,
2,1'-methylphosphindiyl(indenyl)(2-methyl-4-butylcyclopentadienyl)titanium dichloride,
2,1'-ethylphosphindiyl(indenyl)(2-methyl-4-butylcyclopentadienyl)titanium dichloride,
2,1'-propylphosphindiyl(indenyl)(2-methyl-4-butylcyclopentadienyl)titanium dichloride,
2,1'-butylphosphindiyl(indenyl)(2-methyl-4-butylcyclopentadienyl)titanium dichloride,
2,1'-(1,2-dimethyldiphosphandiyl)(indenyl)(2-methyl-4-butylcyclopentadienyl)titanium dichloride,
2,9'-phenylphosphindiyl(indenyl)(fluorenyl)titanium dichloride,
2,9'-methylphosphindiyl(indenyl)(fluorenyl)titanium dichloride,
2,9'-ethylphosphindiyl(indenyl)(fluorenyl)titanium dichloride,
2,9'-propylphosphindiyl(indenyl)(fluorenyl)titanium dichloride,
2,9'-butylphosphindiyl(indenyl)(fluorenyl)titanium dichloride,
2,9'-(1,2-dimethyldiphosphandiyl)(indenyl)(fluorenyl)titanium dichloride,
2,2'-phenylphosphindiyl-bis(indenyl)titanium dimethyl,
2,2'-methylphosphindiyl-bis(indenyl)titanium dimethyl,
2,2'-ethylphosphindiyl-bis(indenyl)titanium dimethyl, 2,2'-propylphosphindiyl-bis(indenyl)titanium dimethyl,
2,2'-butylphosphindiyl-bis(indenyl)titanium dimethyl,
2,2'-(1,2-dimethyldiphosphandiyl)-bis(indenyl)titanium dimethyl,
2,1'-phenylphosphindiyl(indenyl)(cyclopentadienyl)titanium dimethyl,
2,1'-methylphosphindiyl(indenyl)(cyclopentadienyl)titanium dimethyl,
2,1'-ethylphosphindiyl(indenyl)(cyclopentadienyl)titanium dimethyl,
2,1'-propylphosphindiyl(indenyl)(cyclopentadienyl)titanium dimethyl,
2,1'-butylphosphindiyl(indenyl)(cyclopentadienyl)titanium dimethyl,
2,1'-1,2-dimethyldiphosphandiyl)(indenyl)(cyclopentadienyl)titanium dimethyl,
2,2'-phenylphosphindiyl(indenyl)(tetrahydroindenyl)titanium dimethyl,
2,2'-methylphosphindiyl(indenyl)(tetrahydroindenyl)titanium dimethyl,
2,2'-ethylphosphindiyl(indenyl)(tetrahydroindenyl)titanium dimethyl,
2,2'-propylphosphindiyl(indenyl)(tetrahydroindenyl)titanium dimethyl,
2,2'-butylphosphindiyl(indenyl)(tetrahydroindenyl)titanium dimethyl,
2,2'-(1,2-dimethyldiphosphandiyl)(indenyl)(tetrahydroindenyl)titanium dimethyl,
2,2'-phenylphosphindiyl-bis(4-phenylindenyl)titanium dimethyl,
2,2'-methylphosphindiyl-bis(4-phenylindenyl)titanium dimethyl,
2,2'-ethylphosphindiyl-bis(4-phenylindenyl)titanium dimethyl,
2,2'-propylphosphindiyl-bis(4-phenylindenyl)titanium dimethyl,
2,2'-butylphosphindiyl-bis(4-phenylindenyl)titanium dimethyl,
2,2'-(1,2-dimethyldiphosphandiyl)-bis(4-phenylindenyl)titanium dimethyl,
2,2'-phenylphosphindiyl-bis(4,7-dimethylindenyl)titanium dimethyl,
2,2'-methylphosphindiyl-bis(4,7-dimethylindenyl)titanium dimethyl,
2,2'-ethylphosphindiyl-bis(4,7-dimethylindenyl)titanium dimethyl,
2,2'-propylphosphindiyl-bis(4,7-dimethylindenyl)titanium dimethyl,
2,2'-butylphosphindiyl-bis(4,7-dimethylindenyl)titanium dimethyl,
2,2'-(1,2-dimethyldiphosphandiyl)-bis(4,7-dimethylindenyl)titanium dimethyl,
2,1'-phenylphosphindiyl(indenyl)(3-methylcyclopentadienyl)titanium dimethyl,
2,1'-methylphosphindiyl(indenyl)(3-methylcyclopentadienyl)titanium dimethyl,
2,1'-ethylphosphindiyl(indenyl)(3-methylcyclopentadienyl)titanium dimethyl,
2,1'-propylphosphindiyl(indenyl)(3-methylcyclopentadienyl)titanium dimethyl,
2,1'-butylphosphindiyl(indenyl)(3-methylcyclopentadienyl)titanium dimethyl,
2,1'-(1,2-dimethyldiphosphandiyl)(indenyl)(3-methylcyclopentadienyl)titanium dimethyl,
2,1'-phenylphosphindiyl(indenyl)(2,4-dimethylcyclopentadienyl)titanium dimethyl,
2,1'-methylphosphindiyl(indenyl)(2,4-dimethylcyclopentadienyl)titanium dimethyl,
2,1'-ethylphosphindiyl(indenyl)(2,4-dimethylcyclopentadienyl)titanium dimethyl,
2,1'-propylphosphindiyl(indenyl)(2,4-dimethylcyclopentadienyl)titanium dimethyl,
2,1'-butylphosphindiyl(indenyl)(2,4-dimethylcyclopentadienyl)titanium dimethyl,
2,1'-(1,2-dimethyldiphosphandiyl)(indenyl)(2,4-dimethylcyclopentadienyl)titanium dimethyl,
2,1'-phenylphosphindiyl(indenyl)(2-methyl-4-butylcyclopentadienyl)titanium dimethyl,
2,1'-methylphosphindiyl(indenyl)(2-methyl-4-butylcyclopentadienyl)titanium dimethyl,
2,1'-ethylphosphindiyl(indenyl)(2-methyl-4-butylcyclopentadienyl)titanium dimethyl,
2,1'-propylphosphindiyl(indenyl)(2-methyl-4-butylcyclopentadienyl)titanium dimethyl,
2,1'-butylphosphindiyl(indenyl)(2-methyl-4-butylcyclopentadienyl)titanium dimethyl,
2,1'-(1,2-dimethyldiphosphandiyl)(indenyl)(2-methyl-4-butylcyclopentadienyl)titanium dimethyl,
2,9'-phenylphosphindiyl(indenyl)(fluorenyl)titanium dimethyl,
2,9'-methylphosphindiyl(indenyl)(fluorenyl)titanium dimethyl,
2,9'-ethylphosphindiyl(indenyl)(fluorenyl)titanium dimethyl,
2,9'-propylphosphindiyl(indenyl)(fluorenyl)titanium dimethyl,
2,9'-butylphosphindiyl(indenyl)(fluorenyl)titanium dimethyl,
2,9'-(1,2-dimethyldiphosphandiyl)(indenyl)(fluorenyl)titanium dimethyl,
2,2'-phenylphosphindiyl-bis(indenyl)titanium dibenzyl,
2,2'-methylphosphindiyl-bis(indenyl)titanium dibenzyl,
2,2'-ethylphosphindiyl-bis(indenyl)titanium dibenzyl,
2,2'-propylphosphindiyl-bis(indenyl)titanium dibenzyl,
2,2'-butylphosphindiyl-bis(indenyl)titanium dibenzyl,
2,2'-(1,2-dimethyldiphosphandiyl)-bis(indenyl)titanium dibenzyl,
2,1'-phenylphosphindiyl(indenyl)(cyclopentadienyl)titanium dibenzyl,
2,1'-methylphosphindiyl(indenyl)(cyclopentadienyl)titanium dibenzyl,
2,1'-ethylphosphindiyl(indenyl)(cyclopentadienyl)titanium dibenzyl,
2,1'-propylphosphindiyl(indenyl)(cyclopentadienyl)titanium dibenzyl,
2,1'-butylphosphindiyl(indenyl)(cyclopentadienyl)titanium dibenzyl,
2,1'-1,2-dimethyldiphosphandiyl)(indenyl)(cyclopentadienyl)titanium dibenzyl,
2,2'-phenylphosphindiyl(indenyl)(tetrahydroindenyl)titanium dibenzyl,
2,2'-methylphosphindiyl(indenyl)(tetrahydroindenyl)titanium dibenzyl,
2,2'-ethylphosphindiyl(indenyl)(tetrahydroindenyl)titanium dibenzyl,
2,2'-propylphosphindiyl(indenyl)(tetrahydroindenyl)titanium dibenzyl,
2,2'-butylphosphindiyl(indenyl)(tetrahydroindenyl)titanium dibenzyl,
2,2'-(1,2-dimethyldiphosphandiyl)(indenyl)(tetrahydroindenyl)titanium dibenzyl,
2,2'-phenylphosphindiyl-bis(4-phenylindenyl)titanium dibenzyl, 2,2'-methylphosphindiyl-bis(4-phenylindenyl)titanium dibenzyl,
2,2'-ethylphosphindiyl-bis(4-phenylindenyl)titanium dibenzyl,
2,2'-propylphosphindiyl-bis(4-phenylindenyl)titanium dibenzyl,
2,2'-butylphosphindiyl-bis(4-phenylindenyl)titanium dibenzyl,
2,2'-(1,2-dimethyldiphosphandiyl)-bis(4-phenylindenyl)titanium dibenzyl,
2,2'-phenylphosphindiyl-bis(4,7-dimethylindenyl)titanium dibenzyl,
2,2'-methylphosphindiyl-bis(4,7-dimethylindenyl)titanium dibenzyl,
2,2'-ethylphosphindiyl-bis(4,7-dimethylindenyl)titanium dibenzyl,
2,2'-propylphosphindiyl-bis(4,7-dimethylindenyl)titanium dibenzyl,
2,2'-butylphosphindiyl-bis(4,7-dimethylindenyl)titanium dibenzyl,
2,2'-(1,2-dimethyldiphosphandiyl)-bis(4,7-dimethylindenyl)titanium dibenzyl,
2,1'-phenylphosphindiyl(indenyl)(3-methylcyclopentadienyl)titanium dibenzyl,
2,1'-methylphosphindiyl(indenyl)(3-methylcyclopentadienyl)titanium dibenzyl,
2,1'-ethylphosphindiyl(indenyl)(3-methylcyclopentadienyl)titanium dibenzyl,
2,1'-propylphosphindiyl(indenyl)(3-methylcyclopentadienyl)titanium dibenzyl,
2,1'-butylphosphindiyl(indenyl)(3-methylcyclopentadienyl)titanium dibenzyl,
2,1'-(1,2-dimethyldiphosphandiyl)(indenyl)(3-methylcyclopentadienyl)titanium dibenzyl,
2,1'-phenylphosphindiyl(indenyl)(2,4-dimethylcyclopentadienyl)titanium dibenzyl,
2,1'-methylphosphindiyl(indenyl)(2,4-dimethylcyclopentadienyl)titanium dibenzyl,
2,1'-ethylphosphindiyl(indenyl)(2,4-dimethylcyclopentadienyl)titanium dibenzyl,
2,1'-propylphosphindiyl(indenyl)(2,4-dimethylcyclopentadienyl)titanium dibenzyl,
2,1'-butylphosphindiyl(indenyl)(2,4-dimethylcyclopentadienyl)titanium dibenzyl,
2,1'-(1,2-dimethyldiphosphandiyl)(indenyl)(2,4-dimethylcyclopentadienyl)titanium dibenzyl,
2,1'-phenylphosphindiyl(indenyl)(2-methyl-4-butylcyclopentadienyl)titanium dibenzyl,
2,1'-methylphosphindiyl(indenyl)(2-methyl-4-butylcyclopentadienyl)titanium dibenzyl,
2,1'-ethylphosphindiyl(indenyl)(2-methyl-4-butylcyclopentadienyl)titanium dibenzyl,
2,1'-propylphosphindiyl(indenyl)(2-methyl-4-butylcyclopentadienyl)titanium dibenzyl,
2,1'-butylphosphindiyl(indenyl)(2-methyl-4-butylcyclopentadienyl)titanium dibenzyl,
2,1'-(1,2-dimethyldiphosphandiyl)(indenyl)(2-methyl-4-butylcyclopentadienyl)titanium dibenzyl,
2,9'-phenylphosphindiyl(indenyl)(fluorenyl)titanium dibenzyl,
2,9'-methylphosphindiyl(indenyl)(fluorenyl)titanium dibenzyl,
2,9'-ethylphosphindiyl(indenyl)(fluorenyl)titanium dibenzyl,
2,9'-propylphosphindiyl(indenyl)(fluorenyl)titanium dibenzyl,
2,9'-butylphosphindiyl(indenyl)(fluorenyl)titanium dibenzyl,
2,9'-(1,2-dimethyldiphosphandiyl)(indenyl)(fluorenyl)titanium dibenzyl,
2,2'-phenylphosphindiyl-bis(indenyl)titanium difluoride,
2,2'-methylphosphindiyl-bis(indenyl)titanium difluoride,
2,2'-ethylphosphindiyl-bis(indenyl)titanium difluoride,
2,2'-propylphosphindiyl-bis(indenyl)titanium difluoride,
2,2'-butylphosphindiyl-bis(indenyl)titanium difluoride,
2,2'-(1,2-dimethyldiphosphandiyl)-bis(indenyl)titanium difluoride,
2,1'-phenylphosphindiyl(indenyl)(cyclopentadienyl)titanium difluoride,
2,1'-methylphosphindiyl(indenyl)(cyclopentadienyl)titanium difluoride,
2,1'-ethylphosphindiyl(indenyl)(cyclopentadienyl)titanium difluoride,
2,1'-propylphosphindiyl(indenyl)(cyclopentadienyl)titanium difluoride,
2,1'-butylphosphindiyl(indenyl)(cyclopentadienyl)titanium difluoride,
2,1'-1,2-dimethyldiphosphandiyl)(indenyl)(cyclopentadienyl)titanium difluoride,
2,2'-phenylphosphindiyl(indenyl)(tetrahydroindenyl)titanium difluoride,
2,2'-methylphosphindiyl(indenyl)(tetrahydroindenyl)titanium difluoride,
2,2'-ethylphosphindiyl(indenyl)(tetrahydroindenyl)titanium difluoride,
2,2'-propylphosphindiyl(indenyl)(tetrahydroindenyl)titanium difluoride,
2,2'-butylphosphindiyl(indenyl)(tetrahydroindenyl)titanium difluoride,
2,2'-(1,2-dimethyldiphosphandiyl)(indenyl)(tetrahydroindenyl)titanium difluoride,
2,2'-phenylphosphindiyl-bis(4-phenylindenyl)titanium difluoride,
2,2'-methylphosphindiyl-bis(4-phenylindenyl)titanium difluoride,
2,2'-ethylphosphindiyl-bis(4-phenylindenyl)titanium difluoride,
2,2'-propylphosphindiyl-bis(4-phenylindenyl)titanium difluoride,
2,2'-butylphosphindiyl-bis(4-phenylindenyl)titanium difluoride,
2,2'-(1,2-dimethyldiphosphandiyl)-bis(4-phenylindenyl)titanium difluoride,
2,2'-phenylphosphindiyl-bis(4,7-dimethylindenyl)titanium difluoride,
2,2'-methylphosphindiyl-bis(4,7-dimethylindenyl)titanium difluoride,
2,2'-ethylphosphindiyl-bis(4,7-dimethylindenyl)titanium difluoride,
2,2'-propylphosphindiyl-bis(4,7-dimethylindenyl)titanium difluoride,
2,2'-butylphosphindiyl-bis(4,7-dimethylindenyl)titanium difluoride,
2,2'-(1,2-dimethyldiphosphandiyl)-bis(4,7-dimethylindenyl)titanium difluoride,
2,1'-phenylphosphindiyl(indenyl)(3-methylcyclopentadienyl)titanium difluoride,
2,1'-methylphosphindiyl(indenyl)(3-methylcyclopentadienyl)titanium difluoride,
2,1'-ethylphosphindiyl(indenyl)(3-methylcyclopentadienyl) titanium difluoride,
2,1'-propylphosphindiyl(indenyl)(3-methylcyclopentadienyl)titanium difluoride, 2,1'-butylphosphindiyl(indenyl)(3-methylcyclopentadienyl)titanium difluoride,
2,1'-(1,2-dimethyldiphosphandiyl)(indenyl)(3-methylcyclopentadienyl)titanium difluoride,
2,1'-phenylphosphindiyl(indenyl)(2,4-dimethylcyclopentadienyl)titanium difluoride,
2,1'-methylphosphindiyl(indenyl)(2,4-dimethylcyclopentadienyl)titanium difluoride,
2,1'-ethylphosphindiyl(indenyl)(2,4-dimethylcyclopentadienyl)titanium difluoride,
2,1'-propylphosphindiyl(indenyl)(2,4-dimethylcyclopentadienyl)titanium difluoride,
2,1'-butylphosphindiyl(indenyl)(2,4-dimethylcyclopentadienyl)titanium difluoride,
2,1'-(1,2-dimethyldiphosphandiyl)(indenyl)(2,4-dimethylcyclopentadienyl)titanium difluoride,
2,1'-phenylphosphindiyl(indenyl)(2-methyl-4-butylcyclopentadienyl)titanium difluoride,
2,1'-methylphosphindiyl(indenyl)(2-methyl-4-butylcyclopentadienyl)titanium difluoride,
2,1'-ethylphosphindiyl(indenyl)(2-methyl-4-butylcyclopentadienyl)titanium difluoride,
2,1'-propylphosphindiyl(indenyl)(2-methyl-4-butylcyclopentadienyl)titanium difluoride,
2,1'-butylphosphindiyl(indenyl)(2-methyl-4-butylcyclopentadienyl)titanium difluoride,
2,1'-(1,2-dimethyldiphosphandiyl)(indenyl)(2-rhethyl-4-butylcyclopentadienyl)titanium difluoride,
2,9'-phenylphosphindiyl(indenyl)(fluorenyl)titanium difluoride,
2,9'-methylphosphindiyl(indenyl)(fluorenyl)titanium difluoride,
2,9'-ethylphosphindiyl(indenyl)(fluorenyl)titanium difluoride,
2,9'-propylphosphindiyl(indenyl)(fluorenyl)titanium difluoride,
2,9'-butylphosphindiyl(indenyl)(fluorenyl)titanium difluoride,
2,9'-(1,2-dimethyldiphosphandiyl)(indenyl)(fluorenyl)titanium difluoride, and the like.

Mixed Catalysts

Mixed catalyst systems can also be used, for example, the invention catalyst can be used in conjunction with a "second catalyst" in the same reactor or in a series of reactors where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Invention polymerization catalyst systems can comprise additional olefin polymerization catalysts, sometimes referred to as the "second catalyst". These additional olefin polymerization catalysts are any of those well known in the art to catalyze the olefin to polyolefin reaction. Some invention catalysts systems include Group-4–6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359–370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5–10 transition-metal centers are known and can serve as the additional olefin polymerization catalysts with invention catalyst systems. Invention catalyst systems can use non-cyclopentadienyl, Group-4–5 precursor compounds as the additional olefin polymerization catalysts. Non-cyclopentadienyl, Group-4–5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154–3156. U.S. Pat. No. 5,318,935 describes bridged and unbridged, bis-amido catalyst compounds of Group-4 metals capable of □-olefins polymerization. Bridged bis(arylamido) Group-4 compounds for olefin polymerization are described by D. H. McConville, et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408050, filed 29 Sep. 1999, and its equivalent PCT/US99/22690. A monoanionic bidentate ligand and two monoanionic ligands stabilize those catalyst precursors; they are activable with this invention" ionic cocatalysts. Other suitable Group-4–5 non-metallocene catalysts are bimetallocyclic catalyst compounds comprising two independently selected Group-4–5 metal atoms directly linked through two bridging groups to form cyclic compounds.

Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)- Based Catalysts for Polymerization of Ethylene and α-Olefins", M. Brookhart, et al, *J. Am. Chem. Soc.*, 1995, 117, 6414–6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.*, 849–850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Activators and Catalyst Activation

The catalyst precursors, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such trimethyl aluminum, tri-isobutyl aluminum, triethyl aluminum, and tri-isopropyl aluminum. Co-activators are typically only used in combination with Lewis acid activators and ionic activators when the pre-catalyst is not a dihydrocarbyl or dihydride complex.

The alumoxane component useful as an activator typically is an oligomeric aluminum compound represented by the general formula $(R^x-Al-O)_n$, which is a cyclic compound, or $R^x(R^x-Al-O)_n AlR^x_2$, which is a linear compound. In the general alumoxane formula, $R^x$ is independently a $C1-C_{20}$ alkyl radical, for example, methyl, ethyl, propyl, butyl, pentyl, isomers thereof, and the like, and "n" is an integer from 1–50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3-3,5-(CF_3)_2))_4]$, $[Ph_3C][B((C_6H_3-3,5-(CF_3)_2))_4]$, $[NH_4][B(C_6H_5)_4]$ or Lewis acidic activators such as $B(C_6F_5)_3$ or $B(C_6H_5)_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri (n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_5)_3$, which upon reaction with the hydrolyzable ligand (X') of the transition metal compound forms an anion, such as ([B$(C_6F_5)_3(X')]^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

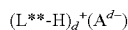

$(L^{}-H)_d^+(A^{d-})$ wherein L is an neutral Lewis base;
H is hydrogen;
$(L^{**}-H)^+$ is a Bronsted acid
$A^{d-}$ is a non-coordinating anion having the charge d−
d is an integer from 1 to 3.

The cation component, $(L^{**}-H)_d^+$ may include Bronsted acids such as protons or protonated Lewis bases or reducible Lewis acids capable of protonating or abstracting a moiety, such as an alkyl or aryl, from the precatalyst after alkylation.

The activating cation $(L^{}-H)_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}-H)_d^+$ may also be a moiety such as silver, tropylium, carbeniums, ferroceniums and mixtures, preferably carboniums and ferroceniums; most preferably triphenyl carbonium.

The anion component $A^{d-}$ include those having the formula $[M^{k+}Q_n]^{d-}$ wherein k is an integer from 1 to 3; n is an integer from 2–6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl) borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl) borate, benzene(diazonium) tetrakis-(2,3,4,6-tetrafluorophenyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

Most preferably, the ionic stoichiometric activator (L**-H)$_d^+$(A$^{d-}$) is N,N-dimethylanilinium tetrakis(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst pre-cursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst pre-cursor and the co-activator. For example, tris(pentafluorophenyl) boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391–1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris(pentafluorophenyl)boron In some embodiments, scavenging compounds are used with stoichiometric activators. Typical aluminum or boron alkyl components useful as scavengers are represented by the general formula R$^x$JZ$_2$ where J is aluminum or boron, R$^x$ is as previously defined above, and each Z is independently R$^x$ or a different univalent anionic ligand such as halogen (Cl, Br, I), alkoxide (OR$^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

The solubility of invention catalyst precursors allows for the ready preparation of supported catalysts. To prepare uniform supported catalysts, the catalyst precursor preferably dissolves in the chosen solvent. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100–200% of the pore volume). The mixture is optionally heated from 30–200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100–200% of the pore volume). After stirring, the residual solvent is removed under vacuum, typically at ambient temperature and over 10–16 hours. But greater or lesser times and temperatures are possible. The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100–200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10–700 $m^2/g$, a pore volume of 0.1–4.0 cc/g and an average particle size of 10–500 μm. Some embodiments select a surface area of 50–500 $m^2/g$, a pore volume of 0.5–3.5 cc/g, or an average particle size of 20–200 μm. Other embodiments select a surface area of 100–400 $m^2/g$, a pore volume of 0.8–3.0 cc/g, and an average particle size of 30–100 μm. Invention carriers typically have a pore size of 10–1000 Angstroms, alternatively 50–500 Angstroms, or 75–350 Angstroms.

Invention catalysts are generally deposited on the support at a loading level of 10–100 micromoles of catalyst precursor per gram of solid support; alternately 20–80 micromoles of catalyst precursor per gram of solid support; or 40–60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1,3-methylpentene-1,3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1, 3-methylpentene-1, 3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1, 3-methylpentene-1, and 3,5,5-trimethylhexene-1.

In a preferred embodiment the copolymers described herein comprise at least 50 mole % of a first monomer and up to 50 mole % of other monomers.

In another embodiment, the polymer comprises:
a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69–6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$–$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [Me$_2$HNPh]$^+$[B(pfp)$_4$]$^-$ or B(Pfp)$_3$ (perfluorophenyl=pfp=C$_6$F$_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10–30,000 MPa), in which the monomer acts as diluent or in solution polymerization using a solvent. Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1–16,000 MPa), most preferably from 1.0 to 500 bar (10–5000MPa).

Each of these processes may also be employed in single reactor, parallel or series reactor configurations. The liquid processes comprise contacting olefin monomers with the above described catalyst system in a suitable diluent or solvent and allowing said monomers to react to a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See US patent applications 60/431,185 filed Dec. 5, 2002; 60/431,077, filed Dec. 5, 2002; and 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

Experimental—Synthesis of Pre-catalysts

All manipulations with air and moisture sensitive compounds were performed either in an atmosphere of thoroughly purified argon using a standard Schlenk technique or in a controlled atmosphere Glove Box (Vacuum Atmospheres Co.). Tetrahydrofuran (THF, Merck=Merck KGaA, Darmstadt, Germany) and diethyl ether (ether, Merck) for synthesis were purified by distillation over $LiAlH_4$, and stored over sodium benzophenone ketyl under an inert atmosphere; prior to use, the solvents were distilled from the benzophenone ketyl. Hydrocarbon solvents such as benzene (Merck), toluene (Merck) and hexanes (Merck) were typically distilled over $CaH_2$, and were stored over Na/K alloy under an inert atmosphere; prior to use, the solvents were distilled from the Na/K alloy. Methylene chloride-$d_2$ was distilled and stored over $CaH_2$ under an inert atmosphere; prior to use, the solvent was distilled from the $CaH_2$. Chloroform-d was distilled over $P_4O_{10}$ and stored over molecular sieves (3 Å). Iodobenzene (Acros=Acros Organics), indene, tech. (Acros), triethyl phosphite (Acros), LiAlH$_4$ (Aldrich=Aldrich Chemical Co.), PCl$_5$ (Merck), HSiCl$_3$ (Aldrich), NaN(TMS)$_2$ (Aldrich, TMS=trimethylsilyl), NiCl$_2$ (Alfa Aesar), MeLi in ether (Aldrich), and $^t$BuMgCl in ether (Aldrich) were used as obtained. Triethylamine (Acros) was dried with CaH$_2$, then was distilled from sodium. 2-Bromo-1H-indene [1,2], Pd(PPh$_3$)$_4$ [4], ZrCl$_4$(THF)$_2$ [5], and $^t$BuPH$_2$ [7] were prepared according to the published methods ([1]. McEwen, I.; Rönnqvist, M.; Ahlberg, P. *J. Am. Chem. Soc.* 1993, 115, 3989; [2]. Halterman, R. L.; Fahey, D. R.; Bailly, E. F.; Dockter, D. W.; Stenzel, O.; Shipman, J. L.; Khan, M. A.; Dechert, S.; Schumann, H. *Organometallics* 2000, 19, 5464; [4]. Coulson, D. R. *Inorg. Synth.* 1972, 13, 121; [5]. Manzer, L. E. *Inorg. Synth.* 1982, 22, 135; [7]. Becker, G.; Rossler, O.; Schneider, E. *Z. Anorg. Allg. Chem.* 1978, 443, 42.

Analytical and semi-preparative liquid chromatography was performed using Waters Delta 600 HPLC system including 996 Photodiode Array Detector, Nova-Pack C18 or HR Silica (60A, 6 μm, 3.9 and 19×300 mm) and Symmetry C18 (5 μm, 4.6×250 mm) columns. MPHPLC was performed using MPHPLC glass columns and fittings (Ace Glass), PD5130 pump drive equipped with J1 gear-well pump head (Heidolph), 996 Photodiode Array Detector and Fraction Collector II (Waters Corp.).

$^1$H, $^{13}$C, and $^{31}$P spectra were recorded with a Brucker DPX-300 for 1–10% solutions in deuterated solvents. Chemical shifts for $^1$H and $^{13}$C were measured relatively to tetramethylsilane (TMS). Chemical shifts for $^{31}$P were measured relatively to H$_3$PO$_4$. In $^1$H NMR spectra, the assignment was made on the evidence of double resonance and Nuclear Overhauser Effect (NOE) experiments. C, H microanalyses were done using CHN-O-Rapid analyzer (Heraecus Ltd., Banau, Germany).

Trichloro(1H-iden-2-yl)phosphonium hexachlorophosphate (1-) (1).

Trichloro(1 H-inden-2-yl)phosphonium hexachlorophosphate(1-) (1).

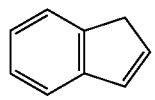  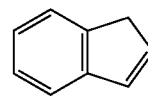

1

To a suspension of 154 g (0.74 mol) of PCl$_5$ in 200 ml of toluene, a solution of 48.2 ml (43.0 g, 0.37 mol) of indene (tech., 90%) in 30 ml of toluene was added by vigorous stirring (mechanical stirrer) for 30 min at 0° C. The resulted mixture was stirred for 10 hours at ambient temperature. Then, the precipitate was filtered off (G3), washed with 3×50 ml of hexanes, and dried in vacuum. Yield 165 g (90%) of white solid, which was further used without an additional purification.

1H-Inden-2-ylphosphonous dichloride (2).

1 H-Inden-2-ylphosphonous dichloride (2).

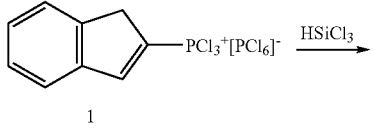

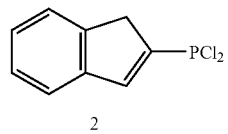

To a suspension of 4.96 g (10 mmol) of 1 in 50 ml of toluene, 2.22 ml (2.98 g, 22 mmol) of HSiCl$_3$ was added at ambient temperature. This mixture was refluxed for 6 hours to form clear yellow solution. Volatile components were distilled off at 50° C., and the yellow oil formed was dried in vacuum at this temperature. The crystalline material formed is pure 1H-Inden-2-ylphosphonous dichloride, 2. Yield 2.17 g (99%).

Anal. calc. for C$_9$H$_7$Cl$_2$P: C, 49.81; H, 3.25. Found: C, 49.67; H, 3.18.

$^1$H NMR (C$_6$D$_6$): δ 7.14–7.17 (m, 4H, 4,5,6,7-H), 6.92 (dt, J=8.1 Hz, J=1.7 Hz, 1H, 3-H), 3.61 (d, J=1.7 Hz, 2H, 1,1'-H).

$^{13}$C{$^1$H} NMR (C$_6$D$_6$): δ 147.2 (d, J=54.9 Hz), 145.9 (d, J=2.8 Hz), 144.1 (d, J=54.9 Hz), 142.2 (d, J=12.2 Hz), 127.8, 127.0, 124.3, 123.2, 37.9.

$^{31}$P{$^1$H} NMR (C$_6$D$_6$): δ 151.4.

Diethyl 1H-inden-2-ylphosphonate (9).

Diethyl 1 H-inden-2-ylphosphonate (9).

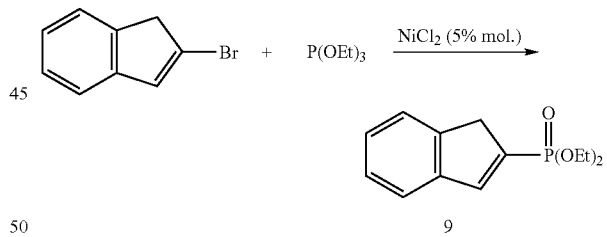

To 91.0 g (0.467 mol) of 2-bromo-1H-indene and 3.02 g (0.023 mol) of NiCl$_2$ in 250 ml flask equipped with a distillation head, 85.0 ml (82.4 g, 0.496 mol) of (EtO)$_3$P were added. This black mixture was heated in the oil bath at 185–190° C. for 3 hours. During this procedure, argon gas was bubbled through the mixture to eliminate ethyl bromide formed. The crude product was distilled in vacuum (171–175° C./1 mm). Yield 102.4 g (87%) of colorless oil of diethyl 1H-inden-2-ylphosphonate, 9.

Anal. calc. for C$_{13}$H$_{17}$O$_3$P: C, 61.90; H, 6.79. Found: C, 62.03; H, 6.82.

$^1$H NMR (CDCl$_3$): δ 7.63 (m, 1H, 3-H), 7.51 (m, 2H, 4,7-H), 7.32 (m, 2H, 5,6-H), 4.07–4.23 (m, 4H, OCH$_2$Me), 3.65 (m, 2H 1,1'-H in indenyl), 1.35 (t, J=7.0 Hz, 6H, Me).

$^{31}$P{$^1$H} NMR (CDCl$_3$): δ 31.2.

tert-Butyl(1H-inden-2-yl)phonosphinous chloride (8).

tert-Butyl(1H-inden-2-yl) phosphinous chloride (8).

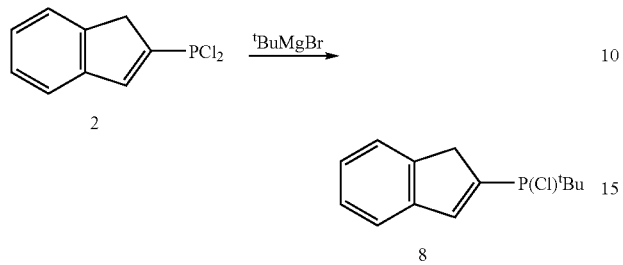

To a solution of 1.09 g (5.0 mmol) of 2 in 40 ml of diethyl ether-hexanes (1:1, vol.), 4.7 ml of 1.06 M $^t$BuMgCl in ether was added dropwise at vigorous stirring for 2 hours at −90° C. The resulted mixture was slowly warmed to ambient temperature, stirred overnight, and filtered through glass frit (G3). The precipitate was additionally washed with 3×15 ml of ether. The combined filtrate was evaporated to dryness, and the residue was dried in vacuum. Yield 1.19 g (99%) of colorless solid.

Anal. calc. for $C_{13}H_{16}ClP$: C, 65.41; H, 6.76. Found: C, 65.62; H, 7.85.

$^1$H NMR ($C_6D_6$): δ 7.15–7.34 (m, 5H, 3,4,5,6,7-H), 3.43–3.68 (m, 1,1'-H in indenyl), 1.11 (d, J=14.0 Hz, 9H, $^t$Bu).

$^{13}$C{1H} NMR ($C_6D_6$): δ 146.1, 144.5 (d, J=45.8 Hz), 144.1 (d, J=10.7 Hz), 142.9 (d, J=35.1 Hz), 126.9, 126.2, 124.0, 121.9, 42.6 (d, J=6.1 Hz), 34.8 (d, J=29.0 Hz), 25.8 (d, J=18.3 Hz).

$^{31}$P{$^1$H} NMR ($C_6D_6$): δ 104.5.

1H-Inden-2-ylphosphine (10), 1H-Indan-2-ylphosphine (11) and compound 12.

1H-Inden-2-ylphosphine (10), 1H-Indan-2-ylphosphine (11) and compound 12.

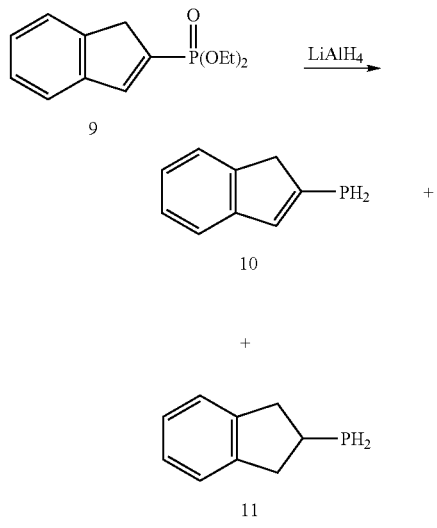

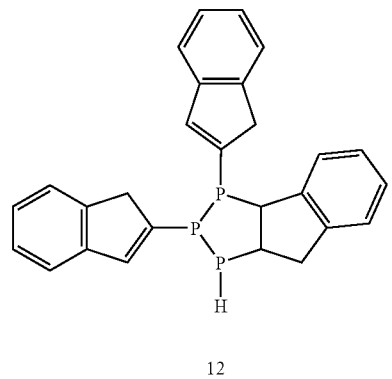

To a suspension of 13.3 g (0.350 mol) of LiAlH$_4$ in 200 ml of ether, a solution of 58.7 g (0.233 mol) of 9 in 140 ml of ether was dropwise for 2 hours. The resulting mixture was refluxed for 2 hours, then, cooled to room temperature, and 50 ml of water was added dropwise to decompose an excess of metal hydrides. The ether solution was separated, and the residue was diluted with 2×200 ml of ether. The combined extract was evaporated to ca. 100 ml. A white solid precipitated at −30° C. was separated, washed with 10 ml of cold ether and dried in vacuum. Yield: 2.39 g (7%) of compound 12. The yellow solution was evaporated, and the obtained oil was distilled in vacuum (108–110° C./8 mm). Yield: 21.90 g of ca. 4 to 1 mixture of 10 (51%) and 11 (12%). Additional careful fractional distillation of this mixture gave 14.52 g of 10 of 93% purity ($^{31}$P NMR).

Compound 10.

Anal. calc. for $C_9H_9P$: C, 72.97; H, 6.12. Found: C, 72.85; H, 6.20.

$^1$H NMR ($C_6D_6$): δ 7.15–7.27 (m, 3H, 5,6,7-H), 7.06–7.12 (m, 1H, 3-H), 6.83–6.87 (m, 1H, 4-H), 3.56 (m, $J_{P-H}$=199.6 Hz, 2H, PH$_2$), 3.05 (m, 2H, 1,1'-H).

$^{13}$C NMR ($C_6D_6$): δ 146.2, 145.3 (d, J=9.2 Hz), 142.0 (d, J=26.0 Hz), 134.8 (d, J=13.7 Hz), 126.6, 125.2, 123.5, 120.8, 46.7. $^{31}$P NMR ($C_6D_6$): δ −131.6 (dt, $J_{P-H}$=199.6 Hz, $J_{P-H}$=7.8 Hz).

Compound 11.

$^{31}$P NMR ($C_6D_6$): δ −102.6 (m, $J_{P-H}$=189.5 Hz, $J_{P-H}$=11.7 Hz, $J_{P-H}$=9.8 Hz).

Compound 12.

Anal. calc. for $C_{27}H_{23}P_3$: C, 73.64; H, 5.26. Found: C, 73.56; H, 5.20.

$^1$H NMR spectrum (in $CD_2Cl_2$), see FIG. 1.

$^{31}$P{$^1$H} NMR ($CD_2Cl_2$): δ 36.2 (d, $J_{P-P}$=270.9 Hz), −26.0 (dd, $J_{P-P}$=235.9 Hz, $J_{P-P}$=270.9 Hz), −40.3 (d, $J_{P-P}$=235.9 Hz).

$^{31}$P NMR ($CD_2Cl_2$): δ 36.2 (d, $J_{P-P}$=270.9 Hz), −26.0 (ddd, $J_{P-P}$=270.9 Hz, $J_{P-P}$=235.9 Hz, $J_{P-H}$=16.9 Hz), −40.3 (dddt, $J_{P-P}$=235.9 Hz, $J_{P-H}$=208.9 Hz, $J_{P-H}$=19.0 Hz, $J_{P-H}$=12.4 Hz).

tert-Butyl(1H-inden-2-yl)phosphine (14).

tert-Butyl (1 H-inden-2-yl) phosphine (14).

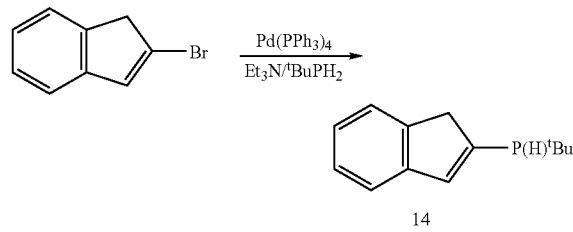

To 9.61 g (0.049 mol) of 2-bromo-1H-indene and 1.13 g (0.98 mmol) of Pd(PPh$_3$)$_4$ in 25 ml of toluene, 7.5 ml (5.45 g, 0.054 mol) of Et$_3$N and 4.88 g (0.054 mol) of $^t$BuPH$_2$ were added. This mixture was refluxed for 14 hours, cooled to room temperature, and filtered through glass frit (G3) to separate out compound 15. The filtrate was evaporated to dryness. The crude product was distilled in vacuum (108–110° C./3 mm). Yield 3.07 g (31%) of crystalline solid of 14.

Anal. calc. for C$_{13}$H$_{17}$P: C, 76.45; H, 8.39. Found: C, 76.32; H, 8.33.

$^1$H NMR (CDCl$_3$): δ 7.42 (m, 1H, 7-H), 7.36 (m, 1H, 4-H), 7.25 (m, 1H, 5-H), 7.16 (m, 1H, 6-H), 7.06 (m, 1H, 3-H), 3.86 (br.s, 1H, PH), 3.56 (m, 2H, 1,1'-H in indenyl), 1.18 (d, 9H, J=12.9 Hz, $^t$Bu).

$^{13}$C{$^1$H} NMR (CDCl$_3$): δ 145.9 (d, J=3.3 Hz), 145.1 (d, J=6.1 Hz), 141.4 (d, J=19.8 Hz), 140.7 (d, J=16.8 Hz), 126.4, 124.8, 123.3, 120.6, 45.8 (d, J=7.6 Hz), 30.2 (d, J=13.7 Hz), 29.4 (d, J=7.6 Hz).

$^{31}$P{$^1$H} NMR (CDCl$_3$): δ −28.7 (d, J=207.4 Hz).

tert-Butyl[di(1H-inden-2yl)]phosphine (15).

tert-Butyl [di(1 h-inden-2-yl)] phosphine (15).

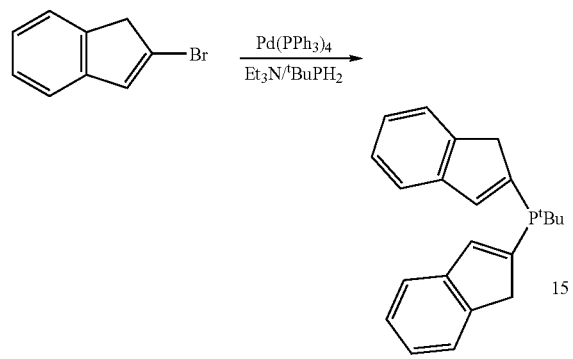

To 15.61 g (0.080 mol) of 2-bromo-1H-indene and 1.38 g (1.19 mmol) of Pd(PPh$_3$)$_4$ in 60 ml of toluene, 22.3 ml (16.19 g, 0.160 mol) of Et$_3$N and 3.60 g (0.040 mol) of $^t$BuPH$_2$ were added. This mixture was refluxed for 24 hours, cooled to room temperature, and passed through short column with Silica Gel using 200 ml of toluene as eluent. The filtrate was evaporated to dryness to give oil, which after treatment with 150 ml of hot ethanol gave a gray precipitate. This precipitate was separated (G3), washed with 3×5 ml of cold ethanol and dried in vacuum. Yield 10.83 g (85%) of 15.

Anal. calc. for C$_{22}$H$_{23}$P: C, 82.99; H, 7.28. Found: C, 82.71; H, 7.38.

$^1$H NMR (C$_6$D$_6$): δ 7.26 (m, 2H, 7-H), 7.23 (m, 2H, 5-H), 7.13–7.19 (m, 4H, 3,6-H), 7.11 (m, 2H, 4-H), 3.42 (s, 4H, 1,1'-H in indenyl), 1.14 (d, J=12.6 Hz, 9H, $^t$Bu).

$^{13}$C{$^1$H} NMR (C$_6$D$_6$): δ 148.0 (d, J=4.6 Hz), 144.9 (d, J=9.2 Hz), 144.6 (d, J=22.9 Hz), 141.8 (d, J=24.4 Hz), 126.8, 125.3, 8, 121.2, 43.9 (d, J=9.2 Hz), 31.0 (d, J=12.2 Hz), 29.0 (d, J=13.7 Hz).

$^{31}$P{$^1$H} NMR (C$_6$D$_6$): δ −6.4.

1H-Inden-2-yl(phenyl)phosphine (17).

1H-Inden-2-yl(phenyl)phosphine (17).

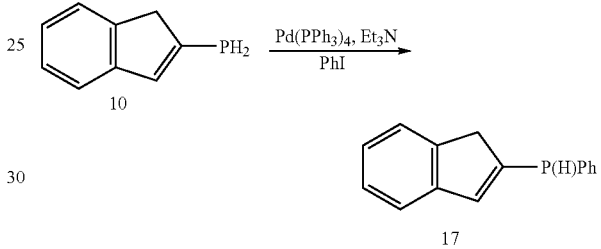

To 7.40 g (0.050 mol) of 10 and 2.88 g (2.49 mmol) of Pd(PPh$_3$)$_4$ in 20 ml of toluene, 7.7 ml (5.59 g, 0.055 mol) of Et$_3$N and, then, 5.6 ml (10.21 g, 0.050 mol) of iodobenzene were added. This mixture was refluxed for 8 hours, cooled to room temperature, and passed through short column with Silica Gel using 30 ml of toluene as eluent. The resulted solution was evaporated to dryness. The crude product was distilled in vacuum (120–121° C./2 mm). Yield 5.71 g (51%) of colorless oil of 17.

Anal. calc. for C$_{15}$H$_{13}$P: C, 80.34; H, 5.84. Found: C, 80.22; H, 5.90.

$^1$H NMR (C$_6$D$_6$): δ 7.08–7.68 (m, 10H, 3,4,5,6,7-H in indenyl and C$_6$H$_5$), 5.13 (d, J=216.3 Hz, 1H, PH), 3.24 (m, 2H, 1,1'-H in indenyl).

$^{13}$C{$^1$H} NMR (C$_6$D$_6$): δ 146.4 (d, J=3.1 Hz), 145.2 (d, J=9.2 Hz), 141.7 (d, J=15.3 Hz), 141.4 (d, J=24.4 Hz), 134.0 (d, J=16.8 Hz), 128.8 (d, J=6.1 Hz), 128.6 (d, J=6.1 Hz), 128.5, 126.7, 125.4, 123.8, 121.2, 43.7 (d, J=4.6 Hz).

$^{31}$P{$^1$H} NMR (C$_6$D$_6$): δ −43.1 (d, J=211.3 Hz).

Di(1H-inden-2yl)(phenyl)phosphine (16).

Di(1 H-inden-2-yl)(phenyl) phosphine (16).

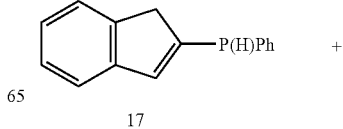

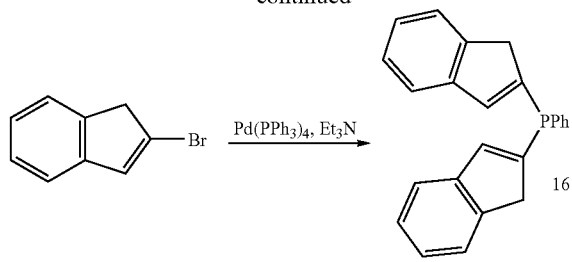

To 4.00 g (0.021 mol) of 2-bromo-1-indene and 0.46 g (0.40 mmol) of Pd(PPh$_3$)$_4$ in 20 ml of toluene, 3.2 ml (2.32 g, 0.023 mol) of Et$_3$N and, then, 4.52 g (0.020 mol) of 17 were added. This mixture was refluxed for 13 hours, cooled to room temperature, and passed through short column with Silica Gel using 150 ml of toluene as eluent. The resulted solution was evaporated to dryness. The crude product was crystallized from ethanol. Yield 1.63 g (28%) of white crystals of 16.

Anal. calc. for C$_{24}$H$_{19}$P: C, 85.19; H, 5.66. Found: C, 85.01; H, 5.58.

$^1$H NMR (CDCl$_3$): δ 7.53 (m, 4H, 2,6-H in C$_6$H$_5$), 7.38 (m, 2H, 7-H in indenyl), 7.35 (m, 6H, 3,4,5-H in C$_6$H$_5$), 7.33 (m, 2H, 4-H in indenyl), 7.16 (m, 2H, 5-H in indenyl), 7.24 (m, 2H, 6-H in indenyl), 7.01 (m, 2H, 3-H in indenyl), 3.47 (m, 4H, 1,1'-H in indenyl).

$^{13}$C{$^1$H} NMR (CDCl$_3$): δ 145.9 (d, J=3.1 Hz), 144.6 (d, J=7.6 Hz), 140.3 (d, J=18.3 Hz), 136.5 (d, J=4.6 Hz), 133.7, (d, J=19.8 Hz), 129.1, 128.9 (d, J=6.1 Hz), 126.6 (d, J=6.1 Hz), 126.5, 125.1, 123.6, 121.0, 42.1 (d, J=13.7 Hz).

$^{31}$P{$^1$H} NMR (C$_6$D$_6$): δ −29.7.

Mixture of d-/l- and meso-1,2-di-tert-butyl-1,2-di (1H-inden-2yl)diphosphanes (18).

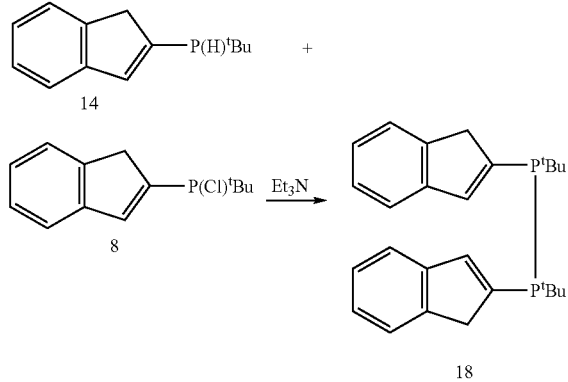

To a solution of 335 mg (1.74 mmol) of 14 in 3 ml of diethyl ether, 0.49 ml (356 mg, 3.52 mmol) of triethylamine and 415 mg (1.74 mmol) of 8 were added at −78° C. The reaction mixture was slowly warmed to ambient temperature at vigorous stirring. This mixture was additionally stirred for 5 hours at room temperature, 100 hours at 40° C., and then evaporated to dryness. The residue was dissolved in 50 ml of toluene. In the Glove Box, this solution was passed through a short column with Silica Gel 60 (d 20 mm,l 70 mm). This column was additionally washed with 250 ml of toluene. The combined extract was evaporated to dryness to give a white solid. Yield 357 mg (51%) as a mixture of d-/l-(trans-) and meso-(cis-)isomers in ratio ca. 3 to 2.

Anal. calc. for C$_{26}$H$_{32}$P$_2$: C, 76.83; H, 7.93. Found: C, 76.99; H, 8.01.

d-/l-18.

$^1$H NMR (C$_6$D$_6$): δ 7.27 (m, 2H, 3-H in indenyl), 7.19 (m, 2H, 7-H in indenyl), 7.09 (m, 2H, 5-H in indenyl), 6.89 (m, 2H, 6-H in indenyl), 6.76 (m, 2H, 4-H in indenyl), 3.12 (d, J=22.6 Hz, 2H, 1-H in indenyl), 2.65 (d, J=22.6 Hz, 2H, 1'-H in indenyl), 1.27 (t, J=6.9 Hz, 18H, $^t$Bu).

$^{13}$C NMR (C$_6$D$_6$): δ 148.8, 146.6, 144.7 (t, J=18.7 Hz), 144.3, 126.5, 125.4, 123.6, 121.2, 43.4, 29.8 (t, J=11.5 Hz), 25.7.

$^{31}$P{$^1$H} NMR (C$_6$D$_6$): δ −13.1 (max).

meso-18.

$^1$H NMR (C$_6$D$_6$): δ 7.48 (m, 2H, 3-H in indenyl), 7.24 (m, 2H, 7-H in indenyl), 7.07 (m, 2H, 5-H in indenyl), 7.04 (m, 2H, 6-H in indenyl), 7.01 (m, 2H, 4-H in indenyl), 3.80 (d, J=22.9 Hz, 2H, 1-H in indenyl), 3.55 (d, J=22.9 Hz, 2H, 1'-H in indenyl), 0.97 (t, J=6.4 Hz, 18H, $^t$Bu).

$^{13}$C{$^1$H} NMR (C$_6$D$_6$): δ 148.5, 146.7, 145.5 (t, J=18.4 Hz), 144.0, 126.8, 125.8, 124.0, 121.5, 44.3, 30.1 (t, J=9.3 Hz), 26.0.

$^{31}$P{$^1$H} NMR (C$_6$D$_6$): δ −19.5 (min).

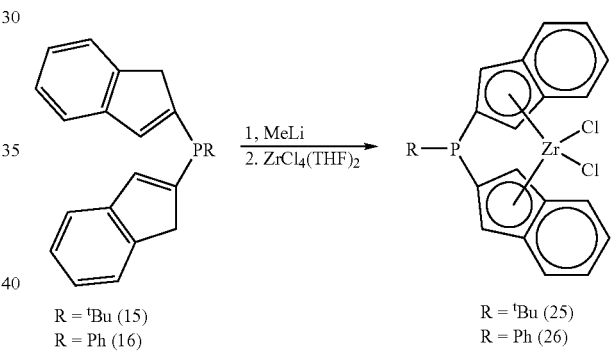

R = $^t$Bu (15)  R = $^t$Bu (25)
R = Ph (16)     R = Ph (26)

2,2'-tert-butylphosphindiyl-bis(η$^5$-indenyl)zirconium dichloride—Complex 25

To a solution of 4.66 g (14.6 mmol) of 15 in 130 ml of ether, 16.0 ml (29.2 mmol) of 1.83 M MeLi in ether were added at −90° C. This mixture was stirred for 3 hours at ambient temperature, then, 5.37 g (14.2 mmol) of ZrCl$_4$(THF)$_2$ were added at −90° C. It was stirred for 48 hours at room temperature, and, then, filtered through glass frit (G4). The precipitate was washed with 5×100 ml of hot toluene. The combined extract was evaporated to ⅔ of volume. Crystallization of the solution at −30° C. gave yellow crystals of 25. Yield 3.81 g (56%).

Anal. calc. for C$_{22}$H$_{21}$Cl$_2$PZr: C, 55.22; H, 4.42. Found: C, 55.47; H, 4.49.

$^1$H NMR (CD$_2$Cl$_2$): δ 7.57 (dq, J=8.5 Hz, J=1.0 Hz, 2H, 4/7-H in indenyl), 7.42 (dq, J=8.5 Hz, J=1.0 Hz, 2H, 7/4-H in indenyl), 7.24 (ddd, J=8.5 Hz, J=6.5 Hz, J=1.2 Hz, 2H, 5/6-H in indenyl), 7.17 (ddd, J=8.5 Hz, J=6.5 Hz, J=1.2 Hz, 2H, 5/6-H in indenyl), 6.62 (dt, J=2.6Hz, J=1.0 Hz, 2H, 1/3-H in indenyl), 6.36 (ddd, J=5.6 Hz, J=2.6 Hz, J=1.0 Hz, 2H, 3/1-H in indenyl), 1.58 (d, J=14.7 Hz, 9H, $^t$Bu).

$^{13}$C{$^1$H} NMR (CD$_2$Cl$_2$): δ 130.5 (d, J=7.9 Hz), 129.7 (d, J=17.2 Hz), 128.7, 127.7, 126.4, 126.1, 114.7 (d, J=42.7 Hz), 110.9 (d, J=33.6 Hz), 103.5 (d, J=7.6 Hz), 33.2 (d, J=15.3 Hz), 30.7 (d, J=16.8 Hz).

$^{31}$P{$^1$H} NMR (CD$_2$Cl$_2$): δ −12.0.

Figure 2:
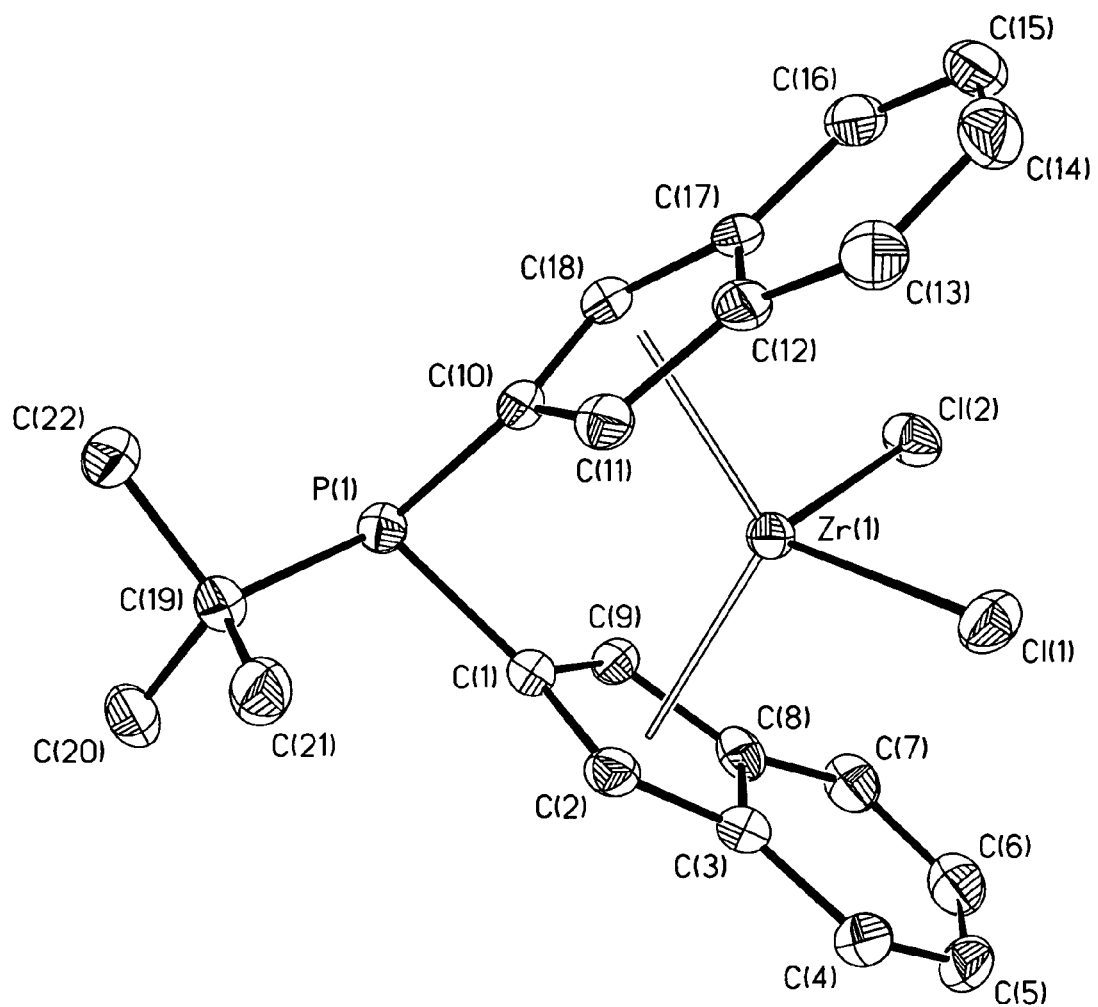
FIG. 2 is a representation of the molecular structure of compound 25.

A representation of the molecular structure of complex 25 is shown in FIG. 2.

2,2'-phenylphosphindiyl-bis(η$^5$-indenyl)zirconium dichloride—Complex 26

To a solution of 1.48 g (4.37 mmol) of 16 in 50 ml of ether, 4.8 ml (8.75 mmol) of 1.84 M MeLi in ether was added at −90° C. This mixture was stirred for 12 hours at ambient temperature, then, 1.65 g (4.37 mmol) of ZrCl$_4$(THF)$_2$ was added at −90° C. It was stirred for 24 hours at room temperature, then, evaporated to dryness. To the residue, 50 ml of toluene was added, and this mixture was stirred additionally for 12 hours. The orange slurry formed was filtered through glass frit (G4). The precipitate was washed with 50 ml of hot toluene. To the combined toluene extract, 60 ml of hexanes was added. Crystallization of this solution at −30° C. gave orange crystals of 26. Yield 0.79 g (36%).

Anal. calc. for C$_{24}$H$_{17}$Cl$_2$PZr: C, 57.83; H, 3.44. Found: C, 58.11; H, 3.56.

$^1$H NMR (C$_6$D$_6$): δ 7.53 (dq, J=8.5 Hz, J=1.0 Hz, 2H, 4/7-H in indenyl), 7.41–7.47 (m, 2H, 2,6-H in C$_6$H$_5$), 7.26 (dq, J=8.5 Hz, J=1.0 Hz, 2H, 7/4-H in indenyl), 6.98–7.20 (m, 3H, 3,4,5-H in C$_6$H$_5$), 6.96 (ddd, J=8.5 Hz, J=6.7 Hz, J=1.2 Hz, 2H, 5/6-H in indenyl), 6.87 (ddd, J=8.5 Hz, J=6.7 Hz, J=1.2 Hz, 2H, 5/6-H in indenyl), 6.21 (ddd, J=4.4 Hz, J=2.6 Hz, J=0.9 Hz, 2H, 1/3-H in indenyl), 5.97 (m, 2H, 3/1-H in indenyl).

$^{13}$C{$^1$H} NMR (C$_6$D$_6$): δ 134.5, 134.1, 134.0, 131.2 (d, J=13.7 Hz), 129.2 (d, J=4.1 Hz), 127.3, 126.8, 126.5, 125.1, 125.0, 109.7 (d, J=38.2 Hz), 107.2 (d, J=27.5 Hz), 101.4 (d, J=7.6 Hz).

$^{31}$P{$^1$H} NMR (C$_6$D$_6$): δ −30.4.

2,2'-(1,2di-tert-butyldiphosphandiyl)-bis(η$^5$-indenyl) zirconium dichloride-Complex 27.

2,2'-(1,2-di-tert-butyldiphosphandiyl)-bis (n$^5$-indenyl) zirconium dichloride-Complex 27.

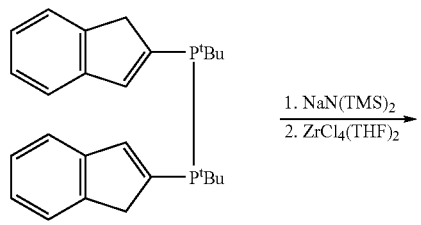

18

-continued

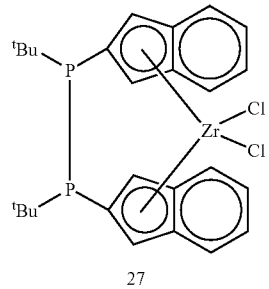

27

To a solution of 713 mg (1.75 mmol) of 18 in 15 ml of toluene, a solution of 642 mg (3.50 mmol) of NaN(TMS)$_2$ in 10 ml of toluene was added at ambient temperature. This mixture was stirred for 24 hours. The white precipitate formed was filtered off (G3), washed with 3×30 ml of hexanes, and dried in vacuum. To a suspension of this sodium salt in 25 ml of diethyl ether, 660 mg (1.75 mmol) of ZrCl$_4$(THF)$_2$ was added. The resulted mixture was stirred for 48 hours at ambient temperature and then evaporated to dryness. The crude product was extracted with 30 ml of toluene. The toluene solution was filtered through glass frit (G4), and the filtrate was evaporated to ca. 10 ml. Crystals that precipitated at −30° C. were collected, washed with 3×30 ml of hexanes, and dried in vacuum. Yield 520 mg (52%) of pure rac-complex (trans-$^t$BuPPBu$^t$).

Anal. calc. for C$_{26}$H$_{30}$Cl$_2$P$_2$Zr: C, 55.12; H, 5.34. Found: C, 55.28; H, 5.38.

$^1$H NMR (CD$_2$Cl$_2$): δ 7.52 (m, 2H, 4/7-H in indenyl), 7.42 (m, 2H, 7/4-H in indenyl), 7.20 (m, 2H, 5/6-H in indenyl), 7.12 (m, 2H, 5/6-H in indenyl), 6.85 (m, 2H, 1/3-H in indenyl), 6.62 (m, 2H, 3/1-H in indenyl), 1.19 (t, J=6.9 Hz, 18H, $^t$Bu).

$^{13}$C{$^1$H} NMR (CD$_2$Cl$_2$): δ 134.8, 130.9 (t, J=5.8 Hz), 128.3, 127.9, 127.6 (t, J=11.5 Hz), 127.0, 126.3, 116.8 (t, J=20.7 Hz), 106.5 (t, J=4.6 Hz), 32.8 (t, J=4.6 Hz), 31.1 (t, J=9.2 Hz).

$^{31}$P{$^1$H} NMR (CD$_2$Cl$_2$): δ −7.3.

Figure 3:
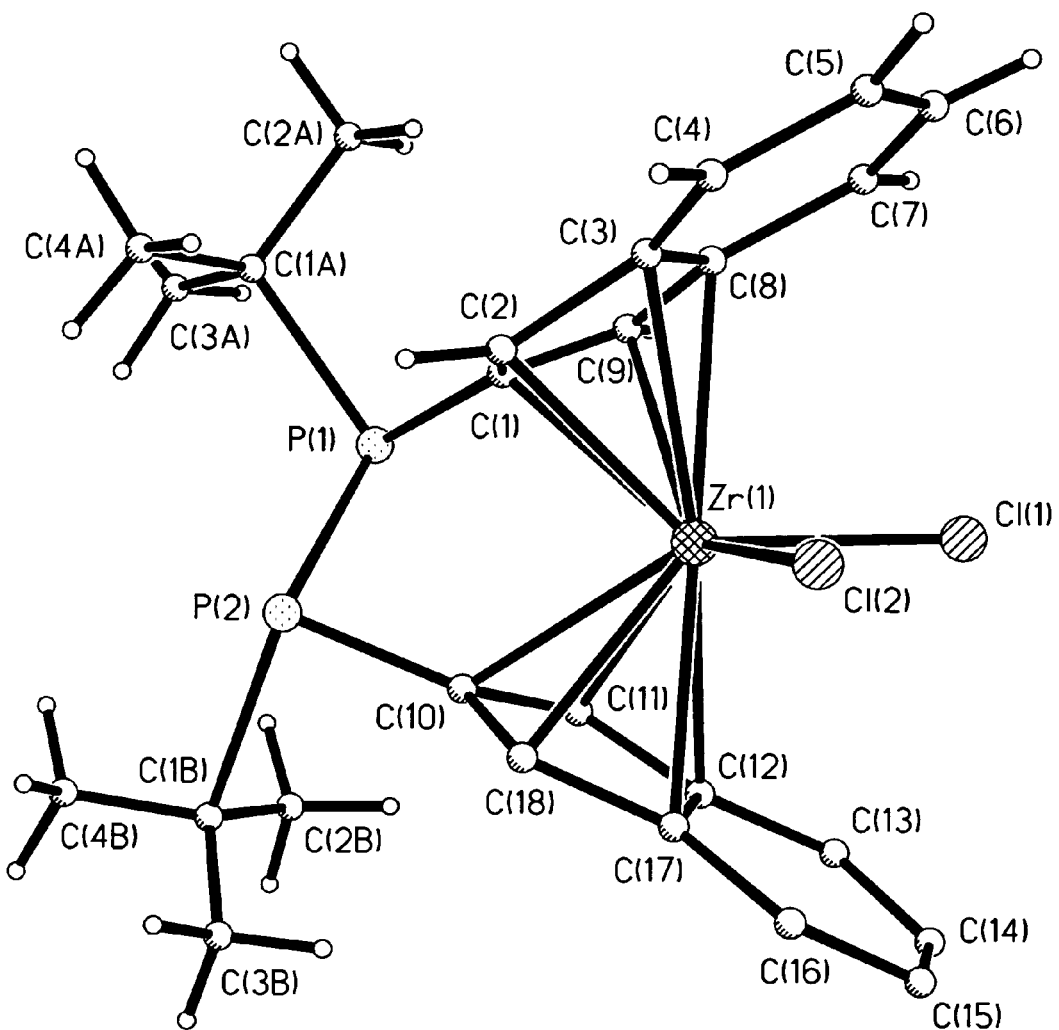
FIG. 3 is a representation of the molecular structure of compound 27.

A representation of the molecular structure of complex 27 is shown in FIG. 3.

Experimental—Polymerizations:

In the following experiments pressure is reported in atmospheres and pounds per square inch. The conversion factors to S. I. Units are; 1 psi equals 6.894757 kPa and 1 atm equals 101.325 kPa.

Transition metal compound or complex (TMC) solutions were typically prepared using toluene (ExxonMobil Chemical—anhydrous, stored under N$_2$) (98%). Unless otherwise mentioned, TMC solutions are 0.2 mmol/L for C$_2$ and C$_2$/C$_8$ (co)polymerizations.

Solvents, polymerization grade toluene and hexanes were supplied by ExxonMobil Chemical Co. and thoroughly dried and degassed prior to use.

1-octene (98%) was purchased from Aldrich Chemical Company and dried by stirring over NaK overnight followed by filtration through basic alumina (Aldrich Chemical Company, Brockman Basic 1).

Polymerization grade ethylene was used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

MAO (methylalumoxane, 10 wt % in toluene) was purchased from Albemarle Corporation and was used as a 1 wt % or 2 wt % in toluene solution.

Reactor Description and Preparation:

Polymerizations were conducted in an inert atmosphere ($N_2$) drybox using autoclaves equipped with an external heater for temperature control, glass inserts (internal volume of reactor=23.5 mL for C2 and C2/C8 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene Polymerization or Ethylene/1-octene Copolymerization:

The reactor was prepared as described above, and then purged with ethylene. Toluene, 1-octene, and MAO, were added via syringe at room temperature and atmospheric pressure. The reactor was then brought to process temperature (80° C.) and charged with ethylene to process pressure (75 psig =517.1 kPa) while stirring at 800 RPM. The TMC (0.02 μmol) was added via syringe with the reactor at process conditions. Amounts of reagents not specified above are given in Tables 2 and 4. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched after a predetermined cumulative amount of ethylene had been added or for a maximum of 20 minutes polymerization time. The final conversion (in psi) of ethylene added/consumed is reported in the Tables 2 and 4, in addition to the quench time for each run. The reactors were cooled and vented. The polymer was isolated after the solvent was removed in-vacuo. Yields reported include total weight of polymer and residual catalyst. Catalyst activity is reported as grams of polymer per mmol transition metal compound per atmosphere ethylene per hour of reaction time (g/mmol·hr·atm).

Polymer Characterization:

Polymer characterization results for polyethylene samples are reported in Table 3, and for ethylene-1-octene copolymers are reported in Table 5.

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 160° C. in a shaker oven for approximately 3 hours. The typical concentration of polymer in solution is between 0.4 to 0.9 mg/mL with a BHT concentration of 1.25 mg BHT/mL of TCB. Samples are cooled to 135° C. for testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

The sample preparation for SAMMS (Sensory Array Modular Measurement System) thermal analysis measurements involved depositing the stabilized polymer solution onto a silanized wafer (Part Number S10457, Symyx). The solvent was then evaporated off at ~145° C. By this method, approximately between 0.12 and 0.24 mg of polymer is deposited onto each corresponding wafer cell. Thermal analysis was measured on a Symyx Technologies SAMMS instrument that measures polymer melt temperatures via the 3 ω technique. The analysis first employs a rapid-scan protocol that heats each cell from 27° C. to 200° C. in ~35 seconds and then rapidly cools the sample to room temperature. This complete procedure takes approximately 60 seconds per cell and is used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. SAMMS data is reported under the heading of Tm (C) in Tables 3 and 5.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt. % copolymer is determined via measurement of the methyl deformation band at ~1375 $cm^{-1}$. The peak height of this band is normalized by the combination and overtone band at ~4321 $cm^{-1}$, which corrects for path length differences. The normalized peak height is correlated to individual calibration curves from $^1H$ NMR data to predict the wt. % copolymer content within a concentration range of ~2 to 35 wt. % for octene. Typically, $R^2$ correlations of 0.98 or greater are achieved. These numbers are reported in Table 5 under the heading, Octene wt %).

TABLE 2

Ethylene Polymerization Runs - Part 1.

| Ex# | TMC | Activator (μmol) | Total Toluene (mL) | Final Conversion (psi) | Quench Time (sec) | Polymer Yield (g) | Activity (g/mmol · hr · atm) |
|---|---|---|---|---|---|---|---|
| PE-25 | 25 | 9.98 | 3.80 | 25.5 | 52.0 | 0.087 | 59,038 |
| PE-26 | 25 | 9.98 | 3.80 | 25.2 | 43.2 | 0.082 | 66,982 |
| PE-27 | 25 | 9.98 | 3.80 | 25.5 | 48.0 | 0.081 | 59,585 |
| PE-28 | 25 | 9.98 | 3.80 | 25.6 | 48.4 | 0.094 | 68,505 |

TABLE 3

Ethylene Polymerization Runs - Part 2.

| Ex# | TMC | Mw | Mn | PDI | Tm (° C.) |
|---|---|---|---|---|---|
| PE-25 | 25 | 6,568 | 4,513 | 1.5 | none |
| PE-26 | 25 | 6,708 | 4,633 | 1.4 | none |
| PE-27 | 25 | 5,357 | 3,684 | 1.5 | none |
| PE-28 | 25 | 6,896 | 4,828 | 1.4 | 130.2 |

TABLE 4

Ethylene-1-Octene Polymerization Runs - Part 1.

| Ex# | TMC | Activator (μmol) | 1-Octene (μmol) | Total Toluene (mL) | Final Conversion (psi) | Quench Time (sec) | Polymer Yield (g) | Activity (g/mmol · hr · atm) |
|---|---|---|---|---|---|---|---|---|
| EO-26 | 25 | 9.98 | 638.1 | 3.80 | 25.0 | 41.3 | 0.091 | 77,792 |
| EO-27 | 25 | 9.98 | 638.1 | 3.80 | 25.5 | 42.9 | 0.091 | 74,749 |
| EO-28 | 25 | 9.98 | 638.1 | 3.80 | 25.0 | 66.4 | 0.103 | 54,718 |

TABLE 5

Ethylene-1-Octene Polymerization Runs - Part 2.

| Ex# | TMC | Mw | Mn | PDI | Octene (wt %) | Tm (° C.) |
|---|---|---|---|---|---|---|
| EO-26 | 25 | 6,707 | 4,614 | 1.5 | 7.5 | 102.3 |
| EO-27 | 25 | 5,358 | 3,707 | 1.4 | 4.7 | 90.8 |
| EO-28 | 25 | 6,645 | 4,572 | 1.5 | 11.7 | 123.6 |

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

The invention claimed is:

1. A metallocene compound represented by formula:

wherein
M is a group 3, 4, 5 or 6 transition metal atom, or a lanthanide metal atom, or actinide metal atom;
E is a substituted or unsubstituted indenyl ligand that is bonded to Y through the two position of the indenyl ring;
A is bonded to Y, and is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand, or A may, independently, be defined as E;
Y is a phosphorus containing group that is bonded to both E and A, and is bonded via the phosphorus atom to E; and
each X is, independently, a univalent anionic ligand, or both X are joined and bound to the metal atom to form a metallocycle ring, or both X join to form a chelating ligand, a diene ligand, or an alkylidene ligand.

2. The compound of claim 1 wherein M is Ti, Zr or Hf.

3. The compound of claim 1 wherein Y is selected from the group of diradicals consisting of PR, RP—PR, RN—PR, and RN—PR, where each R is, independently, selected from the group consisting of C1 to C30 hydrocarbyls.

4. The compound of claim 1 wherein Y is selected from the group of diradicals consisting of PR, RP—PR, and RN—PR, where each R is, independently, selected from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof.

5. The compound of claim 1 wherein each X is, independently, selected from the group consisting of chloride, bromide, fluoride, iodide, hydride, and C1 to C30 hydrocarbyls.

6. The compound of claim 1 wherein each X is, independently, selected from the group consisting of chloride, bromide, fluoride, iodide, hydride, methyl, ethyl, propyl, butyl, pentyl, hexyl, phenyl, benzyl, and all isomers thereof.

7. The compound of claim 1 wherein two X together are selected from butadiene, methylbutadiene, pentadiene, methylpentadiene, dimethylpentadiene, hexadiene, methylhexadiene, dimethylhexadiene, methylidene, ethylidene, propylidene, propandiyl, butandiyl, pentandiyl, and hexandiyl.

8. The compound of claim 1 wherein A is selected from the group consisting of indenyl, methylindenyl, dimethylindenyl, methylphenylindenyl, methyltolylindenyl, methyl (dipropylphenyl)indenyl, methyl(dimethylphenyl)indenyl methylnaphthylindenyl, tetrahydroindenyl, fluorenyl, octahydrofluorenyl, dibutylfluorenyl, cyclopentadienyl, methylcyclopentadienyl, ethylcyclopentadienyl, propylcyclopentadienyl, butylcyclopentadienyl, methylpropylcyclopentadienyl, methylbutylcyclopentadienyl, dimethylcyclopentadienyl, trimethylcyclopentadienyl, and tetramethylcyclopentadienyl.

9. A metallocene compound represented by formula:

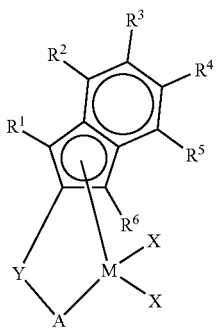

where:
M is a group 3, 4, 5 or 6 transition metal atom, or a lanthanide metal atom, or actinide metal atom;
each $R^1$, $R^2$, $R^3$, $R^4$, $R^5$, and $R^6$ is, independently, a hydrogen, a hydrocarbyl, substituted hydrocarbyl, halocarbyl, substituted halocarbyl, silylcarbyl, substituted silylcarbyl, germylcarbyl, or substituted germylcarbyl substituent, and optionally, adjacent $R^1$, $R^2$, $R^3$, $R^4$, $R^5$, and $R^6$ groups may join together to form a substituted or unsubstituted, saturated, partially unsaturated, or aromatic cyclic or polycyclic substituent;
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene ligand; and
Y is PR, RP—PR, or RN—PR, where each R is, independently, a hydrocarbyl, substituted hydrocarbyl, halocarbyl, or substituted halocarbyl substituent, and optionally, adjacent R groups may join together to form a substituted or unsubstituted, saturated or partially unsaturated cyclic or polycyclic substituent; and
X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

10. The compound of claim 9 wherein M is Ti, Zr or Hf.

11. The compound of claim 9 wherein Y is selected from the group of diradicals consisting of PR, RP—PR, and RN—PR, where each R is, independently, selected from the group consisting of C1 to C30 hydrocarbyls.

12. The compound of claim 9 wherein Y is selected from the group of diradicals consisting of PR, RP—PR, and RN—PR, where each R is, independently, selected from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof.

13. The compound of claim 9 wherein each X is, independently, selected from the group consisting of chloride, bromide, fluoride, iodide, hydride, and C1 to C30 hydrocarbyls.

14. The compound of claim 9 wherein each X is, independently, selected from the group consisting of chloride, bromide, fluoride, iodide, hydride, methyl, ethyl, propyl, butyl, pentyl, hexyl, phenyl, benzyl, and all isomers thereof.

15. The compound of claim 9 wherein two X together are selected from butadiene, methylbutadiene, pentadiene, methylpentadiene, dimethylpentadiene, hexadiene, methylhexadiene, dimethylhexadiene, methylidene, ethylidene, propylidene, propandiyl, butandiyl, pentandiyl, and hexandiyl.

16. The compound of claim 9 wherein A is selected from the group consisting of indenyl, methylindenyl, dimethylindenyl, methylphenylindenyl, methyltolylindenyl, methyl (dipropylphenyl)indenyl, methyl(dimethylphenyl)indenyl methylnaphthylindenyl, tetrahydroindenyl, fluorenyl, octahydrofluorenyl, dibutylfluorenyl, cyclopentadienyl, methylcyclopentadienyl, ethylcyclopentadienyl, propylcyclopentadienyl, butylcyclopentadienyl, methylpropylcyclopentadienyl, methylbutylcyclopentadienyl, dimethylcyclopentadienyl, trimethylcyclopentadienyl, and tetramethylcyclopentadienyl.

17. The compound of claim 9 wherein each $R^1$, $R^2$, $R^3$, $R^4$, $R^5$, and $R^6$ is, independently, selected from hydrogen or from the group consisting of C1 to C30 hydrocarbyls.

18. The compound of claim 9 wherein each $R^1$, $R^2$, $R^3$, $R^4$, $R^5$, and $R^6$ is, independently, selected from hydrogen or from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof.

19. A compound represented by the formula:

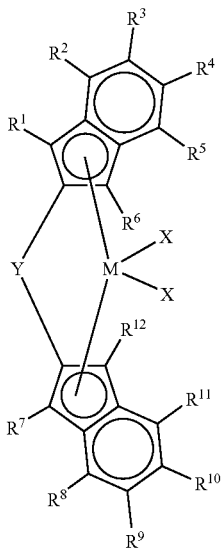

where:
- M is a group 3, 4, 5 or 6 transition metal atom, or a lanthanide metal atom, or actinide metal atom;
- each $R^1$, $R^2$, $R^3$, $R^4$, $R^5$, $R^6$, $R^7$, $R^8$, $R^9$, $R^{10}$, $R^{11}$, and $R^{12}$ is, independently, hydrogen, a hydrocarbyl, substituted hydrocarbyl, halocarbyl, substituted halocarbyl, silylcarbyl, substituted silylcarbyl, germylcarbyl, or substituted germylcarbyl substituent, and optionally, adjacent $R^1$, $R^2$, $R^3$, $R^4$, $R^5$, $R^6$, $R^7$, $R^8$, $R^9$, $R^{10}$, $R^{11}$, and $R^{12}$ substituents may join together to form a substituted or unsubstituted, saturated, partially unsaturated, or aromatic cyclic or polycyclic substituent;
- Y is PR, RP—PR, or RN—PR, where each R is, independently, a hydrocarbyl, substituted hydrocarbyl, halocarbyl, or substituted halocarbyl substituent, and optionally, adjacent R groups may join together to form a substituted or unsubstituted, saturated or partially unsaturated cyclic or polycyclic substituent; and
- X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or each X may, independently, be a halogen, alkoxide, aryloxide, amide, phosphide or other univalent anionic ligand or both X can also be joined to form a anionic chelating ligand.

20. The compound of claim 19 wherein M is Ti, Zr or Hf.

21. The compound of claim 19 wherein Y is selected from the group of diradicals consisting of PR, RP—PR, and RN—PR, where each R is, independently, selected from the group consisting of C1 to C30 hydrocarbyls.

22. The compound of claim 19 wherein Y is selected from the group of diradicals consisting of PR, RP—PR, and RN—PR, where each R is, independently, selected from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof.

23. The compound of claim 19 wherein each X is, independently, selected from the group consisting of chloride, bromide, fluoride, iodide, hydride, and C1 to C30 hydrocarbyls.

24. The compound of claim 19 wherein each X is, independently, selected from the group consisting of chloride, bromide, fluoride, iodide, hydride, methyl, ethyl, propyl, butyl, pentyl, hexyl, phenyl, benzyl, and all isomers thereof.

25. The compound of claim 19 wherein two X together are selected from butadiene, methylbutadiene, pentadiene, methylpentadiene, dimethylpentadiene, hexadiene, methylhexadiene, dimethylhexadiene, methylidene, ethylidene, propylidene, propandiyl, butandiyl, pentandiyl, and hexandiyl.

26. The compound of claim 19 wherein A is selected from the group consisting of indenyl, methylindenyl, dimethylindenyl, methylphenylindenyl, methyltolylindenyl, methyl(dipropylphenyl)indenyl, methyl(dimethylphenyl)indenyl methylnaphthylindenyl, tetrahydroindenyl, fluorenyl, octahydrofluorenyl, dibutylfluorenyl, cyclopentadienyl, methylcyclopentadienyl, ethylcyclopentadienyl, propylcyclopentadienyl, butylcyclopentadienyl, methylpropylcyclopentadienyl, methylbutylcyclopentadienyl, dimethylcyclopentadienyl, trimethylcyclopentadienyl, and tetramethylcyclopentadienyl.

27. The compound of claim 19 wherein each $R^1$, $R^2$, $R^3$, $R^4$, $R^5$, $R^6$, $R^7$, $R^8$, $R^9$, $R^{10}$, $R^{11}$, and $R^{12}$ is, independently, selected from hydrogen or from the group consisting of C1 to C30 hydrocarbyls.

28. The compound of claim 19 wherein each $R^1$, $R^2$, $R^3$, $R^5$, $R^6$, $R^7$, $R^8$, $R^9$, $R^{10}$, $R^{11}$, and $R^{12}$ is, independently, selected from hydrogen or from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof.

29. The compound claim 9 wherein:
1) each $R^1$, $R^2$, $R^3$, $R^4$, $R^5$, and $R^6$ is, independently, selected from hydrogen or from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof;
2) Y is selected from the group of diradicals consisting of PR, RP—PR, RN—PR, where each R is, independently, selected from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof;
3) X is, independently, selected from the group consisting of chloride, bromide, fluoride, iodide, hydride, methyl, ethyl, propyl, butyl, pentyl, hexyl, phenyl, benzyl, and all isomers thereof;
4) M is Ti, Zr, or Hf; and
5) A is selected from the group consisting of indenyl, methylindenyl, dimethylindenyl, methylphenylindenyl, methyltolylindenyl, methyl(dipropylphenyl)indenyl, methyl(dimethylphenyl)indenyl methylnaphthylindenyl, tetrahydroindenyl, fluorenyl, octahydrofluorenyl, dibutylfluorenyl, cyclopentadienyl, methylcyclopentadienyl, ethylcyclopentadienyl, propylcyclopentadienyl, butylcyclopentadienyl, methylpropylcyclopentadienyl, methylbutylcyclopentadienyl, dimethylcyclopentadienyl, trimethylcyclopentadienyl, and tetramethylcyclopentadienyl.

30. The compound claim 19 wherein:
1) each $R^1$, $R^2$, $R^3$, $R^4$, $R^5$, $R^6$, $R^7$, $R^8$, $R^9$, $R^{10}$, $R^{11}$, and $R^{12}$ is, independently, selected from hydrogen or from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof;
2) Y is selected from the group of diradicals consisting of PR, RP—PR, and RN—PR, where each R is, independently, selected from the group consisting of methyl, ethyl, propyl, butyl, pentyl, hexyl, heptyl, octyl, nonyl, decyl, undecyl, dodecyl, phenyl, cyclohexyl, tolyl, mesityl, naphthyl, and all isomers thereof;
3) X is, independently, selected from the group consisting of chloride, bromide, fluoride, iodide, hydride, methyl, ethyl, propyl, butyl, pentyl, hexyl, phenyl, benzyl, and all isomers thereof; and
4) M is Ti, Zr, or Hf.

31. A compound selected from the group consisting of:
2,2'-phenylphosphindiyl-bis(indenyl)zirconium dichloride,
2,2'-methylphosphindiyl-bis(indenyl)zirconium dichloride,
2,2'-ethylphosphindiyl-bis(indenyl)zirconium dichloride,
2,2'-propylphosphindiyl-bis(indenyl)zirconium dichloride,
2,2'-butylphosphindiyl-bis(indenyl)zirconium dichloride,
2,2'-(1,2-dimethyldiphosphandiyl)-bis(indenyl)zirconium dichloride,
2,1'-phenylphosphindiyl(indenyl)(cyclopentadienyl)zirconium dichloride,
2,1'-methylphosphindiyl(indenyl)(cyclopentadienyl)zirconium dichloride,
2,1'-ethylphosphindiyl(indenyl)(cyclopentadienyl)zirconium dichloride,
2,1'-propylphosphindiyl(indenyl)(cyclopentadienyl)zirconium dichloride,
2,1'-butylphosphindiyl(indenyl)(cyclopentadienyl)zirconium dichloride,
2,1'-1,2-dimethyldiphosphandiyl)(indenyl)(cyclopentadienyl)zirconium dichloride,
2,2'-phenylphosphindiyl(indenyl)(tetrahydroindenyl)zirconium dichloride,
2,2'-methylphosphindiyl(indenyl)(tetrahydroindenyl)zirconium dichloride,
2,2'-ethylphosphindiyl(indenyl)(tetrahydroindenyl)zirconium dichloride,
2,2'-propylphosphindiyl(indenyl)(tetrahydroindenyl)zirconium dichloride,
2,2'-butylphosphindiyl(indenyl)(tetrahydroindenyl)zirconium dichloride,
2,2'-(1,2-dimethyldiphosphandiyl)(indenyl)(tetrahydroindenyl)zirconium dichloride,
2,2'-phenylphosphindiyl-bis(4-phenylindenyl)zirconium dichloride,
2,2'-methylphosphindiyl-bis(4-phenylindenyl)zirconium dichloride,
2,2'-ethylphosphindiyl-bis(4-phenylindenyl)zirconium dichloride,
2,2'-propylphosphindiyl-bis(4-phenylindenyl)zirconium dichloride,
2,2'-butylphosphindiyl-bis(4-phenylindenyl)zirconium dichloride,
2,2'-(1,2-dimethyldiphosphandiyl)-bis(4-phenylindenyl)zirconium dichloride,
2,2'-phenylphosphindiyl-bis(4,7-dimethylindenyl)zirconium dichloride,
2,2'-methylphosphindiyl-bis(4,7-dimethylindenyl)zirconium dichloride,
2,2'-ethylphosphindiyl-bis(4,7-dimethylindenyl)zirconium dichloride,
2,2'-propylphosphindiyl-bis(4,7-dimethylindenyl)zirconium dichloride,
2,2'-butylphosphindiyl-bis(4,7-dimethylindenyl)zirconium dichloride,
2,2'-(1,2-dimethyldiphosphandiyl)-bis(4,7-dimethylindenyl)zirconium dichloride,
2,1'-phenylphosphindiyl(indenyl)(3-methylcyclopentadienyl)zirconium dichloride,
2,1'-methylphosphindiyl(indenyl)(3-methylcyclopentadienyl)zirconium dichloride,
2,1'-ethylphosphindiyl(indenyl)(3-methylcyclopentadienyl)zirconium dichloride,
2,1'-propylphosphindiyl(indenyl)(3-methylcyclopentadienyl)zirconium dichloride,
2,1'-butylphosphindiyl(indenyl)(3-methylcyclopentadienyl)zirconium dichloride,
2,1'-(1,2-dimethyldiphosphandiyl)(indenyl)(3-methylcyclopentadienyl)zirconium dichloride,
2,1'-phenylphosphindiyl(indenyl)(2,4-dimethylcyclopentadienyl)zirconium dichloride,
2,1'-methylphosphindiyl(indenyl)(2,4-dimethylcyclopentadienyl)zirconium dichloride,
2,1'-ethylphosphindiyl(indenyl)(2,4-dimethylcyclopentadienyl)zirconium dichloride,
2,1'-propylphosphindiyl(indenyl)(2,4-dimethylcyclopentadienyl)zirconium dichloride,
2,1'-butylphosphindiyl(indenyl)(2,4-dimethylcyclopentadienyl)zirconium dichloride,
2,1'-(1,2-dimethyldiphosphandiyl)(indenyl)(2,4-dimethylcyclopentadienyl)zirconium dichloride,
2,1'-phenylphosphindiyl(indenyl)(2-methyl-4-butylcyclopentadienyl)zirconium dichloride,
2,1'-methylphosphindiyl(indenyl)(2-methyl-4-butylcyclopentadienyl)zirconium dichloride,
2,1'-ethylphosphindiyl(indenyl)(2-methyl-4-butylcyclopentadienyl)zirconium dichloride,
2,1'-propylphosphindiyl(indenyl)(2-methyl-4-butylcyclopentadienyl)zirconium dichloride,
2,1'-butylphosphindiyl(indenyl)(2-methyl-4-butylcyclopentadienyl)zirconium dichloride,
2,1'-(1,2-dimethyldiphosphandiyl)(indenyl)(2-methyl-4-butylcyclopentadienyl)zirconium dichloride,
2,9'-phenylphosphindiyl(indenyl)(fluorenyl)zirconium dichloride,
2,9'-methylphosphindiyl(indenyl)(fluorenyl)zirconium dichloride,
2,9'-ethylphosphindiyl(indenyl)(fluorenyl)zirconium dichloride,
2,9'-propylphosphindiyl(indenyl)(fluorenyl)zirconium dichloride,
2,9'-butylphosphindiyl(indenyl)(fluorenyl)zirconium dichloride,
2,9'-(1,2-dimethyldiphosphandiyl)(indenyl)(fluorenyl) zirconium dichloride,
2,2'-phenylphosphindiyl-bis(indenyl)zirconium dimethyl,
2,2'-methylphosphindiyl-bis(indenyl)zirconium dimethyl,
2,2'-ethylphosphindiyl-bis(indenyl)zirconium dimethyl,
2,2'-propylphosphindiyl-bis(indenyl)zirconium dimethyl,
2,2'-butylphosphindiyl-bis(indenyl)zirconium dimethyl,
2,2'-(1,2-dimethyldiphosphandiyl)-bis(indenyl)zirconium dimethyl,
2,1'-phenylphosphindiyl(indenyl)(cyclopentadienyl)zirconium dimethyl,
2,1'-methylphosphindiyl(indenyl)(cyclopentadienyl)zirconium dimethyl, 2,1'-ethylphosphindiyl(indenyl)(cyclopentadienyl)zirconium dimethyl,
2,1'-propylphosphindiyl(indenyl)(cyclopentadienyl)zirconium dimethyl,
2,1'-butylphosphindiyl(indenyl)(cyclopentadienyl)zirconium dimethyl,
2,1'-1,2-dimethyldiphosphandiyl)(indenyl)(cyclopentadienyl)zirconium dimethyl,
2,2'-phenylphosphindiyl(indenyl)(tetrahydroindenyl)zirconium dimethyl,
2,2'-methylphosphindiyl(indenyl)(tetrahydroindenyl)zirconium dimethyl,
2,2'-ethylphosphindiyl(indenyl)(tetrahydroindenyl)zirconium dimethyl,
2,2'-propylphosphindiyl(indenyl)(tetrahydroindenyl)zirconium dimethyl,
2,2'-butylphosphindiyl(indenyl)(tetrahydroindenyl)zirconium dimethyl,
2,2'-(1,2-dimethyldiphosphandiyl)(indenyl)(tetrahydroindenyl)zirconium dimethyl,
2,2'-phenylphosphindiyl-bis(4-phenylindenyl)zirconium dimethyl,
2,2'-methylphosphindiyl-bis(4-phenylindenyl)zirconium dimethyl,
2,2'-ethylphosphindiyl-bis(4-phenylindenyl)zirconium dimethyl,
2,2'-propylphosphindiyl-bis(4-phenylindenyl)zirconium dimethyl,
2,2'-butylphosphindiyl-bis(4-phenylindenyl)zirconium dimethyl,
2,2'-(1,2-dimethyldiphosphandiyl)-bis(4-phenylindenyl)zirconium dimethyl,
2,2'-phenylphosphindiyl-bis(4,7-dimethylindenyl)zirconium dimethyl,
2,2'-methylphosphindiyl-bis(4,7-dimethylindenyl)zirconium dimethyl,
2,2'-ethylphosphindiyl-bis(4,7-dimethylindenyl)zirconium dimethyl,
2,2'-propylphosphindiyl-bis(4,7-dimethylindenyl)zirconium dimethyl,
2,2'-butylphosphindiyl-bis(4,7-dimethylindenyl)zirconium dimethyl,
2,2'-(1,2-dimethyldiphosphandiyl)-bis(4,7-dimethylindenyl)zirconium dimethyl,
2,1'-phenylphosphindiyl(indenyl)(3-methylcyclopentadienyl)zirconium dimethyl,
2,1'-methylphosphindiyl(indenyl)(3-methylcyclopentadienyl)zirconium dimethyl,
2,1'-ethylphosphindiyl(indenyl)(3-methylcyclopentadienyl)zirconium dimethyl,
2,1'-propylphosphindiyl(indenyl)(3-methylcyclopentadienyl)zirconium dimethyl,
2,1'-butylphosphindiyl(indenyl)(3-methylcyclopentadienyl)zirconium dimethyl,
2,1'-(1,2-dimethyldiphosphandiyl)(indenyl)(3-methylcyclopentadienyl)zirconium dimethyl,
2,1'-phenylphosphindiyl(indenyl)(2,4-dimethylcyclopentadienyl)zirconium dimethyl,
2,1'-methylphosphindiyl(indenyl)(2,4-dimethylcyclopentadienyl)zirconium dimethyl,
2,1'-ethylphosphindiyl(indenyl)(2,4-dimethylcyclopentadienyl)zirconium dimethyl,
2,1'-propylphosphindiyl(indenyl)(2,4-dimethylcyclopentadienyl)zirconium dimethyl,
2,1'-butylphosphindiyl(indenyl)(2,4-dimethylcyclopentadienyl)zirconium dimethyl,
2,1'-(1,2-dimethyldiphosphandiyl)(indenyl)(2,4-dimethylcyclopentadienyl)zirconium dimethyl,
2,1'-phenylphosphindiyl(indenyl)(2-methyl-4-butylcyclopentadienyl)zirconium dimethyl,
2,1'-methylphosphindiyl(indenyl)(2-methyl-4-butylcyclopentadienyl)zirconium dimethyl,
2,1'-ethylphosphindiyl(indenyl)(2-methyl-4-butylcyclopentadienyl)zirconium dimethyl,
2,1'-propylphosphindiyl(indenyl)(2-methyl-4-butylcyclopentadienyl)zirconium dimethyl,
2,1'-butylphosphindiyl(indenyl)(2-methyl-4-butylcyclopentadienyl)zirconium dimethyl,
2,1'-(1,2-dimethyldiphosphandiyl)(indenyl)(2-methyl-4-butylcyclopentadienyl)zirconium dimethyl,
2,9'-phenylphosphindiyl(indenyl)(fluorenyl)zirconium dimethyl,
2,9'-methylphosphindiyl(indenyl)(fluorenyl)zirconium dimethyl,
2,9'-ethylphosphindiyl(indenyl)(fluorenyl)zirconium dimethyl,
2,9'-propylphosphindiyl(indenyl)(fluorenyl)zirconium dimethyl,
2,9'-butylphosphindiyl(indenyl)(fluorenyl)zirconium dimethyl,
2,9'-(1,2-dimethyldiphosphandiyl)(indenyl)(fluorenyl)zirconium dimethyl,
2,2'-phenylphosphindiyl-bis(indenyl)zirconium dibenzyl,
2,2'-methylphosphindiyl-bis(indenyl)zirconium dibenzyl,
2,2'-ethylphosphindiyl-bis(indenyl)zirconium dibenzyl,
2,2'-propylphosphindiyl-bis(indenyl)zirconium dibenzyl,
2,2'-butylphosphindiyl-bis(indenyl)zirconium dibenzyl,
2,2'-(1,2-dimethyldiphosphandiyl)-bis(indenyl)zirconium dibenzyl,
2,1'-phenylphosphindiyl(indenyl)(cyclopentadienyl)zirconium dibenzyl,
2,1'-methylphosphindiyl(indenyl)(cyclopentadienyl)zirconium dibenzyl,
2,1'-ethylphosphindiyl(indenyl)(cyclopentadienyl)zirconium dibenzyl,
2,1'-propylphosphindiyl(indenyl)(cyclopentadienyl)zirconium dibenzyl,
2,1'-butylphosphindiyl(indenyl)(cyclopentadienyl)zirconium dibenzyl,
2,1'-1,2-dimethyldiphosphandiyl)(indenyl)(cyclopentadienyl)zirconium dibenzyl,
2,2'-phenylphosphindiyl(indenyl)(tetrahydroindenyl)zirconium dibenzyl,
2,2'-methylphosphindiyl(indenyl)(tetrahydroindenyl)zirconium dibenzyl,
2,2'-ethylphosphindiyl(indenyl)(tetrahydroindenyl)zirconium dibenzyl,
2,2'-propylphosphindiyl(indenyl)(tetrahydroindenyl)zirconium dibenzyl,
2,2'-butylphosphindiyl(indenyl)(tetrahydroindenyl)zirconium dibenzyl,
2,2'-(1,2-dimethyldiphosphandiyl)(indenyl)(tetrahydroindenyl)zirconium dibenzyl,
2,2'-phenylphosphindiyl-bis(4-phenylindenyl)zirconium dibenzyl,
2,2'-methylphosphindiyl-bis(4-phenylindenyl)zirconium dibenzyl,
2,2'-ethylphosphindiyl-bis(4-phenylindenyl)zirconium dibenzyl,
2,2'-propylphosphindiyl-bis(4-phenylindenyl)zirconium dibenzyl,
2,2'-butylphosphindiyl-bis(4-phenylindenyl)zirconium dibenzyl, 2,2'-(1,2-dimethyldiphosphandiyl)-bis(4-phenylindenyl)zirconium dibenzyl,
2,2'-phenylphosphindiyl-bis(4,7-dimethylindenyl)zirconium dibenzyl,
2,2'-methylphosphindiyl-bis(4,7-dimethylindenyl)zirconium dibenzyl,
2,2'-ethylphosphindiyl-bis(4,7-dimethylindenyl)zirconium dibenzyl,
2,2'-propylphosphindiyl-bis(4,7-dimethylindenyl)zirconium dibenzyl,
2,2'-butylphosphindiyl-bis(4,7-dimethylindenyl)zirconium dibenzyl,
2,2'-(1,2-dimethyldiphosphandiyl)-bis(4,7-dimethylindenyl)zirconium dibenzyl,
2,1'-phenylphosphindiyl(indenyl)(3-methylcyclopentadienyl)zirconium dibenzyl,
2,1'-methylphosphindiyl(indenyl)(3-methylcyclopentadienyl)zirconium dibenzyl,
2,1'-ethylphosphindiyl(indenyl)(3-methylcyclopentadienyl)zirconium dibenzyl,
2,1'-propylphosphindiyl(indenyl)(3-methylcyclopentadienyl)zirconium dibenzyl,
2,1'-butylphosphindiyl(indenyl)(3-methylcyclopentadienyl)zirconium dibenzyl,
2,1'-(1,2-dimethyldiphosphandiyl)(indenyl)(3-methylcyclopentadienyl)zirconium dibenzyl,
2,1'-phenylphosphindiyl(indenyl)(2,4-dimethylcyclopentadienyl)zirconium dibenzyl,
2,1'-methylphosphindiyl(indenyl)(2,4-dimethylcyclopentadienyl)zirconium dibenzyl,
2,1'-ethylphosphindiyl(indenyl)(2,4-dimethylcyclopentadienyl)zirconium dibenzyl,
2,1'-propylphosphindiyl(indenyl)(2,4-dimethylcyclopentadienyl)zirconium dibenzyl,
2,1'-butylphosphindiyl(indenyl)(2,4-dimethylcyclopentadienyl)zirconium dibenzyl,
2,1'-(1,2-dimethyldiphosphandiyl)(indenyl)(2,4-dimethylcyclopentadienyl)zirconium dibenzyl,
2,1'-phenylphosphindiyl(indenyl)(2-methyl-4-butylcyclopentadienyl)zirconium dibenzyl,
2,1'-methylphosphindiyl(indenyl)(2-methyl-4-butylcyclopentadienyl)zirconium dibenzyl,
2,1'-ethylphosphindiyl(indenyl)(2-methyl-4-butylcyclopentadienyl)zirconium dibenzyl,
2,1'-propylphosphindiyl(indenyl)(2-methyl-4-butylcyclopentadienyl)zirconium dibenzyl,
2,1'-butylphosphindiyl(indenyl)(2-methyl-4-butylcyclopentadienyl)zirconium dibenzyl,
2,1'-(1,2-dimethyldiphosphandiyl)(indenyl)(2-methyl-4-butylcyclopentadienyl)zirconium dibenzyl,
2,9'-phenylphosphindiyl(indenyl)(fluorenyl)zirconium dibenzyl,
2,9'-methylphosphindiyl(indenyl)(fluorenyl)zirconium dibenzyl,
2,9'-ethylphosphindiyl(indenyl)(fluorenyl)zirconium dibenzyl,
2,9'-propylphosphindiyl(indenyl)(fluorenyl)zirconium dibenzyl,
2,9'-butylphosphindiyl(indenyl)(fluorenyl)zirconium dibenzyl,
2,9'-(1,2-dimethyldiphosphandiyl)(indenyl)(fluorenyl)zirconium dibenzyl,
2,2'-phenylphosphindiyl-bis(indenyl)zirconium difluoride,
2,2'-methylphosphindiyl-bis(indenyl)zirconium difluoride,
2,2'-ethylphosphindiyl-bis(indenyl)zirconium difluoride,
2,2'-propylphosphindiyl-bis(indenyl)zirconium difluoride,
2,2'-butylphosphindiyl-bis(indenyl)zirconium difluoride,
2,2'-(1,2-dimethyldiphosphandiyl)-bis(indenyl)zirconium difluoride,
2,1'-phenylphosphindiyl(indenyl)(cyclopentadienyl)zirconium difluoride,
2,1'-methylphosphindiyl(indenyl)(cyclopentadienyl)zirconium difluoride,
2,1'-ethylphosphindiyl(indenyl)(cyclopentadienyl)zirconium difluoride,
2,1'-propylphosphindiyl(indenyl)(cyclopentadienyl)zirconium difluoride,
2,1'-butylphosphindiyl(indenyl)(cyclopentadienyl)zirconium difluoride,
2,1'-1,2-dimethyldiphosphandiyl)(indenyl)(cyclopentadienyl)zirconium difluoride,
2,2'-phenylphosphindiyl(indenyl)(tetrahydroindenyl)zirconium difluoride,
2,2'-methylphosphindiyl(indenyl)(tetrahydroindenyl)zirconium difluoride,
2,2'-ethylphosphindiyl(indenyl)(tetrahydroindenyl)zirconium difluoride,
2,2'-propylphosphindiyl(indenyl)(tetrahydroindenyl)zirconium difluoride,
2,2'-butylphosphindiyl(indenyl)(tetrahydroindenyl)zirconium difluoride,
2,2'-(1,2-dimethyldiphosphandiyl)(indenyl)(tetrahydroindenyl)zirconium difluoride,
2,2'-phenylphosphindiyl-bis(4-phenylindenyl)zirconium difluoride,
2,2'-methylphosphindiyl-bis(4-phenylindenyl)zirconium difluoride,
2,2'-ethylphosphindiyl-bis(4-phenylindenyl)zirconium difluoride,
2,2'-propylphosphindiyl-bis(4-phenylindenyl)zirconium difluoride,
2,2'-butylphosphindiyl-bis(4-phenylindenyl)zirconium difluoride,
2,2'-(1,2-dimethyldiphosphandiyl)-bis(4-phenylindenyl)zirconium difluoride,
2,2'-phenylphosphindiyl-bis(4,7-dimethylindenyl)zirconium difluoride,
2,2'-methylphosphindiyl-bis(4,7-dimethylindenyl)zirconium difluoride,
2,2'-ethylphosphindiyl-bis(4,7-dimethylindenyl)zirconium difluoride,
2,2'-propylphosphindiyl-bis(4,7-dimethylindenyl)zirconium difluoride,
2,2'-butylphosphindiyl-bis(4,7-dimethylindenyl)zirconium difluoride,
2,2'-(1,2-dimethyldiphosphandiyl)-bis(4,7-dimethylindenyl)zirconium difluoride,
2,1'-phenylphosphindiyl(indenyl)(3-methylcyclopentadienyl)zirconium difluoride,
2,1'-methylphosphindiyl(indenyl)(3-methylcyclopentadienyl)zirconium difluoride,
2,1'-ethylphosphindiyl(indenyl)(3-methylcyclopentadienyl)zirconium difluoride,
2,1'-propylphosphindiyl(indenyl)(3-methylcyclopentadienyl)zirconium difluoride,
2,1'-butylphosphindiyl(indenyl)(3-methylcyclopentadienyl)zirconium difluoride,
2,1'-(1,2-dimethyldiphosphandiyl)(indenyl)(3-methylcyclopentadienyl)zirconium difluoride, 2,1'-phenylphosphindiyl(indenyl)(2,4-dimethylcyclopentadienyl)zirconium difluoride,
2,1'-methylphosphindiyl(indenyl)(2,4-dimethylcyclopentadienyl)zirconium difluoride,
2,1'-ethylphosphindiyl(indenyl)(2,4-dimethylcyclopentadienyl)zirconium difluoride,
2,1'-propylphosphindiyl(indenyl)(2,4-dimethylcyclopentadienyl)zirconium difluoride,
2,1'-butylphosphindiyl(indenyl)(2,4-dimethylcyclopentadienyl)zirconium difluoride,
2,1'-(1,2-dimethyldiphosphandiyl)(indenyl)(2,4-dimethylcyclopentadienyl)zirconium difluoride,
2,1'-phenylphosphindiyl(indenyl)(2-methyl-4-butylcyclopentadienyl)zirconium difluoride,
2,1'-methylphosphindiyl(indenyl)(2-methyl-4-butylcyclopentadienyl)zirconium difluoride,
2,1'-ethylphosphindiyl(indenyl)(2-methyl-4-butylcyclopentadienyl)zirconium difluoride,
2,1'-propylphosphindiyl(indenyl)(2-methyl-4-butylcyclopentadienyl)zirconium difluoride,
2,1'-butylphosphindiyl(indenyl)(2-methyl-4-butylcyclopentadienyl)zirconium difluoride,
2,1'-(1,2-dimethyldiphosphandiyl)(indenyl)(2-methyl-4-butylcyclopentadienyl)zirconium difluoride,
2,9'-phenylphosphindiyl(indenyl)(fluorenyl)zirconium difluoride,
2,9'-methylphosphindiyl(indenyl)(fluorenyl)zirconium difluoride,
2,9'-ethylphosphindiyl(indenyl)(fluorenyl)zirconium difluoride,
2,9'-propylphosphindiyl(indenyl)(fluorenyl)zirconium difluoride,
2,9'-butylphosphindiyl(indenyl)(fluorenyl)zirconium difluoride,
2,9'-(1,2-dimethyldiphosphandiyl)(indenyl)(fluorenyl)zirconium difluoride,
2,1'-phenylphosphindiyl-bis(indenyl)zirconium dichloride,
2,1'-methylphosphindiyl-bis(indenyl)zirconium dichloride,
2,1'-ethylphosphindiyl-bis(indenyl)zirconium dichloride,
2,1'-propylphosphindiyl-bis(indenyl)zirconium dichloride,
2,1'-butylphosphindiyl-bis(indenyl)zirconium dichloride,
2,1'-(1,2-dimethyldiphosphandiyl)-bis(indenyl)zirconium dichloride,
2,2'-phenylphosphindiyl-bis(indenyl)hafnium dichloride,
2,2'-methylphosphindiyl-bis(indenyl)hafnium dichloride,
2,2'-ethylphosphindiyl-bis(indenyl)hafnium dichloride,
2,2'-propylphosphindiyl-bis(indenyl)hafnium dichloride,
2,2'-butylphosphindiyl-bis(indenyl)hafnium dichloride,
2,2'-(1,2-dimethyldiphosphandiyl)-bis(indenyl)hafnium dichloride,
2,1'-phenylphosphindiyl(indenyl)(cyclopentadienyl)hafnium dichloride,
2,1'-methylphosphindiyl(indenyl)(cyclopentadienyl)hafnium dichloride,
2,1'-ethylphosphindiyl(indenyl)(cyclopentadienyl)hafnium dichloride,
2,1'-propylphosphindiyl(indenyl)(cyclopentadienyl)hafnium dichloride,
2,1'-butylphosphindiyl(indenyl)(cyclopentadienyl)hafnium dichloride,
2,1'-1,2-dimethyldiphosphandiyl)(indenyl)(cyclopentadienyl)hafnium dichloride,
2,2'-phenylphosphindiyl(indenyl)(tetrahydroindenyl)hafnium dichloride,
2,2'-methylphosphindiyl(indenyl)(tetrahydroindenyl)hafnium dichloride,
2,2'-ethylphosphindiyl(indenyl)(tetrahydroindenyl)hafnium dichloride,
2,2'-propylphosphindiyl(indenyl)(tetrahydroindenyl)hafnium dichloride,
2,2'-butylphosphindiyl(indenyl)(tetrahydroindenyl)hafnium dichloride,
2,2'-(1,2-dimethyldiphosphandiyl)(indenyl)(tetrahydroindenyl)hafnium dichloride,
2,2'-phenylphosphindiyl-bis(4-phenylindenyl)hafnium dichloride,
2,2'-methylphosphindiyl-bis(4-phenylindenyl)hafnium dichloride,
2,2'-ethylphosphindiyl-bis(4-phenylindenyl)hafnium dichloride,
2,2'-propylphosphindiyl-bis(4-phenylindenyl)hafnium dichloride,
2,2'-butylphosphindiyl-bis(4-phenylindenyl)hafnium dichloride,
2,2'-(1,2-dimethyldiphosphandiyl)-bis(4-phenylindenyl)hafnium dichloride,
2,2'-phenylphosphindiyl-bis(4,7-dimethylindenyl)hafnium dichloride,
2,2'-methylphosphindiyl-bis(4,7-dimethylindenyl)hafnium dichloride,
2,2'-ethylphosphindiyl-bis(4,7-dimethylindenyl)hafnium dichloride,
2,2'-propylphosphindiyl-bis(4,7-dimethylindenyl)hafnium dichloride,
2,2'-butylphosphindiyl-bis(4,7-dimethylindenyl)hafnium dichloride,
2,2'-(1,2-dimethyldiphosphandiyl)-bis(4,7-dimethylindenyl)hafnium dichloride,
2,1'-phenylphosphindiyl(indenyl)(3-methylcyclopentadienyl)hafnium dichloride,
2,1'-methylphosphindiyl(indenyl)(3-methylcyclopentadienyl)hafnium dichloride,
2,1'-ethylphosphindiyl(indenyl)(3-methylcyclopentadienyl)hafnium dichloride,
2,1'-propylphosphindiyl(indenyl)(3-methylcyclopentadienyl)hafnium dichloride,
2,1'-butylphosphindiyl(indenyl)(3-methylcyclopentadienyl)hafnium dichloride,
2,1'-(1,2-dimethyldiphosphandiyl)(indenyl)(3-methylcyclopentadienyl)hafnium dichloride,
2,1'-phenylphosphindiyl(indenyl)(2,4-dimethylcyclopentadienyl)hafnium dichloride,
2,1'-methylphosphindiyl(indenyl)(2,4-dimethylcyclopentadienyl)hafnium dichloride,
2,1'-ethylphosphindiyl(indenyl)(2,4-dimethylcyclopentadienyl)hafnium dichloride,
2,1'-propylphosphindiyl(indenyl)(2,4-dimethylcyclopentadienyl)hafnium dichloride,
2,1'-butylphosphindiyl(indenyl)(2,4-dimethylcyclopentadienyl)hafnium dichloride,
2,1'-(1,2-dimethyldiphosphandiyl)(indenyl)(2,4-dimethylcyclopentadienyl)hafnium dichloride,
2,1'-phenylphosphindiyl(indenyl)(2-methyl-4-butylcyclopentadienyl)hafnium dichloride,
2,1'-methylphosphindiyl(indenyl)(2-methyl-4-butylcyclopentadienyl)hafnium dichloride,
2,1'-ethylphosphindiyl(indenyl)(2-methyl-4-butylcyclopentadienyl)hafnium dichloride,
2,1'-propylphosphindiyl(indenyl)(2-methyl-4-butylcyclopentadienyl)hafnium dichloride, 2,1'-butylphosphindiyl(indenyl)(2-methyl-4-butylcyclopentadienyl)hafnium dichloride,
2,1'-(1,2-dimethyldiphosphandiyl)(indenyl)(2-methyl-4-butylcyclopentadienyl)hafnium dichloride,
2,9'-phenylphosphindiyl(indenyl)(fluorenyl)hafnium dichloride,
2,9'-methylphosphindiyl(indenyl)(fluorenyl)hafnium dichloride,
2,9'-ethylphosphindiyl(indenyl)(fluorenyl)hafnium dichloride,
2,9'-propylphosphindiyl(indenyl)(fluorenyl)hafnium dichloride,
2,9'-butylphosphindiyl(indenyl)(fluorenyl)hafnium dichloride,
2,9'-(1,2-dimethyldiphosphandiyl)(indenyl)(fluorenyl)hafnium dichloride,
2,2'-phenylphosphindiyl-bis(indenyl)hafnium dimethyl,
2,2'-methylphosphindiyl-bis(indenyl)hafnium dimethyl,
2,2'-ethylphosphindiyl-bis(indenyl)hafnium dimethyl,
2,2'-propylphosphindiyl-bis(indenyl)hafnium dimethyl,
2,2'-butylphosphindiyl-bis(indenyl)hafnium dimethyl,
2,2'-(1,2-dimethyldiphosphandiyl)-bis(indenyl)hafnium dimethyl,
2,1'-phenylphosphindiyl(indenyl)(cyclopentadienyl) hafnium dimethyl,
2,1'-methylphosphindiyl(indenyl)(cyclopentadienyl) hafnium dimethyl,
2,1'-ethylphosphindiyl(indenyl)(cyclopentadienyl) hafnium dimethyl,
2,1'-propylphosphindiyl(indenyl)(cyclopentadienyl) hafnium dimethyl,
2,1'-butylphosphindiyl(indenyl)(cyclopentadienyl) hafnium dimethyl,
2,1'-1,2-dimethyldiphosphandiyl)(indenyl)(cyclopentadienyl)hafnium dimethyl,
2,2'-phenylphosphindiyl(indenyl)(tetrahydroindenyl) hafnium dimethyl,
2,2'-methylphosphindiyl(indenyl)(tetrahydroindenyl) hafnium dimethyl,
2,2'-ethylphosphindiyl(indenyl)(tetrahydroindenyl) hafnium dimethyl,
2,2'-propylphosphindiyl(indenyl)(tetrahydroindenyl) hafnium dimethyl,
2,2'-butylphosphindiyl(indenyl)(tetrahydroindenyl) hafnium dimethyl,
2,2'-(1,2-dimethyldiphosphandiyl)(indenyl)(tetrahydroindenyl)hafnium dimethyl,
2,2'-phenylphosphindiyl-bis(4-phenylindenyl)hafnium dimethyl,
2,2'-methylphosphindiyl-bis(4-phenylindenyl)hafnium dimethyl,
2,2'-ethylphosphindiyl-bis(4-phenylindenyl)hafnium dimethyl,
2,2'-propylphosphindiyl-bis(4-phenylindenyl)hafnium dimethyl,
2,2'-butylphosphindiyl-bis(4-phenylindenyl)hafnium dimethyl,
2,2'-(1,2-dimethyldiphosphandiyl)-bis(4-phenylindenyl) hafnium dimethyl,
2,2'-phenylphosphindiyl-bis(4,7-dimethylindenyl) hafnium dimethyl,
2,2'-methylphosphindiyl-bis(4,7-dimethylindenyl) hafnium dimethyl,
2,2'-ethylphosphindiyl-bis(4,7-dimethylindenyl)hafnium dimethyl,
2,2'-propylphosphindiyl-bis(4,7-dimethylindenyl) hafnium dimethyl,
2,2'-butylphosphindiyl-bis(4,7-dimethylindenyl)hafnium dimethyl,
2,2'-(1,2-dimethyldiphosphandiyl)-bis(4,7-dimethylindenyl)hafnium dimethyl,
2,1'-phenylphosphindiyl(indenyl)(3-methylcyclopentadienyl)hafnium dimethyl,
2,1'-methylphosphindiyl(indenyl)(3-methylcyclopentadienyl)hafnium dimethyl,
2,1'-ethylphosphindiyl(indenyl)(3-methylcyclopentadienyl)hafnium dimethyl,
2,1'-propylphosphindiyl(indenyl)(3-methylcyclopentadienyl)hafnium dimethyl,
2,1'-butylphosphindiyl(indenyl)(3-methylcyclopentadienyl)hafnium dimethyl,
2,1'-(1,2-dimethyldiphosphandiyl)(indenyl)(3-methylcyclopentadienyl)hafnium dimethyl,
2,1'-phenylphosphindiyl(indenyl)(2,4-dimethylcyclopentadienyl)hafnium dimethyl,
2,1'-methylphosphindiyl(indenyl)(2,4-dimethylcyclopentadienyl)hafnium dimethyl,
2,1'-ethylphosphindiyl(indenyl)(2,4-dimethylcyclopentadienyl)hafnium dimethyl,
2,1'-propylphosphindiyl(indenyl)(2,4-dimethylcyclopentadienyl)hafnium dimethyl,
2,1'-butylphosphindiyl(indenyl)(2,4-dimethylcyclopentadienyl)hafnium dimethyl,
2,1'-(1,2-dimethyldiphosphandiyl)(indenyl)(2,4-dimethylcyclopentadienyl)hafnium dimethyl,
2,1'-phenylphosphindiyl(indenyl)(2-methyl-4-butylcyclopentadienyl)hafnium dimethyl,
2,1'-methylphosphindiyl(indenyl)(2-methyl-4-butylcyclopentadienyl)hafnium dimethyl,
2,1'-ethylphosphindiyl(indenyl)(2-methyl-4-butylcyclopentadienyl)hafnium dimethyl,
2,1'-propylphosphindiyl(indenyl)(2-methyl-4-butylcyclopentadienyl)hafnium dimethyl,
2,1'-butylphosphindiyl(indenyl)(2-methyl-4-butylcyclopentadienyl)hafnium dimethyl,
2,1'-(1,2-dimethyldiphosphandiyl)(indenyl)(2-methyl-4-butylcyclopentadienyl)hafnium dimethyl,
2,9'-phenylphosphindiyl(indenyl)(fluorenyl)hafnium dimethyl,
2,9'-methylphosphindiyl(indenyl)(fluorenyl)hafnium dimethyl,
2,9'-ethylphosphindiyl(indenyl)(fluorenyl)hafnium dimethyl,
2,9'-propylphosphindiyl(indenyl)(fluorenyl)hafnium dimethyl,
2,9'-butylphosphindiyl(indenyl)(fluorenyl)hafnium dimethyl,
2,9'-(1,2-dimethyldiphosphandiyl)(indenyl)(fluorenyl) hafnium dimethyl,
2,2'-phenylphosphindiyl-bis(indenyl)hafnium dibenzyl,
2,2'-methylphosphindiyl-bis(indenyl)hafnium dibenzyl,
2,2'-ethylphosphindiyl-bis(indenyl)hafnium dibenzyl,
2,2'-propylphosphindiyl-bis(indenyl)hafnium dibenzyl,
2,2'-butylphosphindiyl-bis(indenyl)hafnium dibenzyl,
2,2'-(1,2-dimethyldiphosphandiyl)-bis(indenyl)hafnium dibenzyl,
2,1'-phenylphosphindiyl(indenyl)(cyclopentadienyl) hafnium dibenzyl,
2,1'-methylphosphindiyl(indenyl)(cyclopentadienyl) hafnium dibenzyl,
2,1'-ethylphosphindiyl(indenyl)(cyclopentadienyl) hafnium dibenzyl,
2,1'-propylphosphindiyl(indenyl)(cyclopentadienyl) hafnium dibenzyl, 2,1'-butylphosphindiyl(indenyl)(cyclopentadienyl) hafnium dibenzyl,
2,1'-1,2-dimethyldiphosphandiyl)(indenyl)(cyclopentadienyl)hafnium dibenzyl,
2,2'-phenylphosphindiyl(indenyl)(tetrahydroindenyl) hafnium dibenzyl,
2,2'-methylphosphindiyl(indenyl)(tetrahydroindenyl) hafnium dibenzyl,
2,2'-ethylphosphindiyl(indenyl)(tetrahydroindenyl) hafnium dibenzyl,
2,2'-propylphosphindiyl(indenyl)(tetrahydroindenyl) hafnium dibenzyl,
2,2'-butylphosphindiyl(indenyl)(tetrahydroindenyl) hafnium dibenzyl,
2,2'-(1,2-dimethyldiphosphandiyl)(indenyl)(tetrahydroindenyl)hafnium dibenzyl,
2,2'-phenylphosphindiyl-bis(4-phenylindenyl)hafnium dibenzyl,
2,2'-methylphosphindiyl-bis(4-phenylindenyl)hafnium dibenzyl,
2,2'-ethylphosphindiyl-bis(4-phenylindenyl)hafnium dibenzyl,
2,2'-propylphosphindiyl-bis(4-phenylindenyl)hafnium dibenzyl,
2,2'-butylphosphindiyl-bis(4-phenylindenyl)hafnium dibenzyl,
2,2'-(1,2-dimethyldiphosphandiyl)-bis(4-phenylindenyl) hafnium dibenzyl,
2,2'-phenylphosphindiyl-bis(4,7-dimethylindenyl) hafnium dibenzyl,
2,2'-methylphosphindiyl-bis(4,7-dimethylindenyl) hafnium dibenzyl,
2,2'-ethylphosphindiyl-bis(4,7-dimethylindenyl)hafnium dibenzyl,
2,2'-propylphosphindiyl-bis(4,7-dimethylindenyl) hafnium dibenzyl,
2,2'-butylphosphindiyl-bis(4,7-dimethylindenyl)hafnium dibenzyl,
2,2'-(1,2-dimethyldiphosphandiyl)-bis(4,7-dimethylindenyl)hafnium dibenzyl,
2,1'-phenylphosphindiyl(indenyl)(3-methylcyclopentadienyl)hafnium dibenzyl,
2,1'-methylphosphindiyl(indenyl)(3-methylcyclopentadienyl)hafnium dibenzyl,
2,1'-ethylphosphindiyl(indenyl)(3-methylcyclopentadienyl)hafnium dibenzyl,
2,1'-propylphosphindiyl(indenyl)(3-methylcyclopentadienyl)hafnium dibenzyl,
2,1'-butylphosphindiyl(indenyl)(3-methylcyclopentadienyl)hafnium dibenzyl,
2,1'-(1,2-dimethyldiphosphandiyl)(indenyl)(3-methylcyclopentadienyl)hafnium dibenzyl,
2,1'-phenylphosphindiyl(indenyl)(2,4-dimethylcyclopentadienyl)hafnium dibenzyl,
2,1'-methylphosphindiyl(indenyl)(2,4-dimethylcyclopentadienyl)hafnium dibenzyl,
2,1'-ethylphosphindiyl(indenyl)(2,4-dimethylcyclopentadienyl)hafnium dibenzyl,
2,1'-propylphosphindiyl(indenyl)(2,4-dimethylcyclopentadienyl)hafnium dibenzyl,
2,1'-butylphosphindiyl(indenyl)(2,4-dimethylcyclopentadienyl)hafnium dibenzyl,
2,1'-(1,2-dimethyldiphosphandiyl)(indenyl)(2,4-dimethylcyclopentadienyl)hafnium dibenzyl,
2,1'-phenylphosphindiyl(indenyl)(2-methyl-4-butylcyclopentadienyl)hafnium dibenzyl,
2,1'-methylphosphindiyl(indenyl)(2-methyl-4-butylcyclopentadienyl)hafnium dibenzyl,
2,1'-ethylphosphindiyl(indenyl)(2-methyl-4-butylcyclopentadienyl)hafnium dibenzyl,
2,1'-propylphosphindiyl(indenyl)(2-methyl-4-butylcyclopentadienyl)hafnium dibenzyl,
2,1'-butylphosphindiyl(indenyl)(2-methyl-4-butylcyclopentadienyl)hafnium dibenzyl,
2,1'-(1,2-dimethyldiphosphandiyl)(indenyl)(2-methyl-4-butylcyclopentadienyl)hafnium dibenzyl,
2,9'-phenylphosphindiyl(indenyl)(fluorenyl)hafnium dibenzyl,
2,9'-methylphosphindiyl(indenyl)(fluorenyl)hafnium dibenzyl,
2,9'-ethylphosphindiyl(indenyl)(fluorenyl)hafnium dibenzyl,
2,9'-propylphosphindiyl(indenyl)(fluorenyl)hafnium dibenzyl,
2,9'-butylphosphindiyl(indenyl)(fluorenyl)hafnium dibenzyl,
2,9'-(1,2-dimethyldiphosphandiyl)(indenyl)(fluorenyl) hafnium dibenzyl,
2,2'-phenylphosphindiyl-bis(indenyl)hafnium difluoride,
2,2'-methylphosphindiyl-bis(indenyl)hafnium difluoride,
2,2'-ethylphosphindiyl-bis(indenyl)hafnium difluoride,
2,2'-propylphosphindiyl-bis(indenyl)hafnium difluoride,
2,2'-butylphosphindiyl-bis(indenyl)hafnium difluoride,
2,2'-(1,2-dimethyldiphosphandiyl)-bis(indenyl)hafnium difluoride,
2,1'-phenylphosphindiyl(indenyl)(cyclopentadienyl) hafnium difluoride,
2,1'-methylphosphindiyl(indenyl)(cyclopentadienyl) hafnium difluoride,
2,1'-ethylphosphindiyl(indenyl)(cyclopentadienyl) hafnium difluoride,
2,1'-propylphosphindiyl(indenyl)(cyclopentadienyl) hafnium difluoride,
2,1'-butylphosphindiyl(indenyl)(cyclopentadienyl) hafnium difluoride,
2,1'-1,2-dimethyldiphosphandiyl)(indenyl)(cyclopentadienyl)hafnium difluoride,
2,2'-phenylphosphindiyl(indenyl)(tetrahydroindenyl) hafnium difluoride,
2,2'-methylphosphindiyl(indenyl)(tetrahydroindenyl) hafnium difluoride,
2,2'-ethylphosphindiyl(indenyl)(tetrahydroindenyl) hafnium difluoride,
2,2'-propylphosphindiyl(indenyl)(tetrahydroindenyl) hafnium difluoride,
2,2'-butylphosphindiyl(indenyl)(tetrahydroindenyl) hafnium difluoride,
2,2'-(1,2-dimethyldiphosphandiyl)(indenyl)(tetrahydroindenyl)hafnium difluoride,
2,2'-phenylphosphindiyl-bis(4-phenylindenyl)hafnium difluoride,
2,2'-methylphosphindiyl-bis(4-phenylindenyl)hafnium difluoride,
2,2'-ethylphosphindiyl-bis(4-phenylindenyl)hafnium difluoride,
2,2'-propylphosphindiyl-bis(4-phenylindenyl)hafnium difluoride,
2,2'-butylphosphindiyl-bis(4-phenylindenyl)hafnium difluoride,
2,2'-(1,2-dimethyldiphosphandiyl)-bis(4-phenylindenyl) hafnium difluoride,
2,2'-phenylphosphindiyl-bis(4,7-dimethylindenyl) hafnium difluoride, 2,2'-methylphosphindiyl-bis(4,7-dimethylindenyl)hafnium difluoride,
2,2'-ethylphosphindiyl-bis(4,7-dimethylindenyl)hafnium difluoride,
2,2'-propylphosphindiyl-bis(4,7-dimethylindenyl)hafnium difluoride,
2,2'-butylphosphindiyl-bis(4,7-dimethylindenyl)hafnium difluoride,
2,2'-(1,2-dimethyldiphosphandiyl)-bis(4,7-dimethylindenyl)hafnium difluoride,
2,1'-phenylphosphindiyl(indenyl)(3-methylcyclopentadienyl)hafnium difluoride,
2,1'-methylphosphindiyl(indenyl)(3-methylcyclopentadienyl)hafnium difluoride,
2,1'-ethylphosphindiyl(indenyl)(3-methylcyclopentadienyl)hafnium difluoride,
2,1'-propylphosphindiyl(indenyl)(3-methylcyclopentadienyl)hafnium difluoride,
2,1'-butylphosphindiyl(indenyl)(3-methylcyclopentadienyl)hafnium difluoride,
2,1'-(1,2-dimethyldiphosphandiyl)(indenyl)(3-methylcyclopentadienyl)hafnium difluoride,
2,1'-phenylphosphindiyl(indenyl)(2,4-dimethylcyclopentadienyl)hafnium difluoride,
2,1'-methylphosphindiyl(indenyl)(2,4-dimethylcyclopentadienyl)hafnium difluoride,
2,1'-ethylphosphindiyl(indenyl)(2,4-dimethylcyclopentadienyl)hafnium difluoride,
2,1'-propylphosphindiyl(indenyl)(2,4-dimethylcyclopentadienyl)hafnium difluoride,
2,1'-butylphosphindiyl(indenyl)(2,4-dimethylcyclopentadienyl)hafnium difluoride,
2,1'-(1,2-dimethyldiphosphandiyl)(indenyl)(2,4-dimethylcyclopentadienyl)hafnium difluoride,
2,1'-phenylphosphindiyl(indenyl)(2-methyl-4-butylcyclopentadienyl)hafnium difluoride,
2,1'-methylphosphindiyl(indenyl)(2-methyl-4-butylcyclopentadienyl)hafnium difluoride,
2,1'-ethylphosphindiyl(indenyl)(2-methyl-4-butylcyclopentadienyl)hafnium difluoride,
2,1'-propylphosphindiyl(indenyl)(2-methyl-4-butylcyclopentadienyl)hafnium difluoride,
2,1'-butylphosphindiyl(indenyl)(2-methyl-4-butylcyclopentadienyl)hafnium difluoride,
2,1'-(1,2-dimethyldiphosphandiyl)(indenyl)(2-methyl-4-butylcyclopentadienyl)hafnium difluoride,
2,9'-phenylphosphindiyl(indenyl)(fluorenyl)hafnium difluoride,
2,9'-methylphosphindiyl(indenyl)(fluorenyl)hafnium difluoride,
2,9'-ethylphosphindiyl(indenyl)(fluorenyl)hafnium difluoride,
2,9'-propylphosphindiyl(indenyl)(fluorenyl)hafnium difluoride,
2,9'-butylphosphindiyl(indenyl)(fluorenyl)hafnium difluoride,
2,9'-(1,2-dimethyldiphosphandiyl)(indenyl)(fluorenyl)hafnium difluoride,
2,2'-phenylphosphindiyl-bis(indenyl)titanium dichloride,
2,2'-methylphosphindiyl-bis(indenyl)titanium dichloride,
2,2'-ethylphosphindiyl-bis(indenyl)titanium dichloride,
2,2'-propylphosphindiyl-bis(indenyl)titanium dichloride,
2,2'-butylphosphindiyl-bis(indenyl)titanium dichloride,
2,2'-(1,2-dimethyldiphosphandiyl)-bis(indenyl)titanium dichloride,
2,1'-phenylphosphindiyl(indenyl)(cyclopentadienyl)titanium dichloride,
2,1'-methylphosphindiyl(indenyl)(cyclopentadienyl)titanium dichloride,
2,1'-ethylphosphindiyl(indenyl)(cyclopentadienyl)titanium dichloride,
2,1'-propylphosphindiyl(indenyl)(cyclopentadienyl)titanium dichloride,
2,1'-butylphosphindiyl(indenyl)(cyclopentadienyl)titanium dichloride,
2,1'-1,2-dimethyldiphosphandiyl)(indenyl)(cyclopentadienyl)titanium dichloride,
2,2'-phenylphosphindiyl(indenyl)(tetrahydroindenyl)titanium dichloride,
2,2'-methylphosphindiyl(indenyl)(tetrahydroindenyl)titanium dichloride,
2,2'-ethylphosphindiyl(indenyl)(tetrahydroindenyl)titanium dichloride,
2,2'-propylphosphindiyl(indenyl)(tetrahydroindenyl)titanium dichloride,
2,2'-butylphosphindiyl(indenyl)(tetrahydroindenyl)titanium dichloride,
2,2'-(1,2-dimethyldiphosphandiyl)(indenyl)(tetrahydroindenyl)titanium dichloride,
2,2'-phenylphosphindiyl-bis(4-phenylindenyl)titanium dichloride,
2,2'-methylphosphindiyl-bis(4-phenylindenyl)titanium dichloride,
2,2'-ethylphosphindiyl-bis(4-phenylindenyl)titanium dichloride,
2,2'-propylphosphindiyl-bis(4-phenylindenyl)titanium dichloride,
2,2'-butylphosphindiyl-bis(4-phenylindenyl)titanium dichloride,
2,2'-(1,2-dimethyldiphosphandiyl)-bis(4-phenylindenyl)titanium dichloride,
2,2'-phenylphosphindiyl-bis(4,7-dimethylindenyl)titanium dichloride,
2,2'-methylphosphindiyl-bis(4,7-dimethylindenyl)titanium dichloride,
2,2'-ethylphosphindiyl-bis(4,7-dimethylindenyl)titanium dichloride,
2,2'-propylphosphindiyl-bis(4,7-dimethylindenyl)titanium dichloride,
2,2'-butylphosphindiyl-bis(4,7-dimethylindenyl)titanium dichloride,
2,2'-(1,2-dimethyldiphosphandiyl)-bis(4,7-dimethylindenyl)titanium dichloride,
2,1'-phenylphosphindiyl(indenyl)(3-methylcyclopentadienyl)titanium dichloride,
2,1'-methylphosphindiyl(indenyl)(3-methylcyclopentadienyl)titanium dichloride,
2,1'-ethylphosphindiyl(indenyl)(3-methylcyclopentadienyl)titanium dichloride,
2,1'-propylphosphindiyl(indenyl)(3-methylcyclopentadienyl)titanium dichloride,
2,1'-butylphosphindiyl(indenyl)(3-methylcyclopentadienyl)titanium dichloride,
2,1'-(1,2-dimethyldiphosphandiyl)(indenyl)(3-methylcyclopentadienyl)titanium dichloride,
2,1'-phenylphosphindiyl(indenyl)(2,4-dimethylcyclopentadienyl)titanium dichloride,
2,1'-methylphosphindiyl(indenyl)(2,4-dimethylcyclopentadienyl)titanium dichloride,
2,1'-ethylphosphindiyl(indenyl)(2,4-dimethylcyclopentadienyl)titanium dichloride,
2,1'-propylphosphindiyl(indenyl)(2,4-dimethylcyclopentadienyl)titanium dichloride, 2,1'-butylphosphindiyl(indenyl)(2,4-dimethylcyclopentadienyl)titanium dichloride,
2,1'-(1,2-dimethyldiphosphandiyl)(indenyl)(2,4-dimethylcyclopentadienyl)titanium dichloride,
2,1'-phenylphosphindiyl(indenyl)(2-methyl-4-butylcyclopentadienyl)titanium dichloride,
2,1'-methylphosphindiyl(indenyl)(2-methyl-4-butylcyclopentadienyl)titanium dichloride,
2,1'-ethylphosphindiyl(indenyl)(2-methyl-4-butylcyclopentadienyl)titanium dichloride,
2,1'-propylphosphindiyl(indenyl)(2-methyl-4-butylcyclopentadienyl)titanium dichloride,
2,1'-butylphosphindiyl(indenyl)(2-methyl-4-butylcyclopentadienyl)titanium dichloride,
2,1'-(1,2-dimethyldiphosphandiyl)(indenyl)(2-methyl-4-butylcyclopentadienyl)titanium dichloride,
2,9'-phenylphosphindiyl(indenyl)(fluorenyl)titanium dichloride,
2,9'-methylphosphindiyl(indenyl)(fluorenyl)titanium dichloride,
2,9'-ethylphosphindiyl(indenyl)(fluorenyl)titanium dichloride,
2,9'-propylphosphindiyl(indenyl)(fluorenyl)titanium dichloride,
2,9'-butylphosphindiyl(indenyl)(fluorenyl)titanium dichloride,
2,9'-(1,2-dimethyldiphosphandiyl)(indenyl)(fluorenyl)titanium dichloride,
2,2'-phenylphosphindiyl-bis(indenyl)titanium dimethyl,
2,2'-methylphosphindiyl-bis(indenyl)titanium dimethyl,
2,2'-ethylphosphindiyl-bis(indenyl)titanium dimethyl,
2,2'-propylphosphindiyl-bis(indenyl)titanium dimethyl,
2,2'-butylphosphindiyl-bis(indenyl)titanium dimethyl,
2,2'-(1,2-dimethyldiphosphandiyl)-bis(indenyl)titanium dimethyl,
2,1'-phenylphosphindiyl(indenyl)(cyclopentadienyl)titanium dimethyl,
2,1'-methylphosphindiyl(indenyl)(cyclopentadienyl)titanium dimethyl,
2,1'-ethylphosphindiyl(indenyl)(cyclopentadienyl)titanium dimethyl,
2,1'-propylphosphindiyl(indenyl)(cyclopentadienyl)titanium dimethyl,
2,1'-butylphosphindiyl(indenyl)(cyclopentadienyl)titanium dimethyl,
2,1'-1,2-dimethyldiphosphandiyl)(indenyl)(cyclopentadienyl)titanium dimethyl,
2,2'-phenylphosphindiyl(indenyl)(tetrahydroindenyl)titanium dimethyl,
2,2'-methylphosphindiyl(indenyl)(tetrahydroindenyl)titanium dimethyl,
2,2'-ethylphosphindiyl(indenyl)(tetrahydroindenyl)titanium dimethyl,
2,2'-propylphosphindiyl(indenyl)(tetrahydroindenyl)titanium dimethyl,
2,2'-butylphosphindiyl(indenyl)(tetrahydroindenyl)titanium dimethyl,
2,2'-(1,2-dimethyldiphosphandiyl)(indenyl)(tetrahydroindenyl)titanium dimethyl,
2,2'-phenylphosphindiyl-bis(4-phenylindenyl)titanium dimethyl,
2,2'-methylphosphindiyl-bis(4-phenylindenyl)titanium dimethyl,
2,2'-ethylphosphindiyl-bis(4-phenylindenyl)titanium dimethyl,
2,2'-propylphosphindiyl-bis(4-phenylindenyl)titanium dimethyl,
2,2'-butylphosphindiyl-bis(4-phenylindenyl)titanium dimethyl,
2,2'-(1,2-dimethyldiphosphandiyl)-bis(4-phenylindenyl)titanium dimethyl,
2,2'-phenylphosphindiyl-bis(4,7-dimethylindenyl)titanium dimethyl,
2,2'-methylphosphindiyl-bis(4,7-dimethylindenyl)titanium dimethyl,
2,2'-ethylphosphindiyl-bis(4,7-dimethylindenyl)titanium dimethyl,
2,2'-propylphosphindiyl-bis(4,7-dimethylindenyl)titanium dimethyl,
2,2'-butylphosphindiyl-bis(4,7-dimethylindenyl)titanium dimethyl,
2,2'-(1,2-dimethyldiphosphandiyl)-bis(4,7-dimethylindenyl)titanium dimethyl,
2,1'-phenylphosphindiyl(indenyl)(3-methylcyclopentadienyl)titanium dimethyl,
2,1'-methylphosphindiyl(indenyl)(3-methylcyclopentadienyl)titanium dimethyl,
2,1'-ethylphosphindiyl(indenyl)(3-methylcyclopentadienyl)titanium dimethyl,
2,1'-propylphosphindiyl(indenyl)(3-methylcyclopentadienyl)titanium dimethyl,
2,1'-butylphosphindiyl(indenyl)(3-methylcyclopentadienyl)titanium dimethyl,
2,1'-(1,2-dimethyldiphosphandiyl)(indenyl)(3-methylcyclopentadienyl)titanium dimethyl,
2,1'-phenylphosphindiyl(indenyl)(2,4-dimethylcyclopentadienyl)titanium dimethyl,
2,1'-methylphosphindiyl(indenyl)(2,4-dimethylcyclopentadienyl)titanium dimethyl,
2,1'-ethylphosphindiyl(indenyl)(2,4-dimethylcyclopentadienyl)titanium dimethyl,
2,1'-propylphosphindiyl(indenyl)(2,4-dimethylcyclopentadienyl)titanium dimethyl,
2,1'-butylphosphindiyl(indenyl)(2,4-dimethylcyclopentadienyl)titanium dimethyl,
2,1'-(1,2-dimethyldiphosphandiyl)(indenyl)(2,4-dimethylcyclopentadienyl)titanium dimethyl,
2,1'-phenylphosphindiyl(indenyl)(2-methyl-4-butylcyclopentadienyl)titanium dimethyl,
2,1'-methylphosphindiyl(indenyl)(2-methyl-4-butylcyclopentadienyl)titanium dimethyl,
2,1'-ethylphosphindiyl(indenyl)(2-methyl-4-butylcyclopentadienyl)titanium dimethyl,
2,1'-propylphosphindiyl(indenyl)(2-methyl-4-butylcyclopentadienyl)titanium dimethyl,
2,1'-butylphosphindiyl(indenyl)(2-methyl-4-butylcyclopentadienyl)titanium dimethyl,
2,1'-(1,2-dimethyldiphosphandiyl)(indenyl)(2-methyl-4-butylcyclopentadienyl)titanium dimethyl,
2,9'-phenylphosphindiyl(indenyl)(fluorenyl)titanium dimethyl,
2,9'-methylphosphindiyl(indenyl)(fluorenyl)titanium dimethyl,
2,9'-ethylphosphindiyl(indenyl)(fluorenyl)titanium dimethyl,
2,9'-propylphosphindiyl(indenyl)(fluorenyl)titanium dimethyl,
2,9'-butylphosphindiyl(indenyl)(fluorenyl)titanium dimethyl,
2,9'-(1,2-dimethyldiphosphandiyl)(indenyl)(fluorenyl)titanium dimethyl,
2,2'-phenylphosphindiyl-bis(indenyl)titanium dibenzyl,
2,2'-methylphosphindiyl-bis(indenyl)titanium dibenzyl,
2,2'-ethylphosphindiyl-bis(indenyl)titanium dibenzyl, 2,2'-propylphosphindiyl-bis(indenyl)titanium dibenzyl,
2,2'-butylphosphindiyl-bis(indenyl)titanium dibenzyl,
2,2'-(1,2-dimethyldiphosphandiyl)-bis(indenyl)titanium dibenzyl,
2,1'-phenylphosphindiyl(indenyl)(cyclopentadienyl)titanium dibenzyl,
2,1'-methylphosphindiyl(indenyl)(cyclopentadienyl)titanium dibenzyl,
2,1'-ethylphosphindiyl(indenyl)(cyclopentadienyl)titanium dibenzyl,
2,1'-propylphosphindiyl(indenyl)(cyclopentadienyl)titanium dibenzyl,
2,1'-butylphosphindiyl(indenyl)(cyclopentadienyl)titanium dibenzyl,
2,1'-1,2-dimethyldiphosphandiyl)(indenyl)(cyclopentadienyl)titanium dibenzyl,
2,2'-phenylphosphindiyl(indenyl)(tetrahydroindenyl)titanium dibenzyl,
2,2'-methylphosphindiyl(indenyl)(tetrahydroindenyl)titanium dibenzyl,
2,2'-ethylphosphindiyl(indenyl)(tetrahydroindenyl)titanium dibenzyl,
2,2'-propylphosphindiyl(indenyl)(tetrahydroindenyl)titanium dibenzyl,
2,2'-butylphosphindiyl(indenyl)(tetrahydroindenyl)titanium dibenzyl,
2,2'-(1,2-dimethyldiphosphandiyl)(indenyl)(tetrahydroindenyl)titanium dibenzyl,
2,2'-phenylphosphindiyl-bis(4-phenylindenyl)titanium dibenzyl,
2,2'-methylphosphindiyl-bis(4-phenylindenyl)titanium dibenzyl,
2,2'-ethylphosphindiyl-bis(4-phenylindenyl)titanium dibenzyl,
2,2'-propylphosphindiyl-bis(4-phenylindenyl)titanium dibenzyl,
2,2'-butylphosphindiyl-bis(4-phenylindenyl)titanium dibenzyl,
2,2'-(1,2-dimethyldiphosphandiyl)-bis(4-phenylindenyl)titanium dibenzyl,
2,2'-phenylphosphindiyl-bis(4,7-dimethylindenyl)titanium dibenzyl,
2,2'-methylphosphindiyl-bis(4,7-dimethylindenyl)titanium dibenzyl,
2,2'-ethylphosphindiyl-bis(4,7-dimethylindenyl)titanium dibenzyl,
2,2'-propylphosphindiyl-bis(4,7-dimethylindenyl)titanium dibenzyl,
2,2'-butylphosphindiyl-bis(4,7-dimethylindenyl)titanium dibenzyl,
2,2'-(1,2-dimethyldiphosphandiyl)-bis(4,7-dimethylindenyl)titanium dibenzyl,
2,1'-phenylphosphindiyl(indenyl)(3-methylcyclopentadienyl)titanium dibenzyl,
2,1'-methylphosphindiyl(indenyl)(3-methylcyclopentadienyl)titanium dibenzyl,
2,1'-ethylphosphindiyl(indenyl)(3-methylcyclopentadienyl)titanium dibenzyl,
2,1'-propylphosphindiyl(indenyl)(3-methylcyclopentadienyl)titanium dibenzyl,
2,1'-butylphosphindiyl(indenyl)(3-methylcyclopentadienyl)titanium dibenzyl,
2,1'-(1,2-dimethyldiphosphandiyl)(indenyl)(3-methylcyclopentadienyl)titanium dibenzyl,
2,1'-phenylphosphindiyl(indenyl)(2,4-dimethylcyclopentadienyl)titanium dibenzyl,
2,1'-methylphosphindiyl(indenyl)(2,4-dimethylcyclopentadienyl)titanium dibenzyl,
2,1'-ethylphosphindiyl(indenyl)(2,4-dimethylcyclopentadienyl)titanium dibenzyl,
2,1'-propylphosphindiyl(indenyl)(2,4-dimethylcyclopentadienyl)titanium dibenzyl,
2,1'-butylphosphindiyl(indenyl)(2,4-dimethylcyclopentadienyl)titanium dibenzyl,
2,1'-(1,2-dimethyldiphosphandiyl)(indenyl)(2,4-dimethylcyclopentadienyl)titanium dibenzyl,
2,1'-phenylphosphindiyl(indenyl)(2-methyl-4-butylcyclopentadienyl)titanium dibenzyl,
2,1'-methylphosphindiyl(indenyl)(2-methyl-4-butylcyclopentadienyl)titanium dibenzyl,
2,1'-ethylphosphindiyl(indenyl)(2-methyl-4-butylcyclopentadienyl)titanium dibenzyl,
2,1'-propylphosphindiyl(indenyl)(2-methyl-4-butylcyclopentadienyl)titanium dibenzyl,
2,1'-butylphosphindiyl(indenyl)(2-methyl-4-butylcyclopentadienyl)titanium dibenzyl,
2,1'-(1,2-dimethyldiphosphandiyl)(indenyl)(2-methyl-4-butylcyclopentadienyl)titanium dibenzyl,
2,9'-phenylphosphindiyl(indenyl)(fluorenyl)titanium dibenzyl,
2,9'-methylphosphindiyl(indenyl)(fluorenyl)titanium dibenzyl,
2,9'-ethylphosphindiyl(indenyl)(fluorenyl)titanium dibenzyl,
2,9'-propylphosphindiyl(indenyl)(fluorenyl)titanium dibenzyl,
2,9'-butylphosphindiyl(indenyl)(fluorenyl)titanium dibenzyl,
2,9'-(1,2-dimethyldiphosphandiyl)(indenyl)(fluorenyl)titanium dibenzyl,
2,2'-phenylphosphindiyl-bis(indenyl)titanium difluoride,
2,2'-methylphosphindiyl-bis(indenyl)titanium difluoride,
2,2'-ethylphosphindiyl-bis(indenyl)titanium difluoride,
2,2'-propylphosphindiyl-bis(indenyl)titanium difluoride,
2,2'-butylphosphindiyl-bis(indenyl)titanium difluoride,
2,2'-(1,2-dimethyldiphosphandiyl)-bis(indenyl)titanium difluoride,
2,1'-phenylphosphindiyl(indenyl)(cyclopentadienyl)titanium difluoride,
2,1'-methylphosphindiyl(indenyl)(cyclopentadienyl)titanium difluoride,
2,1'-ethylphosphindiyl(indenyl)(cyclopentadienyl)titanium difluoride,
2,1'-propylphosphindiyl(indenyl)(cyclopentadienyl)titanium difluoride,
2,1'-butylphosphindiyl(indenyl)(cyclopentadienyl)titanium difluoride,
2,1'-1,2-dimethyldiphosphandiyl)(indenyl)(cyclopentadienyl)titanium difluoride,
2,2'-phenylphosphindiyl(indenyl)(tetrahydroindenyl)titanium difluoride,
2,2'-methylphosphindiyl(indenyl)(tetrahydroindenyl)titanium difluoride,
2,2'-ethylphosphindiyl(indenyl)(tetrahydroindenyl)titanium difluoride,
2,2'-propylphosphindiyl(indenyl)(tetrahydroindenyl)titanium difluoride,
2,2'-butylphosphindiyl(indenyl)(tetrahydroindenyl)titanium difluoride,
2,2'-(1,2-dimethyldiphosphandiyl)(indenyl)(tetrahydroindenyl)titanium difluoride,
2,2'-phenylphosphindiyl-bis(4-phenylindenyl)titanium difluoride, 2,2'-methylphosphindiyl-bis(4-phenylindenyl)titanium difluoride,
2,2'-ethylphosphindiyl-bis(4-phenylindenyl)titanium difluoride,
2,2'-propylphosphindiyl-bis(4-phenylindenyl)titanium difluoride,
2,2'-butylphosphindiyl-bis(4-phenylindenyl)titanium difluoride,
2,2'-(1,2-dimethyldiphosphandiyl)-bis(4-phenylindenyl) titanium difluoride,
2,2'-phenylphosphindiyl-bis(4,7-dimethylindenyl)titanium difluoride,
2,2'-methylphosphindiyl-bis(4,7-dimethylindenyl)titanium difluoride,
2,2'-ethylphosphindiyl-bis(4,7-dimethylindenyl)titanium difluoride,
2,2'-propylphosphindiyl-bis(4,7-dimethylindenyl)titanium difluoride,
2,2'-butylphosphindiyl-bis(4,7-dimethylindenyl)titanium difluoride,
2,2'-(1,2-dimethyldiphosphandiyl)-bis(4,7-dimethylindenyl)titanium difluoride,
2,1'-phenylphosphindiyl(indenyl)(3-methylcyclopentadienyl)titanium difluoride,
2,1'-methylphosphindiyl(indenyl)(3-methylcyclopentadienyl)titanium difluoride,
2,1'-ethylphosphindiyl(indenyl)(3-methylcyclopentadienyl)titanium difluoride,
2,1'-propylphosphindiyl(indenyl)(3-methylcyclopentadienyl)titanium difluoride,
2,1'-butylphosphindiyl(indenyl)(3-methylcyclopentadienyl)titanium difluoride,
2,1'-(1,2-dimethyldiphosphandiyl)(indenyl)(3-methylcyclopentadienyl)titanium difluoride,
2,1'-phenylphosphindiyl(indenyl)(2,4-dimethylcyclopentadienyl)titanium difluoride,
2,1'-methylphosphindiyl(indenyl)(2,4-dimethylcyclopentadienyl)titanium difluoride,
2,1'-ethylphosphindiyl(indenyl)(2,4-dimethylcyclopentadienyl)titanium difluoride,
2,1'-propylphosphindiyl(indenyl)(2,4-dimethylcyclopentadienyl)titanium difluoride,
2,1'-butylphosphindiyl(indenyl)(2,4-dimethylcyclopentadienyl)titanium difluoride,
2,1'-(1,2-dimethyldiphosphandiyl)(indenyl)(2,4-dimethylcyclopentadienyl)titanium difluoride,
2,1'-phenylphosphindiyl(indenyl)(2-methyl-4-butylcyclopentadienyl)titanium difluoride,
2,1'-methylphosphindiyl(indenyl)(2-methyl-4-butylcyclopentadienyl)titanium difluoride,
2,1'-ethylphosphindiyl(indenyl)(2-methyl-4-butylcyclopentadienyl)titanium difluoride,
2,1'-propylphosphindiyl(indenyl)(2-methyl-4-butylcyclopentadienyl)titanium difluoride,
2,1'-butylphosphindiyl(indenyl)(2-methyl-4-butylcyclopentadienyl)titanium difluoride,
2,1'-(1,2-dimethyldiphosphandiyl)(indenyl)(2-methyl-4-butylcyclopentadienyl)titanium difluoride,
2,9'-phenylphosphindiyl(indenyl)(fluorenyl)titanium difluoride,
2,9'-methylphosphindiyl(indenyl)(fluorenyl)titanium difluoride,
2,9'-ethylphosphindiyl(indenyl)(fluorenyl)titanium difluoride,
2,9'-propylphosphindiyl(indenyl)(fluorenyl)titanium difluoride,
2,9'-butylphosphindiyl(indenyl)(fluorenyl)titanium difluoride, and
2,9'-(1,2-dimethyldiphosphandiyl)(indenyl)(fluorenyl)titanium difluoride.

32. A catalyst system comprising an activator and the compound of claim 1.

33. The catalyst system of claim 32 wherein the activator comprises an alumoxane.

34. The catalyst system of claim 32 wherein the activator comprises a non-coordinating anion containing metalloid-free cyclopentadienide ion.

35. The catalyst system of claim 32 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

36. The catalyst system of claim 32 wherein the activator is selected from the group consisting of N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra(perfluorophenyl)borate.

37. A catalyst system comprising an activator and the compound of claim 9.

38. The catalyst system of claim 37 wherein the activator comprises an alumoxane.

39. The catalyst system of claim 37 wherein the activator comprises a non-coordinating anion containing metalloid-free cyclopentadienide ion.

40. The catalyst system of claim 37 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

41. The catalyst system of claim 37 wherein the activator is selected from the group consisting of N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra(perfluorophenyl)borate.

42. A catalyst system comprising an activator and the compound of claim 19.

43. The catalyst system of claim 42 wherein the activator comprises an alumoxane.

44. The catalyst system of claim 42 wherein the activator comprises a non-coordinating anion containing metalliod-free cyclopentadienide ion.

45. The catalyst system of claim 42 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

46. The catalyst system of claim 42 wherein the activator is selected from the group consisting of N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra(perfluorophenyl)borate.

47. A catalyst system comprising the catalyst compound of claim 31 and an activator.

48. The catalyst system of claim 47 wherein the activator comprises an alumoxane.

49. The catalyst system of claim 47 wherein the activator is selected from the group consisting of trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis (pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

50. A catalyst system comprising the compound of claim 31 and an activator selected from the group consisting of N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, and triphenylcarbenium tetra(perfluorophenyl)borate.

51. A method to polymerize unsaturated monomers comprising contacting the catalyst system of claim 32 with unsaturated monomers.

52. The method of claim 51 wherein the monomers comprise ethylene.

53. The method of claim 51 wherein the monomers comprise propylene.

54. The method of claim 51 wherein the monomers comprise ethylene and one or more comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norboenadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

55. A method to polymerize unsaturated monomers comprising contacting the catalyst system of claim 37 with unsaturated monomers.

56. The method of claim 55 wherein the monomers comprise ethylene.

57. The method of claim 55 wherein the monomers comprise propylene.

58. The method of claim 55 wherein the monomers comprise ethylene and one or more comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

59. A method to polymerize unsaturated monomers comprising contacting the catalyst system of claim 42 with unsaturated monomers.

60. The method of claim 59 wherein the monomers comprise ethylene.

61. The method of claim 59 wherein the monomers comprise propylene.

62. The method of claim 59 wherein the monomers comprise ethylene and one or more comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, l-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

63. A method to polymerize unsaturated monomers comprising contacting the catalyst system of claim 49 with unsaturated monomers.

64. The method of claim 63 wherein the monomers comprise ethylene.

65. The method of claim 63 wherein the monomers comprise propylene.

66. The method of claim 63 wherein the monomers comprise ethylene and one or more comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,1 3-tetradecene and 9-methyl-1,9-decadiene.

67. The method of claim 51 wherein the monomers comprise propylene and one or more comonomers selected from the group consisting of 1-butene, 1-pentene, 1-hexene, 1-heptene. 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-cicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene. 3methyl-1-pentene, 5-methyl-1-nonene, 3,5,5-trimethyl-1-hexene, vinylcyclohexane, vinylnorbornant, cyclobutene. cyclopentene. cyclohexene, cycloheptene, cyclooctent, cyciononerie, cyclodecene, norbornene, 4-zn ethylnorbornefle, 2-methylcyclopentent, 4-methylcyclopentene, vinylcyclohexane. norbornadiene, dicyclopentadiefle, 5-ethylidene-2-norboment, vinylcyclohexene, 5-vinyl-2-norbornbfle, 1,3-divinylcyclopentane, 1,2-divinylcyclohexane, 1,3-divinylcyc1ohexafle, 1,4-divinylcyclohexane, 1,5-divinylcycloottafle, 1-allyl-4-vinylcycloheXaflt, 1,4-diallylcyclohexane, 1-allyl-5-vinylcycloottsfle, 1,5-diallylcyclooctafle, styrene, para-methylstyrene, para-t-butylstyrene, vinylnaplithylene, vinyltoluene, divinylbenzene. 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

68. The method of claim 51 wherein the monomers comprise ethylene and propylene and one or more comonomers selected from the group consisting of 1-butene, 1-pentene, 1-hexene, 1-heptene, 1-octene, 1-nonene. 1-decene, 1-undecene 1-dodecene, 1-tridecene, 1-tetradecene, 1-pentadecene. 1-hexadecene, 1-heptadecene, 1-octadecene, 1-nonadecene, 1-cicosene, 1heneicosene, 1-docosene, 1-tricosene, 1-tetracosene, 1-pentacosent, 1-hexacosene, 1-heptacosene, 1-octacosent, 1-nonacosene, 1-triacontene, 4-methyl-1-pentene, 3-xnethyl-1-pentent, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcylopentene, 4-methylcyclopentene, vinylcyclohexane, norbornadiene, dicyclopentadiene, 5-ethylidene-2-norbomene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene. 1,6-heptadiene, 6-methyl-1,6-heptadiene.

1,7-octadiene, 7-methyl-1,7-octadiene, 1,9-decadiene, 1,11-dodecene, 1,13-tetradecene and 9-methyl-1,9-decadiene.

69. The method of claim 59 wherein the monomers comprise propylene and one or mare comonomers selected from the group consisting of 1-butene, 1-pentene, 1-hexene. 1-heptene, 1-octene, 1-nonene, 1-decene, 1-undecene 1-dodecene, 1-tridecene, 1-tetradecene, 1pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-niethyl-1-pentene, 5-methyl-1-nonene, 3,5,5-trimethyl-1-hexene. vinylcyciohexane, vinylnorbornane, cyclobutene, cyclopeatene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrens, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene. 6-methyl-1,6-heptadiene. 1,7-octadiene, 7-methyl-1,7-octadiene, 1,9-decadiene, 1,11-dodecene. 1,13-tetradecene and 9-methyl-1,9-decadiene.

70. The method of claim 59 wherein the monomers comprise ethylene and propylene and one or more comonomers selected from the group consisting of 1-butene, 1-pentene, 1-hexene, 1-heptene, 1-octene, 1-nonene. 1-decene, 1-undecene 1-dodecene, 1-tridecene, 1-tetradecene, 1-pentadecene, 1-hexadecene, 1-heptadecene, 1-octadecene, 1-nanadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane. 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene. 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

71. The method of claim 63 wherein the monomers comprise propylene and one or mare comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-ejeosene, 1-heneicosene, 1-docosene, 1-tricosene, 1-tetracosene, 1-pentacosene, 1-hexacosene, 1-heptacosene, 1-actacosene, 1-nonacosene, 1-triacontene, 4-methyl-1-pentene, 3-methyl-1-pentene, 5-methyl-1-nonene, 3,5,5-trixnetbyl-1-hexene, vinylcyclohexane, vinylnorbornane, cyclobutene, cyclopentene, cyclohexene, cycloheptene, cyclooctene, cyclononene, cyclodecene, norbornene, 4-methylnotbornene, 2-methylcyclopentene, 4-methylcyclopentene, vinylcyclohexane, norbornadiene, dicyclopentadiene, 5-ethylidene-2-norbomene, vinylcyclohexene, 5-vinyl-2-norborflene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, styrene, para-methylstyrene, para-t-butylstyrene, vinylnaphthylene, vinyltoluene, divinylbenzene, 1,4-hexadiene, 1,5-hexadiene, 1,5-heptadiene, 1,6-heptadiene, 6-methyl-1,6-heptadiene, 1,7-octadieue, 7-methyl-1,7-octadiene, 1,9-decadiene, 1,11-clodecene, 1,13-tetradecene and 9-methyl-1,9-decadiene.

72. The method of claim 63 wherein the monomers comprise ethylene and propylene and one or more comonomers selected from the group consisting of 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-cicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene. 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-niethylnorbornene, 2-methylcyclopentene, 4-methylcyclopentene, vinylcyclohexane, norbomadiene, dicyclopentadiene, 5-ethylidene-2-norbomene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane. styrene, para-methylstyrene, para-t-butylstyrene, vinylnaphthylene, vinyltoluene, divinylbeuzene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

73. The catalyst system of claim 32 wherein the activator represented by the following formula:

$(L^{}-H)_d^+(A^{d-})$ wherein $L^{}$ is an neutral Lewis base;
H is hydrogen;
$(L^{**}-H)^+$ is a Bronsted acid;
$A^{d-}$ is a non-coordinating anion having the charge d;
d is an integer from 1 to 3.

74. The catalyst system of claim 37 wherein the activator represented by the following formula:

$(L^{}-H)_d^+(A^{d-})$ wherein $L^{}$ is an neutral Lewis base;
H is hydrogen;
$(L^{**}-H)^+$ is a Bronsted acid;
$A^{d-}$ is a non-coordinating anion having the charge d; and
d is an integer from 1 to 3.

75. The catalyst system of claim 42 wherein the activator represented by the following formula:

$(L^{}-H)_d^+(A^{d-})$ wherein $L^{}$ is an neulral Lewis base;
H is hydrogen;
$(L^{**}-H)^+$ is a Bronsted acid;
$A^{d-}$ is a nan-coordinating anion having the charge d; and
d is an integer from 1 to 3.

* * * * *